US008759305B2

(12) United States Patent
Barrat et al.

(10) Patent No.: US 8,759,305 B2
(45) Date of Patent: Jun. 24, 2014

(54) METHODS AND COMPOSITIONS FOR INHIBITION OF INNATE IMMUNE RESPONSES AND AUTOIMMUNITY

(75) Inventors: Franck Barrat, San Mateo, CA (US); Robert L. Coffman, Portola Valley, CA (US)

(73) Assignee: Dynavax Technologies Corporation, Berkeley, CA (US)

( * ) Notice: Subject to any disclaimer, the term of this patent is extended or adjusted under 35 U.S.C. 154(b) by 1874 days.

(21) Appl. No.: 11/212,297

(22) Filed: Aug. 24, 2005

(65) Prior Publication Data
US 2007/0238678 A1 Oct. 11, 2007

Related U.S. Application Data

(60) Provisional application No. 60/606,833, filed on Sep. 1, 2004.

(51) Int. Cl.
A61K 48/00 (2006.01)
C12N 15/11 (2006.01)
C07H 21/02 (2006.01)
C07H 21/04 (2006.01)

(52) U.S. Cl.
USPC .......................................... 514/44; 536/23.1

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | |
| 4,587,329 A | 5/1986 | Tomalia et al. | |
| 4,650,675 A | 3/1987 | Borel et al. | |
| 4,849,513 A | 7/1989 | Smith et al. | |
| 4,910,300 A | 3/1990 | Urdea et al. | |
| 4,948,882 A | 8/1990 | Ruth | |
| 5,015,733 A | 5/1991 | Smith et al. | |
| 5,093,232 A | 3/1992 | Urdea et al. | |
| 5,118,800 A | 6/1992 | Smith et al. | |
| 5,118,802 A | 6/1992 | Smith et al. | |
| 5,124,246 A | 6/1992 | Urdea et al. | |
| 5,171,264 A | 12/1992 | Merrill | |
| 5,338,532 A | 8/1994 | Tomalia et al. | |
| 5,391,723 A | 2/1995 | Priest | |
| 5,453,496 A | 9/1995 | Caruthers et al. | |
| 5,460,831 A | 10/1995 | Kossovsky et al. | |
| 5,552,391 A | 9/1996 | Coutts et al. | |
| 6,080,580 A * | 6/2000 | Baker et al. | 435/375 |
| 6,096,722 A * | 8/2000 | Bennett et al. | 514/44 A |
| 6,117,657 A | 9/2000 | Usman et al. | |
| 6,177,414 B1 | 1/2001 | Tomalia et al. | |
| 6,225,292 B1 | 5/2001 | Raz et al. | |
| 2001/0006945 A1 * | 7/2001 | Agrawal | 514/44 |
| 2003/0087848 A1 | 5/2003 | Bratzler et al. | |
| 2004/0009949 A1 * | 1/2004 | Krieg | 514/44 |
| 2004/0053880 A1 | 3/2004 | Krieg | |
| 2005/0239733 A1 * | 10/2005 | Jurk et al. | 514/44 |
| 2006/0193821 A1 | 8/2006 | Epstein et al. | |
| 2006/0193869 A1 | 8/2006 | Barrat et al. | |
| 2011/0003885 A1 | 1/2011 | Barrat et al. | |
| 2011/0123561 A1 | 5/2011 | Barrat et al. | |

FOREIGN PATENT DOCUMENTS

| | | |
|---|---|---|
| EP | 0 313 219 A1 | 4/1989 |
| EP | 0 313 219 A3 | 4/1989 |
| EP | 0 313 219 B1 | 4/1989 |
| WO | WO-89/02439 A1 | 3/1989 |
| WO | WO-95/07073 A1 | 3/1995 |
| WO | WO-96/40197 A1 | 12/1996 |
| WO | WO-97/46251 A1 | 12/1997 |
| WO | WO-98/16247 A1 | 4/1998 |
| WO | WO-98/55495 A2 | 12/1998 |
| WO | WO-98/55495 A3 | 12/1998 |
| WO | WO-00/34231 A1 | 6/2000 |
| WO | WO-00/61151 A2 | 10/2000 |
| WO | WO-00/61151 A3 | 10/2000 |
| WO | WO-00/75105 A1 | 12/2000 |
| WO | WO-01/22972 A2 | 4/2001 |
| WO | WO-01/22972 A3 | 4/2001 |
| WO | WO-01/68697 A2 | 9/2001 |
| WO | WO-01/68697 A3 | 9/2001 |
| WO | WO-02/10438 A2 | 2/2002 |
| WO | WO-02/10438 A3 | 2/2002 |
| WO | WO-02/095010 A2 | 11/2002 |
| WO | WO-02/095010 A3 | 11/2002 |
| WO | WO-03/085110 A2 | 10/2003 |
| WO | WO-03/085110 A3 | 10/2003 |
| WO | WO-03/103586 A2 | 12/2003 |
| WO | WO-03/103586 A3 | 12/2003 |
| WO | WO-03/103708 A1 | 12/2003 |
| WO | WO-2004/014322 A2 | 2/2004 |
| WO | WO-2004/014322 A3 | 2/2004 |
| WO | WO-2004/047734 A2 | 6/2004 |
| WO | WO-2004/047734 A3 | 6/2004 |
| WO | WO-2004/058179 A2 | 7/2004 |
| WO | WO-2004/058179 A3 | 7/2004 |
| WO | WO-2005/086835 A2 | 9/2005 |
| WO | WO-2005/086835 A3 | 9/2005 |
| WO | WO-2006/028742 A2 | 3/2006 |

(Continued)

OTHER PUBLICATIONS

U.S. Appl. No. 60/516,221, filed Oct. 31, 2003.*
Barrat et al. Immunological Reviews 2008, vol. 223:271-283.*
Agrawal, S. et al. (1986). "Efficient Methods for Attaching Non-Radioactive Labels to the 5' Ends of Synthetic Oligodeoxyribonucleotides," *Nucleic Acids Res.* 14(15):6227-6245.
Akira, S. et al. (2003). "Recognition of Pathogen-Associated Molecular Patterns by TLR Family," *Immunol. Lett.* 85:85-95.
Alexopoulou, L. et al. (Oct. 18, 2001). "Recognition of Double-Stranded RNA and Activation of NF-κB by Toll-Like Receptor 3," *Nature* 413:732-738.

(Continued)

*Primary Examiner* — Oluwatosin Ogunbiyi
(74) *Attorney, Agent, or Firm* — Morrison & Foerster LLP

(57) ABSTRACT

The invention provides immunoregulatory polynucleotides and methods for immunoregulation of individuals using the immunoregulatory polynucleotides.

32 Claims, 23 Drawing Sheets

(56) References Cited

FOREIGN PATENT DOCUMENTS

| WO | WO-2006/028742 A3 | 3/2006 |
|---|---|---|
| WO | WO-2006/066003 A2 | 6/2006 |
| WO | WO-2006/066003 A3 | 6/2006 |
| WO | WO-2007/075626 A2 | 7/2007 |
| WO | WO-2007/075626 A3 | 7/2007 |
| WO | WO-2007/095387 A2 | 8/2007 |
| WO | WO-2007/095387 A3 | 8/2007 |
| WO | WO-2007/095387 A8 | 8/2007 |
| WO | WO-2007/117686 A2 | 10/2007 |
| WO | WO-2007/117686 A3 | 10/2007 |
| WO | WO-2009/055076 A2 | 4/2009 |
| WO | WO-2009/055076 A3 | 4/2009 |

OTHER PUBLICATIONS

Altmann, S. et al. (1995). "NMR Studies of DNA Duplexes Singly Cross-Linked by Different Synthetic Linkers," *Nucleic Acids Res.* 23(23):4827-4835.

Ashman, R.F. et al. (Apr. 2005). "Sequence Requirements for Oligodeoxyribonucleotide Inhibitory Activity," *International Immunology* 17(4):411-420.

Barrat, F.J. et al. (Oct. 17, 2005). "Nucleic Acids of Mammalian Origin can act as Endogenous Ligands for Toll-like Receptors and may Promote Systemic Lupus Erythematosus," *J. Exp. Med.* 202(8):1131-1139.

Bartley, J.P. et al. (1997). "Solution Conformation of an Intramolecular DNA Triplex Containing a Nonnucleotide Linker: Comparison with the DNA Duplex," *Biochemistry* 36:14502-14511.

Bauer, S et al. (Jul. 31, 2001). "Human TLR9 Confers Responsiveness to Bacterial DNA via Species-Specific CpG Motif Recognition," *Proc. Natl. Acad. Sci. USA* 98(16):9237-9242.

Beaucage, S.L. (1993). "Oligodeoxyribonucleotide Synthesis," Chapter 3 in *Protocols for Oligonucleotides and Analogs: Synthesis and Properties*, vol. 20, Agrawal, S. ed., Humana Press: Totowa, NJ, pp. 33-61.

Benoit, R. et al. (1987). "Peptides: Strategies for Antibody Production and Radioimmunoassays," *Neuromethods* 6:43-72.

Bischoff, R. et al. (1987). "Introduction of 5'-Terminal Functional Groups into Synthetic Oligonucleotides for Selective Immobilization," *Anal. Biochem.* 164:336-344.

Blanks, R. et al. (1988). "An Oligodeoxynucleotide Affinity Column for the Isolation of Sequence Specific DNA Binding Proteins," *Nucleic Acids Res.* 16(21):10283-10299.

Borel, H. et al. (1990). "A Novel Technique to Link Either Proteins or Peptides to Gammaglobulin to Construct Tolerogens," *J. Immunol. Methods* 126:159-168.

Borel, Y. et al. (1995). "Food Allergens Transformed into Tolerogens," *Int. Arch. Allergy Immunol.* 107:264-267.

Borel, Y. et al. (1996). "Parenteral and Oral Administration of Tolerogens: Protein-IgG Conjugates," *Ann. N.Y. Acad. Sci.* 778:80-87.

Boujrad, N. et al. (Jun. 1993). "Inhibition of Hormone-Stimulated Steroidogenesis in Cultured Leydig Tumor Cells by a Cholesterol-Linked Phosphorothioate Oligodeoxynucleotide Antisense to Diazepam-Binding Inhibitor," *Proc. Natl. Acad. Sci. USA* 90:5728-5731.

Bousquet, Y. et al. (1999). "Molecular Mechanism of the Adsorption of a Model Protein (Human Serum Albumin) on Poly(Methylidene Malonate 2.1.2) Nanoparticles," *Pharm. Res.* 16(1):141-147.

Chaturvedi, S. et al. (1996). "Stabilization of Triple-Stranded Oligonucleotide Complexes: use of Probes Containing Alternating Phosphodiester and Stereo-Uniform Cationic Phosphoramidate Linkages," *Nucleic Acids Res.* 24(12):2318-2323.

Chavany, C. et al. (1992). "Polyalkylcyanoacrylate Nanoparticles as Polymeric Carriers for Antisense Oligonucleotides," *Pharm. Res.* 9(4):441-449.

Chavany, C. et al. (1994). "Adsorption of Oligonucleotides onto Polyisohexylcyanoacrylate Nanoparticles Protects Them Against Nucleases and Increases Their Cellular Uptake," *Pharm. Res.* 11(9):1370-1378.

Cload, S.T. et al. (1991). "Polyether Tethered Oligonucleotide Probes," *J. Am. Chem. Soc.* 113:6324-6326.

Connolly, B.A. (1985). "Chemical Synthesis of Oligonucleotides Containing a Free Sulphydryl Group and Subsequent Attachment of Thiol Specific Probes," *Nucleic Acids Res.* 13(12):4485-4502.

Connolly, B.A. (1987). "The Synthesis of Oligonucleotides Containing a Primary Amino Group at the 5'-terminus," *Nucleic Acids Res.* 15(7):3131-3139.

Corey, D.R. et al. (Dec. 4, 1987). "Generation of a Hybrid Sequence-Specific Single-Stranded Deoxyribonuclease," *Science* 238:1401-1403.

Cowdery, J.S. et al. (1996). "Bacterial DNA Induces NK Cells to Produce IFN-γ in Vivo and Increases the Toxicity of Lipopolysaccharides," *J. Immunol.* 156:4570-4575.

Dagneaux, C. et al. (1996). "Parallel and Antiparallel A*A-T Intramolecular Triple Helices," *Nucleic Acids Res.* 24(22):4506-4512.

Deng, G-M. et al. (Jun. 1999). "Intra-Articularly Localized Bacterial DNA Containing CpG Motifs Induces Arthritis," *Nature Med.* 5(6):702-705.

Diebold, S.S. et al. (Mar. 5, 2004). "Innate Antiviral Responses by Means of TLR7-mediated Recognition of Single-stranded RNA," *Science* 303:1529-1531.

Douglas, S.J. et al. (1987). "Nanoparticles in Drug Delivery," *Crit. Rev. Ther. Drug. Carrier Syst.* 3(3):233-261.

Dumas, V. et al. (1995). "Induction of Tolerance by Administration of Hapten-Immunoglobulin Conjugates is Associated with Decreased IL-2 and IL-4 Production," *Arch. Dematol. Res.* 287:123-128.

Duramad, O. et al. (Dec. 15, 2003). "IL-10 Regulates Plasmacytoid Dendritic Cell Response to CpG-Containing Immunostimulatory Sequences," *Blood* 102(13):4487-4492.

Duramad, O. et al. (May 2005). "Inhibitors of TLR-9 Act on Multiple Cell Subsets in Mouse and Man in Vitro and Prevent Death in Vivo From Systemic Inflammation," *J. Immun.* 174(9):5193-5200.

Durand, M. et al. (1990). "Circular Dichroism Studies of an Oligodeoxyribonucleotide Containing a Hairpin Loop Made of a Hexaethylene Glycol Chain: Conformation and Stability," *Nucleic Acids Res.* 18(21):6353-6359.

Gao, H. et al. (1995). "Circularization of Oligonucleotides by Disulfide Bridge Formation," *Nucleic Acids Res.* 23(11):2025-2029.

Geoghegan, K.F. et al. (1992). "Site-Directed Conjugation of Nonpeptide Groups to Peptides and Proteins via Periodate Oxidation of a 2-Amino Alcohol. Application to Modification at N-Terminal Serine," *Bioconjug. Chem.* 3:138-146.

Gnanou, Y. et al. (1988). "Synthesis of Star-Shaped Poly(ethylene oxide)," *Makromol. Chem.* 189:2885-2892.

Godard, G. et al. (1995). "Antisense Effects of Cholesterol-Oligodeoxynucleotide Conjugates Associated with Poly(alkylcyanoacrylate) Nanoparticles," *Eur. J. Biochem.* 232:404-410.

Goodchild, J. (May/Jun. 1990). "Conjugates of Oligonucleotides and Modified Oligonucleotides: A Review of Their Synthesis and Properties," *Bioconjug. Chem.* 1(3):165-187.

Grabarek, Z. et al. (1990). "Zero-Length Crosslinking Procedure with the Use of Active Esters," *Anal. Biochem.* 185:131-135.

Hagiwara, A. et al. (1987). "A New Drug—Delivery—System of Anticancer Agents: Activated Carbon Particles Adsorbing Anticancer Agents," In Vivo 1:241-252.

Haralambidis, J. et al. (1990). "The Preparation of Polyamide-Oligonucelotide Probes Containing Multiple Non-Radioactive Labels," *Nucleic Acids Res.* 18(3):501-505.

Haralambidis, J. et al. (1990). "The Synthesis of Polyamide-Oligonucleotide Conjugate Molecules," *Nucleic Acids Res.* 18(3):493-499.

Hartmann, G. et al. (Aug. 1999). "CpG DNA: A Potent Signal for Growth, Activation, and Maturation of Human Dendritic Cells," *Proc. Natl. Acad. Sci. USA* 96:9305-9310.

Hayashi, F. et al. (Apr. 26, 2001). "The Innate Immune Response to Bacterial Flagellin is Mediated by Toll-Like Receptor 5," *Nature* 410:1099-1103.

Heil, F. et al. (2003). "The Toll-Like Receptor 7 (TLR7)-Specific Stimulus Loxoribine Uncovers a Strong Relationship Within the TLR7, 8 and 9 Subfamily," *Eur. J. Immunol.* 33:2987-2997.

(56) References Cited

OTHER PUBLICATIONS

Heil, F. et al. (Mar. 5, 2004). "Species-Specific Recognition of Single-Stranded RNA via Toll-Like Receptor 7 and 8," *Science* 303:1526-1529.

Hemmi, H. et al. (Dec. 7, 2000). "A Toll-Like Receptor Recognizes Bacterial DNA," *Nature* 408:740-745.

Hemmi, H. et al. (Feb. 2002). "Small Anti-Viral Compounds Activate Immune Cells via the TLR7 MyD88-Dependent Signaling Pathway," *Nat. Immunol.* 3(2):196-200.

Hendry, P. et al. (1994). "Using Linkers to Investigate the Spatial Separation of the Conserved Nucleotides $A_g$ and $G_{12}$ in the Hammerhead Ribozyme," *Biochem. Biophys. Acta* 1219:405-412.

Inman, J.K. (Feb. 1975). "Thymus-Indepenent Antigens: the Preparation of Covalent, Hapten-Ficoll Conjugates," *J. Imm.* 114(2, Part. 1):704-709.

International Search Report mailed Aug. 4, 2006 for PCT Application No. PCT/US2005/030494 filed Aug. 24, 2005, 8 pages.

Iyer, R.P. et al. (Jul. 20, 1990). "The Automated Synthesis of Sulfur-Containing Oligonucleotides Using 3H-1,2,Benzodithiol-3-One 1,1-Dioxide as a Sulfur-Transfer Agent," *J.Org. Chem.* 55(15):4693-4699.

Jäger, A. et al. (1988). "Oligonucleotide N-Akylphosphoroamidates: Synthesis and Binding to Polynucleotides," *Biochem.* 27:7247-7246.

Jäschke, A. et al. (1993). "Automated Incorporation of Polyethylene Glycol into Synthetic Oligonucleotides," *Tetrahedron Lett.* 34(2):301-304.

Jurk, M. et al. (Jun. 2002). "Human TLR7 or TLR8 Independently Confer Responsiveness to the Antiviral Compound R-848," *Nat. Immunol.* 3(6):499.

Kandimalla, E.R. et al. (2001). "Effect of Chemical Modifications of Cytosine and Guanine in a CpG-Motif of Oligonucleotides: Structure-Immunostimulatory Activity Relationships," *Bioorg. Med. Chem.* 9:807-813.

Kessler, C. (1992) "Nonradioactive Labeling Methods for Nucleic Acids," Chapter 2 in *Nonisotopic DNA Probe Techniques*, Kricka, L.J. ed., Academic Press: San Diego, CA, pp. 29-92.

Klinman, D.M. et al. (1997). "Contribution of CpG Motifs to the Immunogenicity of DNA Vaccines," *J. Immunol.* 158:3635-3639.

Klinman, D.M. et al. (2003). "Regulation of CpG-Induced Immune Activation by Suppressive Oligonucelotides," *Annals of the New York Academy of Sciences* 1002:112-123.

Kremsky, J.N. et al. (1987). "Immobilization of DNA via Oligonucleotides Containing an Aldehyde or Carboxylic Acid Group at the 5' Terminus," *Nucleic Acids Res.* 15(7):2891-2909.

Krieg, A.M. et al. (Apr. 6, 1995). "CpG Motifs in Bacterial DNA Trigger Direct B-Cell Activation," *Nature* 374:546-549.

Lambert, G. et al. (1998). "Effect of Polyisobutylcyanoacrylate Nanoparticles and Lipofection® Loaded with Oligonucleotides on Cell Viability and PKCα Neosynthesis in HepG2 Cells," *Biochimie* 80:969-976.

Leadbetter, E.A. et al. (Apr. 11, 2002). "Chromatin-IgG Complexes Activate B Cells by Dual Engagement of IgM and Toll-like Receptors," *Nature* 416:603-607.

Lee, A.C.J. et al. (1980). "A Method for Preparing β-hCG COOH Peptide-Carrier Conjugates of Predictable Composition," *Mol. Imm.* 17:749-756.

Lee, J. et al. (May 27, 2003). "Molecular Basis for the Immunostimulatory Activity of Guanine Nucleoside Analogs: Activation of Toll-Like Receptor 7," *Proc. Natl. Acad. Sci. USA* 100(11):6646-6651.

Lenert, P. et al. (Aug. 2001). "CpG Stimulation of Primary Mouse B Cells Is Blocked by Inhibitory Oligodeoxyribonucleotides at a Site Proximal to NF-κB Activation," *Antisense & Nucleic Acid Drug Development* 11(4):247-256.

Li, S.F.Y. (1992). Chapter 5 in *Capillary Electrophoresis: Principles, Practice and Application*, Journal of Chromotography Library, vol. 52, Elsevier Science Publishers: Amsterdam, The Netherlands, pp. 202-206.

Ma, M.Y.-X. et al. (1993). "Design and Synthesis of RNA Miniduplexes via a Synthetic Linker Approach. 2. Generation of Covalently Closed, Double-Stranded Cyclic HIV-1 TAR RNA Analogs with High Tat-Binding Affinity," *Nucleic Acids Res.* 21(11):2585-2589.

Ma, M.Y.-X. et al. (1993). "Design and Synthesis of RNA Miniduplexes via a Synthetic Linker Approach," *Biochemistry* 32:1751-1758.

Marshall, J.D. et al. (Jun. 2003). "Identification of a Novel CpG DNA Class and Motif that Optimally Stimulate B Cell and Plasmacytoid Dendritic Cell Functions," *J. Leukoc. Biol.* 73:781-792.

McCurdy, S. et al. (1991). "Deoxyoligonucleotides with Inverted Polarity: Synthesis and Use in Triple-Helix Formation," *Nucleosides & Nucleotides* 10(1-3):287-290.

Miller, P.S. et al. (Dec. 1, 1971). "Synthesis and Properties of Adenine and Thymine Nucleoside Alkyl Phosphortriesters, the Neutral Analogs of Dinucleoside Monophosphates," *JACS* 93(24):6657-6665.

Nelson, J.S. et al. (1996). "Incorporation of a Non-Nucleotide Bridge into Hairpin Oligonucleotides Capable of High-Affinity Binding to the Rev Protein of HIV-1," *Biochemistry* 35(16):5339-5344.

Nelson, J.S. et al. (1997). "N3'→P5' Oligodeoxyribonucleotide Phosphoramidates: A New Method of Synthesis Based on a Phosphoramidite Amine-Exchange Reaction," *J. Org. Chem.* 62:7278-7287.

Nelson, P.S. et al. (1989). "A New and Versatile Reagent for Incorporating Multiple Primary Aliphatic Amines into Synthetic Oligonucleotides," *Nucleic Acids Res.* 17(18):7179-7186.

O'Shannessy, D.J. et al. (1985). "Specific Conjugation Reactions of the Oligosaccharide Moieties of Immunoglobulins," *J. Applied Biochem.* 7:347-355.

Ono, A. et al. (1991). "DNA Triplex Formation of Oligonucleotide Analogues Consisting of Linker Groups and Octamer Segments That Have Opposite Sugar-Phosphate Backbone Polarities," *Biochemistry* 30(41):9914-9921.

Ozinsky, A. et al. (2000). "Co-Operative Induction of Pro-Inflammatory Signaling by Toll-Like Receptors," *J. Endotoxin Res.* 6(5):393-396.

Ozinsky, A. et al. (Dec. 5, 2000). "The Repertoire for Pattern Recognition of Pathogens by the Innate Immune System is Defined by Cooperation Between Toll-Like Receptors," *Proc. Natl. Acad. Sci. USA* 97(25):13766-13771.

Peyrottes, S. et al. (1996). "Oligodeoxynucleoside Phosphoramidates (P-$NH_2$): Synthesis and Thermal Stability of Duplexes with DNA and RNA Targets," *Nucleic Acids Res.* 24(10):1841-1848.

Pisetsky, D.S. (Jan. 15, 1996). "The Immunologic Properties of DNA," *J. Immunol.* 156(2):421-423.

Poltorak, A. et al. (Dec. 11, 1998). "Defective LPS Signaling in C3H/HeJ and C57BL/10ScCr Mice: Mutations in *Tlr4* Gene," *Science* 282:2085-2088.

Rein, D. et al. (1993). "New Developments in Synthesis of Star Polymers with Poly(ethylene oxide) Arms," *Acta Polymer* 44:225-229.

Reynolds, M.A. et al. (1996). "Antisense Oligonucleotides Containing an Internal Non-Nucleotide-Based Linker Promote Site-Specific Cleavage of RNA," *Nucleic Acids Res.* 24(4):760-765.

Richardson, P.L. et al. (1991). "Tethered Oligonucleotide Probes. A Strategy for the Recognition of Structured RNA," *J. Am. Chem. Soc.* 113(13):5109-5111.

Roget, A. et al. (1989). "Synthesis and Use of Labelled Nucleoside Phosphoramidite Building Blocks Bearing a Reporter Group: Biotinyl, Dinitrophenyl, Pyrenyl and Dansyl," *Nucleic Acids Res.* 17(19):7643-7651.

Roman, M. et al. (Aug. 1997). "Immunostimulatory DNA Sequences Function as T Helper-1-Promoting Adjuvants," *Nature Med.* 3(8):849-854.

Salunkhe, M. et al. (1992). "Control of Folding and Binding of Oligonucleotides by Use of a Nonnucleotide Linker," *J. Am. Chem. Soc.* 114(23):8768-8772.

Schacht, E. et al. (Oct. 5, 1996). "Biomedical Applications of Degradable Polyphosphazenes," *Biotechnol. Bioeng.* 52(1):102-108.

Schultz, R.G. et al. (1996). "Oligo-2'-fluoro-2'-deoxynucelotide N3'→P5' Phosphoramidates: Synthesis and Properties," *Nucleic Acids Res.* 24(15):2966-2973.

(56) References Cited

OTHER PUBLICATIONS

Staros, J.V. et al. (1986). "Enhancement by N-Hydroxysulfosuccinimide of Water-Soluble Carbodiimide-Mediated Coupling Reactions," *Anal. Biochem.* 156:220-222.

Stirchak, E.P. et al. (1989). "Uncharged Stereoregular Nucleic Acid Analogs: 2. Morpholino Nucleoside Oligomers with Carbamate Internucleoside Linkages," *Nucleic Acids Res.* 17(15):6129-6141.

Stunz, L.L. et al. (2002). "Inhibitory Oligonucleotides Specifically Block Effects of Stimulatory CpG Oligonucleotides in B Cells," *European Journal of Immunology* 32:1212-1222.

Takeshita, F. et al. (2001). "Cutting Edge: Role of Toll-Like Receptor 9 in CpG DNA-Induced Activation of Human Cells," *J. Immunol.* 167:3555-3558.

Tang, J-Y. et al. (2000). "Large-Scale Synthesis of Oligonucleotide Phosphorothioates Using 3-Amino-1,2,4-dithiazole-5-thione as an Efficient Sulfur-Transfer Reagent," *Org. Process Res. Dev.* 4(3):194-198.

Tomalia, D.A. et al. (1990). "Starburst Dendrimers: Molecular-Level Control of Size, Shape, Surface Chemistry, Topology, and Flexibility from Atoms to Macroscopic Matter," *Angew. Chem. Int. Ed. Engl.* 29:138-175.

Tung, C-H. et al. (1991). "Preparation of Oligonucleotide-Peptide Conjugates," *Bioconjug. Chem.* 2(6):464-465.

Waldner, H. et al. (Apr. 2004). "Activation of Antigen-Presenting Cells by Microbial Products Breaks Self Tolerance and Induces Autoimmune Disease," *J. Clin. Invest.* 113(7):990-997.

Wang, S. et al. (1994). "Circular RNA Oligonucleotides. Synthesis, Nucleic Acid Binding Properties, and a Comparison with Circular DNAs," *Nucleic Acids Res.* 22(12):2326-2333.

Warner, B.D. et al. (Oct. 1984). "Construction and Evaluation of an Instrument for the Automated Synthesis of Oligodeoxyribonucleotides," *DNA* 3(5):401-411.

Watwe, R.M. et al. (Apr. 10, 1995). "Manufacture of Liposomes: A Review," *Curr. Sci.* 68(7):715-724.

Wyrzykiewicz, T.K. et al. (1994). "Efficiency of Sulfhurization in the Synthesis of Oligodeoxyribonucleotide Phosphorothioates Utilizing Various Sulfhurizing Reagents," *Bioorg. & Med. Chem. Lett.* 4(12):1519-1522.

Yamamoto, S. et al. (Jun. 15, 1992). "Unique Palindromic Sequences in Synthetic Oligonucleotides are Required to Induce INF and Augment INF-Mediated Natural Killer Activity," *J. Immunol.* 148(12):4072-4076.

Yanagawa, H. et al. (1988). "Analysis of Superhelical Structures of Nucleic Acid-Lipid Conjugates by Image Processing," *Nucleic Acids Symp. Ser.* 19:189-192.

Zon, G. (1993). "Oligonucleoside Phosphorothioates," Chapter 8 in *Methods in Molecular Biology: Protocols for Oligonucleotides and Analogs: Synthesis and Properties*, Agrawal, S. ed., Humana Press: Totowa, NJ, 20:165-189.

Zuckermann, R. et al. (1987). "Efficient Methods for Attachment of Thiol Specific Probes to the 3'-ends of Synthetic Oligodeoxyribonucleotides," *Nucleic Acids Res.* 15(13):5305-5321.

Atherton, E. et al. (Jul. 1981). "Synthesis of a 21-Residue Fragment of Human Proinsulin by the Polyamide Solid Phase Method," *Hoppe Seylers Z. Physiol. Chem.* 362:833-839.

Cook, P.D. (1990). "Making Drugs Out of Oligonucleotides: A Brief Review and Perspective," *Nucleosides & Nucleotides* 18(6&7):1141-1162.

Datta, S.K. et al. (2003). "The Therapeutic Potential of Antigen-Oligonucleotide Conjugates," *Ann. N.Y. Acad. Sci.* 1002:105-111.

Goldberg, B. et al. (2000). "Beyond Danger: Unmethylated CpG Dinucleotides and the Immunopathogensis of Disease," *Immunology Letters* 73:13-18.

Ho, P.P. et al. (2003). "An Immunomodulatory CpG Oligonucleotide for the Treatment of Autoimmunity via the Innate and Adaptive Immune Systems," *Journal of Immunology* 171:4920-4926.

International Search Report mailed Oct. 13, 2006 for PCT Application No. PCT/US2005/045433, filed Dec. 16, 2005, five pages.

Jarvis, T.C. et al. (Nov. 15, 1996). "Optimizing the Cell Efficacy of Synthetic Ribozymes: Site Selection and Chemical Modifications of Ribozymes Targeting the Proto-Oncogene *c-myb*," *Journal of Biological Chemistry* 271 (46):29107-29112.

Lambrecht, B.N. et al. (2000). "Induction of Rapid T Cell Activation, Division, and Recirculation by Intratracheal Injection of Dendritic Cells in a TCR Transgenic Model," *J. Immunol.* 164:2937-2946.

Li, W.M. et al. (2003). "Effective Induction of CF8+ T-Cell response Using CpG Oligodeoxynucleotides and HER-2/neu-Derived Peptide Co-Encapsulated in Liposomes," *Vaccine* 21:3319-3329.

Santeliz, J.V. et al. (Mar. 2002). "Amb a 1-Linked CpG Oligodeozynucleotides Reverse Established Airway Hyperresponsiveness in a Murine Model of Asthma," *Journal of Allergy Clinical Immunology* 109(3):455-462.

Schroeder, U. et al. (1998). "Efficacy of Oral Dalargin-Loaded Nanoparticle Delivery Across the Blood-Brain Barrier," *Peptides* 19(4):777-780.

Shevach, E.M. et al. (2001). "Control of T-Cell Activation by $CD4^+$ $CD25^+$ Suppressor T Cells," *Immunol. Rev.* 182:58-67.

Shirota, H. et al. (2000). "Regulation of Murine Airway Eosinophilia and TH2 Cells by Antigen-Conjugated CPG Oligonucleotides as a Novel Antigen-Specific Immunomodulator," *Journal of Immunology* 164:5575-5582.

Walker, L.S.K. et al. (Jan. 2002). "The Enemy Within: Keeping Self-reactive T Cells at bay in the Periphery," *Nat. Rev. Immunol.* 2:11-19.

Yamada, H. et al. (2002). "Effect of Suppressive DNA on CpG-Induced Immune Activation," *Journal of Immunology* 169:5590-5594.

International Search Report mailed on Sep. 14, 2009, or PCT Patent Application No. PCT/US2008/012220, filed on Oct. 27, 2008, 7 pages.

International Preliminary Report on Patentability mailed on May 6, 2010, for PCT Patent Application No. PCT/US2008/012220, filed on Oct. 27, 2008, 13 pages.

Wang, Y. et al. (1991). "Multinuclear Nuclear Magnetic Resonance Studies of Na Cation-Stabilized Complex Formed by d(G-G-T-T-T-T-C-G-G) in Solution. Implications for G-tetrad Structures," *J. Mol. Biol.* 222:819-832.

Bowie, J.U. et al. (Mar. 16, 1990). "Deciphering the Message in Protein Sequences: Tolerance to Amino Acid Substitutions," *Science* 247:1306-1310.

Extended European Search Report mailed on Jul. 22, 2011, for EP Patent Application No. 11155868.0, filed on Oct. 27, 2008, 9 pages.

Puig, M. et al. (2006, e-pub. Nov. 27, 2006). "Use of Thermolytic Protective Groups to Prevent G-Tetrad Formation in CpG ODN Type D: Structural Studies and Immunomodulatory Activity in Primates," *Nucleic Acids Research* 34(22):6488-6495.

Wang, Y. et al. (Dec. 15, 1994). "Solution Structure of the *Tetrahymena* Telomeric Repeat $d(T_2G_4)_4$ G-Tetraplex," *Structure* 2(12):1141-1156.

* cited by examiner

Loxoribine (TLR7)
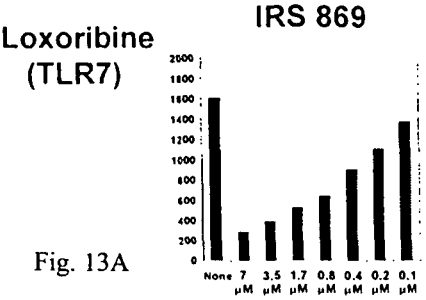
Fig. 13A
Fig. 13B
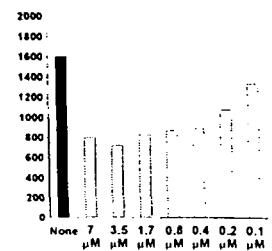
IL-6
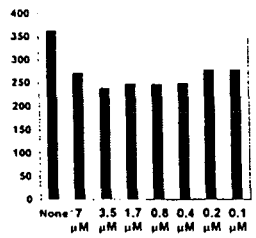
Fig. 13C
IL-12
Fig. 13D
R848 (TLR7/8)
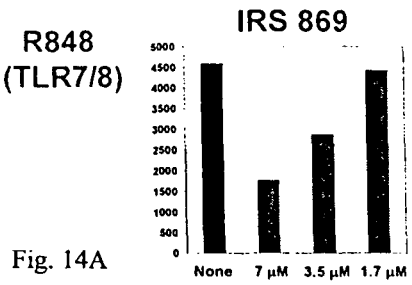
Fig. 14A
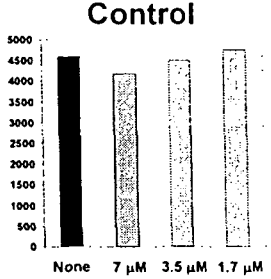
IL-6
Fig. 14B
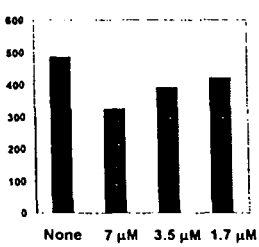
Fig. 14C
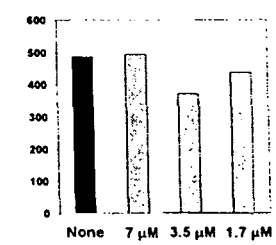
IL-12
Fig. 14D

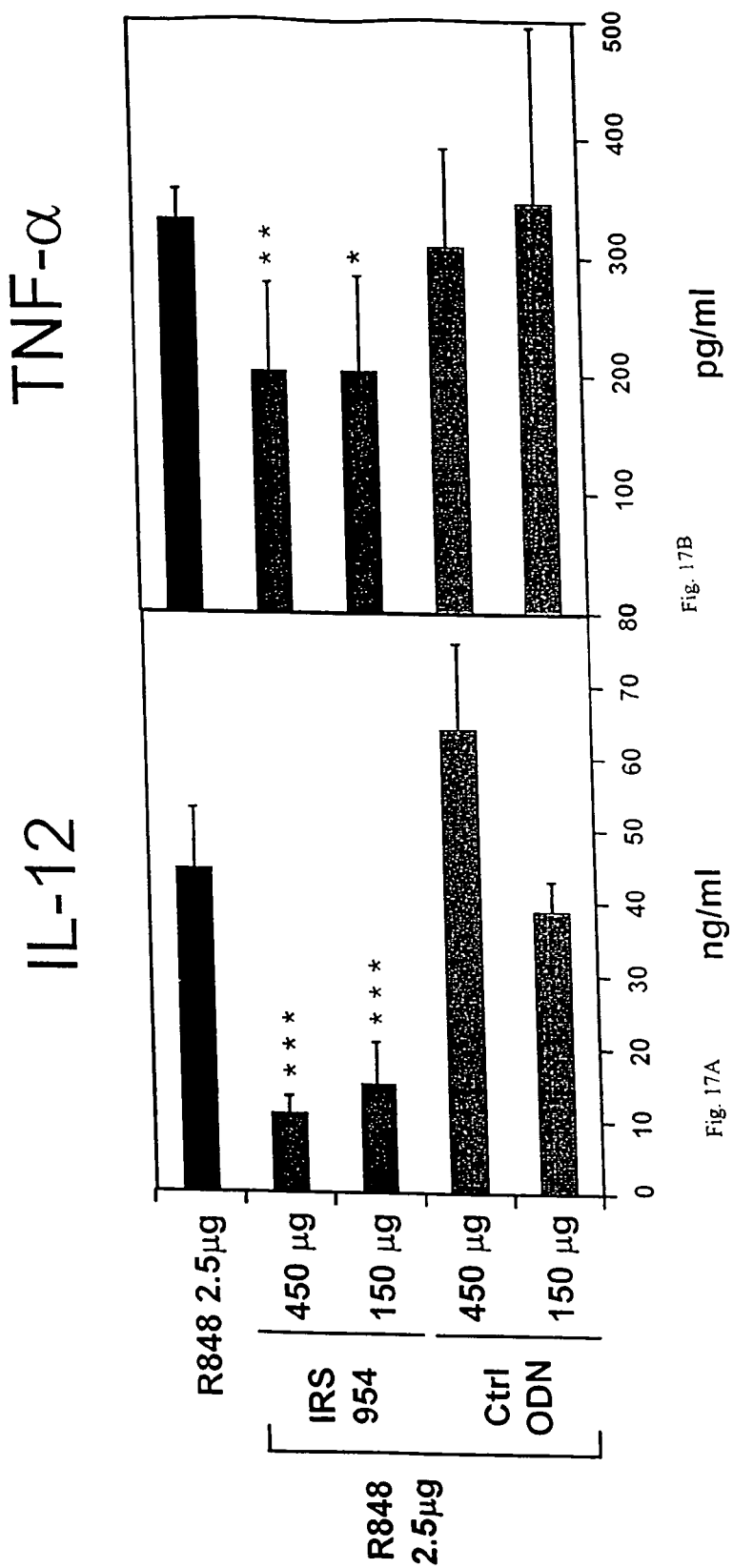

SEQUENCE LISTING

```
<160> NUMBER OF SEQ ID NOS: 123

<210> SEQ ID NO 1
<211> LENGTH: 7
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A, T, C or G
<220> FEATURE:
<221> NAME/KEY: misc_feature
<222> LOCATION: 6,7
<223> OTHER INFORMATION: n = A, T, C or G and if base at position 1 is C
      or A then bases at positions 6 and 7 cannot both be A

<400> SEQUENCE: 1 ngggg nn                                                                 7

<210> SEQ ID NO 2
<211> LENGTH: 7
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A or C
<220> FEATURE:
<221> NAME/KEY: misc_feature
<222> LOCATION: 6,7
<223> OTHER INFORMATION: n = A, T, C or G, but bases at positions 6 and
      7 cannot both be A

<400> SEQUENCE: 2 ngggg nn                                                                 7

<210> SEQ ID NO 3
<211> LENGTH: 109
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 3
<223> OTHER INFORMATION: n = A, T, C or G
<220> FEATURE:
<221> NAME/KEY: misc_feature
<222> LOCATION: (4)...(102)
<223> OTHER INFORMATION: n = absent or A, T, C or G
<220> FEATURE:
<221> NAME/KEY: misc_feature
<222> LOCATION: 103
<223> OTHER INFORMATION: n = A, T, C or G
<220> FEATURE:
<221> NAME/KEY: misc_feature
<222> LOCATION: 108,109
<223> OTHER INFORMATION: n = A, T, C or G and if base at position 103 is
      A or C then bases at positions 108 and 109 cannot
      both be A
```

<400> SEQUENCE: 3
ggnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnngggg nn                 109

<210> SEQ ID NO 4
<211> LENGTH: 132
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1
<223> OTHER INFORMATION: n = A, T, C or G
<220> FEATURE:
<221> NAME/KEY: misc_feature
<222> LOCATION: (2)...(50)
<223> OTHER INFORMATION: n = absent or A, T, C or G
<220> FEATURE:
<221> NAME/KEY: misc_feature
<222> LOCATION: 54
<223> OTHER INFORMATION: n = A, T, C or G
<220> FEATURE:
<221> NAME/KEY: misc_feature
<222> LOCATION: (55)...(103)
<223> OTHER INFORMATION: n = absent or A, T, C or G
<220> FEATURE:
<221> NAME/KEY: misc_feature
<222> LOCATION: 104,105
<223> OTHER INFORMATION: n = sequence absent or G
<220> FEATURE:
<221> NAME/KEY: misc_feature
<222> LOCATION: 106
<223> OTHER INFORMATION: n = A, T, C or G
<220> FEATURE:
<221> NAME/KEY: misc_feature
<222> LOCATION: (107)...(125)
<223> OTHER INFORMATION: n = absent or A, T, C or G
<220> FEATURE:
<221> NAME/KEY: misc_feature
<222> LOCATION: 126
<223> OTHER INFORMATION: n = A, T, C or G
<220> FEATURE:
<221> NAME/KEY: misc_feature
<222> LOCATION: 131,132
<223> OTHER INFORMATION: n = A, T, C or G and if base at position 126 is
      A or C then bases at positions 131 and 132 cannot
      both be A

<400> SEQUENCE: 4
nnnnnnnnnn nnnnnnnnnn nnnnnnnnnn nnnnnnnnnn nnnnnnnnnn tccnnnnnnn      60
nnnnnnnnnn nnnnnnnnnn nnnnnnnnnn nnnnnnnnnn nnnnnnnnnn nnnnnnnnnn     120
nnnnnngggg nn                                                          132

<210> SEQ ID NO 5
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 1,2
<223> OTHER INFORMATION: n = A, T, C or G and if base at position 3 is
      C or A then bases at positions 1 and 2 cannot both be
      G
<220> FEATURE:
<221> NAME/KEY: misc_feature
<222> LOCATION: 3
<223> OTHER INFORMATION: n = A, T, C or G

<400> SEQUENCE: 5

-continued

```
nnngggaa                                                                  9

<210> SEQ ID NO 6
<211> LENGTH: 118
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(103)
<223> OTHER INFORMATION: n = absent or A, T, C or G

<400> SEQUENCE: 6
tgcnnnnnnn nnnnnnnnnn nnnnnnnnnn nnnnnnnnnn nnnnnnnnnn nnnnnnnnnn   60
nnnnnnnnnn nnnnnnnnnn nnnnnnnnnn nnnnnnnnnn nnntcctgga ggggttgt     118

<210> SEQ ID NO 7
<211> LENGTH: 17
<212> TYPE: DNA
<213> ORGANISM: Artificial Sequence
<220> FEATURE:
<223> OTHER INFORMATION: Synthetic construct

<400> SEQUENCE: 7
ttgacagctt gacagca                                                       17

<210> SEQ ID NO 8
<211> LENGTH: 9
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 4,5
<223> OTHER INFORMATION: n = A or G
<220> FEATURE:
<221> NAME/KEY: misc_feature
<222> LOCATION: 6
<223> OTHER INFORMATION: n = A, T or G or inosine
<220> FEATURE:
<221> NAME/KEY: misc_feature
<222> LOCATION: 7
<223> OTHER INFORMATION: n = A, T, C, G or inosine and when base at
      position 6 is not G or inosine then base at position 7 is
      guanosine or inosine
<220> FEATURE:
<221> NAME/KEY: misc_feature
<222> LOCATION: 8,9
<223> OTHER INFORMATION: n = T or C

<400> SEQUENCE: 8 tgcnnnnnn                                                                 9

<210> SEQ ID NO 9
<211> LENGTH: 107
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 4,5
<223> OTHER INFORMATION: n = G or A
<220> FEATURE:
<221> NAME/KEY: misc_feature
<222> LOCATION: 6
<223> OTHER INFORMATION: n = A, T, G or inosine
<220> FEATURE:
<221> NAME/KEY: misc_feature
```

```
<222> LOCATION: 7
<223> OTHER INFORMATION: n = A, T, C, G or inosine and when base at
      position 6 is not G or inosine the base at position 7 is
      guanosine or inosine
<220> FEATURE:
<221> NAME/KEY: misc_feature
<222> LOCATION: 8,9
<223> OTHER INFORMATION: n = C or T
<220> FEATURE:
<221> NAME/KEY: misc_feature
<222> LOCATION: (10)...(107)
<223> OTHER INFORMATION: n = absent, C or T

<400> SEQUENCE: 9
tgcnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnn                    107

<210> SEQ ID NO 10
<211> LENGTH: 15
<212> TYPE: DNA
<213> ORGANISM: Artificial Sequence
<220> FEATURE:
<223> OTHER INFORMATION: Synthetic construct

<400> SEQUENCE: 10
tcctaacggg gaagt                                                       15

<210> SEQ ID NO 11
<211> LENGTH: 15
<212> TYPE: DNA
<213> ORGANISM: Artificial Sequence
<220> FEATURE:
<223> OTHER INFORMATION: Synthetic construct

<400> SEQUENCE: 11
tcctaagggg gaagt                                                       15

<210> SEQ ID NO 12
<211> LENGTH: 15
<212> TYPE: DNA
<213> ORGANISM: Artificial Sequence
<220> FEATURE:
<223> OTHER INFORMATION: Synthetic construct

<400> SEQUENCE: 12
tcctaacggg gttgt                                                       15

<210> SEQ ID NO 13
<211> LENGTH: 15
<212> TYPE: DNA
<213> ORGANISM: Artificial Sequence
<220> FEATURE:
<223> OTHER INFORMATION: Synthetic construct

<400> SEQUENCE: 13
tcctaacggg gctgt                                                       15

<210> SEQ ID NO 14
<211> LENGTH: 15
<212> TYPE: DNA
<213> ORGANISM: Artificial Sequence
<220> FEATURE:
<223> OTHER INFORMATION: Synthetic construct

<400> SEQUENCE: 14
tcctcaaggg gctgt                                                       15
```

```
<210> SEQ ID NO 15
<211> LENGTH: 15
<212> TYPE: DNA
<213> ORGANISM: Artificial Sequence
<220> FEATURE:
<223> OTHER INFORMATION: Synthetic construct

<400> SEQUENCE: 15
tcctcaaggg gttgt                                                          15

<210> SEQ ID NO 16
<211> LENGTH: 15
<212> TYPE: DNA
<213> ORGANISM: Artificial Sequence
<220> FEATURE:
<223> OTHER INFORMATION: Synthetic construct

<400> SEQUENCE: 16
tcctcatggg gttgt                                                          15

<210> SEQ ID NO 17
<211> LENGTH: 15
<212> TYPE: DNA
<213> ORGANISM: Artificial Sequence
<220> FEATURE:
<223> OTHER INFORMATION: Synthetic construct

<400> SEQUENCE: 17
tcctggaggg gttgt                                                          15

<210> SEQ ID NO 18
<211> LENGTH: 15
<212> TYPE: DNA
<213> ORGANISM: Artificial Sequence
<220> FEATURE:
<223> OTHER INFORMATION: Synthetic construct

<400> SEQUENCE: 18
tcctggaggg gctgt                                                          15

<210> SEQ ID NO 19
<211> LENGTH: 15
<212> TYPE: DNA
<213> ORGANISM: Artificial Sequence
<220> FEATURE:
<223> OTHER INFORMATION: Synthetic construct

<400> SEQUENCE: 19
tcctggaggg gccat                                                          15

<210> SEQ ID NO 20
<211> LENGTH: 15
<212> TYPE: DNA
<213> ORGANISM: Artificial Sequence
<220> FEATURE:
<223> OTHER INFORMATION: Synthetic construct

<400> SEQUENCE: 20
tcctggaggg gtcat                                                          15

<210> SEQ ID NO 21
<211> LENGTH: 15
<212> TYPE: DNA
<213> ORGANISM: Artificial Sequence
<220> FEATURE:
<223> OTHER INFORMATION: Synthetic construct

<400> SEQUENCE: 21
```

```
tccggaaggg gaagt                                                        15

<210> SEQ ID NO 22
<211> LENGTH: 15
<212> TYPE: DNA
<213> ORGANISM: Artificial Sequence
<220> FEATURE:
<223> OTHER INFORMATION: Synthetic construct

<400> SEQUENCE: 22
tccggaaggg gttgt                                                        15

<210> SEQ ID NO 23
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 9
<223> OTHER INFORMATION: n = 7-deaza-dG

<400> SEQUENCE: 23
tcctggagng gttgt                                                        15

<210> SEQ ID NO 24
<211> LENGTH: 22
<212> TYPE: DNA
<213> ORGANISM: Artificial Sequence
<220> FEATURE:
<223> OTHER INFORMATION: Synthetic construct

<400> SEQUENCE: 24
tgactgtagg cggggaagat ga                                                22

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
gagcaagctg gaccttccat                                                   20

<210> SEQ ID NO 26
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 14
<223> OTHER INFORMATION: n = 7-deaza-dG

<400> SEQUENCE: 26
cctcaagctt gagngg                                                       16

<210> SEQ ID NO 27
<211> LENGTH: 20
<212> TYPE: DNA
<213> ORGANISM: Artificial Sequence
<220> FEATURE:
<223> OTHER INFORMATION: Synthetic construct

<400> SEQUENCE: 27
```

-continued tgcttgcaag cttgcaagca                                          20

<210> SEQ ID NO 28
<211> LENGTH: 18
<212> TYPE: DNA
<213> ORGANISM: Artificial Sequence
<220> FEATURE:
<223> OTHER INFORMATION: Synthetic construct

<400> SEQUENCE: 28
tgcttgcaag cttgcaag                                            18

<210> SEQ ID NO 29
<211> LENGTH: 16
<212> TYPE: DNA
<213> ORGANISM: Artificial Sequence
<220> FEATURE:
<223> OTHER INFORMATION: Synthetic construct

<400> SEQUENCE: 29
tgcttgcaag cttgca                                              16

<210> SEQ ID NO 30
<211> LENGTH: 19
<212> TYPE: DNA
<213> ORGANISM: Artificial Sequence
<220> FEATURE:
<223> OTHER INFORMATION: Synthetic construct

<400> SEQUENCE: 30
gcttgcaagc ttgcaagca                                           19

<210> SEQ ID NO 31
<211> LENGTH: 18
<212> TYPE: DNA
<213> ORGANISM: Artificial Sequence
<220> FEATURE:
<223> OTHER INFORMATION: Synthetic construct

<400> SEQUENCE: 31
cttgcaagct tgcaagca                                            18

<210> SEQ ID NO 32
<211> LENGTH: 17
<212> TYPE: DNA
<213> ORGANISM: Artificial Sequence
<220> FEATURE:
<223> OTHER INFORMATION: Synthetic construct

<400> SEQUENCE: 32
ttgcaagctt gcaagca                                             17

<210> SEQ ID NO 33
<211> LENGTH: 20
<212> TYPE: DNA
<213> ORGANISM: Artificial Sequence
<220> FEATURE:
<223> OTHER INFORMATION: Synthetic construct

<400> SEQUENCE: 33
tgcttgcaag ctagcaagca                                          20

<210> SEQ ID NO 34
<211> LENGTH: 20
<212> TYPE: DNA
<213> ORGANISM: Artificial Sequence

```
<220> FEATURE:
<223> OTHER INFORMATION: Synthetic construct

<400> SEQUENCE: 34
tgcttgcaag cttgctagca                                                    20

<210> SEQ ID NO 35
<211> LENGTH: 20
<212> TYPE: DNA
<213> ORGANISM: Artificial Sequence
<220> FEATURE:
<223> OTHER INFORMATION: Synthetic construct

<400> SEQUENCE: 35
tgcttgacag cttgacagca                                                    20

<210> SEQ ID NO 36
<211> LENGTH: 20
<212> TYPE: DNA
<213> ORGANISM: Artificial Sequence
<220> FEATURE:
<223> OTHER INFORMATION: Synthetic construct

<400> SEQUENCE: 36
tgcttagcag ctatgcagca                                                    20

<210> SEQ ID NO 37
<211> LENGTH: 20
<212> TYPE: DNA
<213> ORGANISM: Artificial Sequence
<220> FEATURE:
<223> OTHER INFORMATION: Synthetic construct

<400> SEQUENCE: 37
tgcaagcaag ctagcaagca                                                    20

<210> SEQ ID NO 38
<211> LENGTH: 25
<212> TYPE: DNA
<213> ORGANISM: Artificial Sequence
<220> FEATURE:
<223> OTHER INFORMATION: Synthetic construct

<400> SEQUENCE: 38
tgcaagcttg caagcttgca agctt                                              25

<210> SEQ ID NO 39
<211> LENGTH: 21
<212> TYPE: DNA
<213> ORGANISM: Artificial Sequence
<220> FEATURE:
<223> OTHER INFORMATION: Synthetic construct

<400> SEQUENCE: 39
tgctgcaagc ttgcagatga t                                                  21

<210> SEQ ID NO 40
<211> LENGTH: 19
<212> TYPE: DNA
<213> ORGANISM: Artificial Sequence
<220> FEATURE:
<223> OTHER INFORMATION: Synthetic construct

<400> SEQUENCE: 40
tgcttgcaag cttgcaagc                                                     19
```

```
<210> SEQ ID NO 41
<211> LENGTH: 22
<212> TYPE: DNA
<213> ORGANISM: Artificial Sequence
<220> FEATURE:
<223> OTHER INFORMATION: Synthetic construct

<400> SEQUENCE: 41
tgcaagcttg caagcttgca at                                            22

<210> SEQ ID NO 42
<211> LENGTH: 14
<212> TYPE: DNA
<213> ORGANISM: Artificial Sequence
<220> FEATURE:
<223> OTHER INFORMATION: Synthetic construct

<400> SEQUENCE: 42
tgcttgcaag cttg                                                     14

<210> SEQ ID NO 43
<211> LENGTH: 20
<212> TYPE: DNA
<213> ORGANISM: Artificial Sequence
<220> FEATURE:
<223> OTHER INFORMATION: Synthetic construct

<400> SEQUENCE: 43
agcttgcaag cttgcaagca                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic construct

<400> SEQUENCE: 44
tacttgcaag cttgcaagca                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic construct

<400> SEQUENCE: 45
tgattgcaag cttgcaagca                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic construct

<400> SEQUENCE: 46
aaattgcaag cttgcaagca                                               20

<210> SEQ ID NO 47
<211> LENGTH: 15
<212> TYPE: DNA
<213> ORGANISM: Artificial Sequence
<220> FEATURE:
<223> OTHER INFORMATION: Synthetic construct

<400> SEQUENCE: 47
```

| | |
|---|---|
| tgctggaggg gttgt | 15 |

<210> SEQ ID NO 48
<211> LENGTH: 20
<212> TYPE: DNA
<213> ORGANISM: Artificial Sequence
<220> FEATURE:
<223> OTHER INFORMATION: Synthetic construct

<400> SEQUENCE: 48

| | |
|---|---|
| aaaattgacag cttgacagca | 20 |

<210> SEQ ID NO 49
<211> LENGTH: 20
<212> TYPE: DNA
<213> ORGANISM: Artificial Sequence
<220> FEATURE:
<223> OTHER INFORMATION: Synthetic construct

<400> SEQUENCE: 49

| | |
|---|---|
| tgattgacag cttgacagca | 20 |

<210> SEQ ID NO 50
<211> LENGTH: 20
<212> TYPE: DNA
<213> ORGANISM: Artificial Sequence
<220> FEATURE:
<223> OTHER INFORMATION: Synthetic construct

<400> SEQUENCE: 50

| | |
|---|---|
| tgattgacag attgacagca | 20 |

<210> SEQ ID NO 51
<211> LENGTH: 20
<212> TYPE: DNA
<213> ORGANISM: Artificial Sequence
<220> FEATURE:
<223> OTHER INFORMATION: Synthetic construct

<400> SEQUENCE: 51

| | |
|---|---|
| tgattgacag attgacagac | 20 |

<210> SEQ ID NO 52
<211> LENGTH: 18
<212> TYPE: DNA
<213> ORGANISM: Artificial Sequence
<220> FEATURE:
<223> OTHER INFORMATION: Synthetic construct

<400> SEQUENCE: 52

| | |
|---|---|
| tgctcctgga ggggttgt | 18 |

<210> SEQ ID NO 53
<211> LENGTH: 21
<212> TYPE: DNA
<213> ORGANISM: Artificial Sequence
<220> FEATURE:
<223> OTHER INFORMATION: Synthetic construct

<400> SEQUENCE: 53

| | |
|---|---|
| tgcttgtcct ggagggggttg t | 21 |

<210> SEQ ID NO 54
<211> LENGTH: 24
<212> TYPE: DNA
<213> ORGANISM: Artificial Sequence

```
<220> FEATURE:
<223> OTHER INFORMATION: Synthetic construct

<400> SEQUENCE: 54
tgcttgacat cctggagggg ttgt                                          24

<210> SEQ ID NO 55
<211> LENGTH: 33
<212> TYPE: DNA
<213> ORGANISM: Artificial Sequence
<220> FEATURE:
<223> OTHER INFORMATION: Synthetic construct

<400> SEQUENCE: 55
tgcttgacag cttgacagtc ctggaggggt tgt                                33

<210> SEQ ID NO 56
<211> LENGTH: 30
<212> TYPE: DNA
<213> ORGANISM: Artificial Sequence
<220> FEATURE:
<223> OTHER INFORMATION: Synthetic construct

<400> SEQUENCE: 56
tgcttgacag cttgatcctg gaggggttgt                                    30

<210> SEQ ID NO 57
<211> LENGTH: 27
<212> TYPE: DNA
<213> ORGANISM: Artificial Sequence
<220> FEATURE:
<223> OTHER INFORMATION: Synthetic construct

<400> SEQUENCE: 57
tgcttgacag cttcctggag gggttgt                                       27

<210> SEQ ID NO 58
<211> LENGTH: 30
<212> TYPE: DNA
<213> ORGANISM: Artificial Sequence
<220> FEATURE:
<223> OTHER INFORMATION: Synthetic construct

<400> SEQUENCE: 58
tgcttgacag cttgctcctg gaggggttgt                                    30

<210> SEQ ID NO 59
<211> LENGTH: 33
<212> TYPE: DNA
<213> ORGANISM: Artificial Sequence
<220> FEATURE:
<223> OTHER INFORMATION: Synthetic construct

<400> SEQUENCE: 59
tgcttgacag cttgcttgtc ctggaggggt tgt                                33

<210> SEQ ID NO 60
<211> LENGTH: 35
<212> TYPE: DNA
<213> ORGANISM: Artificial Sequence
<220> FEATURE:
<223> OTHER INFORMATION: Synthetic construct

<400> SEQUENCE: 60
tgcttgacag cttgacagca tcctggaggg gttgt                              35
```

<210> SEQ ID NO 61
<211> LENGTH: 35
<212> TYPE: DNA
<213> ORGANISM: Artificial Sequence
<220> FEATURE:
<223> OTHER INFORMATION: Synthetic construct

<400> SEQUENCE: 61
tgcttgacag cttgacagca tcctggaggg gttgt            35

<210> SEQ ID NO 62
<211> LENGTH: 32
<212> TYPE: DNA
<213> ORGANISM: Artificial Sequence
<220> FEATURE:
<223> OTHER INFORMATION: Synthetic construct

<400> SEQUENCE: 62
tgcttgacag cttgacagca tcctggaggg gt               32

<210> SEQ ID NO 63
<211> LENGTH: 31
<212> TYPE: DNA
<213> ORGANISM: Artificial Sequence
<220> FEATURE:
<223> OTHER INFORMATION: Synthetic construct

<400> SEQUENCE: 63
tgcttgacag cttgacagca tcctggaggg g                31

<210> SEQ ID NO 64
<211> LENGTH: 30
<212> TYPE: DNA
<213> ORGANISM: Artificial Sequence
<220> FEATURE:
<223> OTHER INFORMATION: Synthetic construct

<400> SEQUENCE: 64
tgcttgcaag cttgctcctg gagggttgt                   30

<210> SEQ ID NO 65
<211> LENGTH: 27
<212> TYPE: DNA
<213> ORGANISM: Artificial Sequence
<220> FEATURE:
<223> OTHER INFORMATION: Synthetic construct

<400> SEQUENCE: 65
tgcttgcaag cttcctggag gggttgt                     27

<210> SEQ ID NO 66
<211> LENGTH: 35
<212> TYPE: DNA
<213> ORGANISM: Artificial Sequence
<220> FEATURE:
<223> OTHER INFORMATION: Synthetic construct

<400> SEQUENCE: 66
tgcttgcaag cttgcaagca tcctggaggg gttgt            35

<210> SEQ ID NO 67
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature

```
<222> LOCATION: 20,21
<223> OTHER INFORMATION: Bases at positions 20 and 21 are linked by a
      hexa-(ethylene glycol) moiety

<400> SEQUENCE: 67
tgcttgcaag cttgcaagca tcctggaggg gttgt                              35

<210> SEQ ID NO 68
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 20,21
<223> OTHER INFORMATION: Bases at positions 20 and 21 are linked by a
      hexa-(ethylene glycol) moiety

<400> SEQUENCE: 68
tgcttgcaag ctagcaagca tcctggaggg gttgt                              35

<210> SEQ ID NO 69
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 20,21
<223> OTHER INFORMATION: Bases at positions 20 and 21 are linked by a
      hexa-(ethylene glycol) moiety

<400> SEQUENCE: 69
tgcttgcaag cttgctagca tcctggaggg gttgt                              35

<210> SEQ ID NO 70
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 20,21
<223> OTHER INFORMATION: Bases at positions 20 and 21 are linked by a
      hexa-(ethylene glycol) moiety
<220> FEATURE:
<221> NAME/KEY: misc_feature
<222> LOCATION: 29
<223> OTHER INFORMATION: n = 7-deaza-dG

<400> SEQUENCE: 70
tgcttgcaag cttgctagca tcctggagng gttgt                              35

<210> SEQ ID NO 71
<211> LENGTH: 35
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 15,16
<223> OTHER INFORMATION: Bases at positions 15 and 16 are linked by a
      hexa-(ethylene glycol) moiety

<400> SEQUENCE: 71
tcctggaggg gttgttgctt gcaagcttgc aagca                              35
```

```
<210> SEQ ID NO 72
<211> LENGTH: 11
<212> TYPE: DNA
<213> ORGANISM: Artificial Sequence
<220> FEATURE:
<223> OTHER INFORMATION: Synthetic construct

<400> SEQUENCE: 72
tgcttgcaag c                                                              11

<210> SEQ ID NO 73
<211> LENGTH: 16
<212> TYPE: DNA
<213> ORGANISM: Artificial Sequence
<220> FEATURE:
<223> OTHER INFORMATION: Synthetic construct

<400> SEQUENCE: 73
cttgcaagct tgcaag                                                         16

<210> SEQ ID NO 74
<211> LENGTH: 12
<212> TYPE: DNA
<213> ORGANISM: Artificial Sequence
<220> FEATURE:
<223> OTHER INFORMATION: Synthetic construct

<400> SEQUENCE: 74
tgcaagcttg ca                                                             12

<210> SEQ ID NO 75
<211> LENGTH: 18
<212> TYPE: DNA
<213> ORGANISM: Artificial Sequence
<220> FEATURE:
<223> OTHER INFORMATION: Synthetic construct

<400> SEQUENCE: 75
tgctcctgca ggttaagt                                                       18

<210> SEQ ID NO 76
<211> LENGTH: 15
<212> TYPE: DNA
<213> ORGANISM: Artificial Sequence
<220> FEATURE:
<223> OTHER INFORMATION: Synthetic construct

<400> SEQUENCE: 76
tactggaggg gttgt                                                          15

<210> SEQ ID NO 77
<211> LENGTH: 15
<212> TYPE: DNA
<213> ORGANISM: Artificial Sequence
<220> FEATURE:
<223> OTHER INFORMATION: Synthetic construct

<400> SEQUENCE: 77
ttctggaggg gttgt                                                          15

<210> SEQ ID NO 78
<211> LENGTH: 18
<212> TYPE: DNA
<213> ORGANISM: Artificial Sequence
<220> FEATURE:
<223> OTHER INFORMATION: Synthetic construct
<220> FEATURE:
```

```
<221> NAME/KEY: misc_feature
<222> LOCATION: 12
<223> OTHER INFORMATION: n = 7-deaza-dG

<400> SEQUENCE: 78
tgctgctgga gnggttgt                                                   18

<210> SEQ ID NO 79
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 9
<223> OTHER INFORMATION: n = 7-deaza-dG

<400> SEQUENCE: 79
tgctggagng gttgt                                                      15

<210> SEQ ID NO 80
<211> LENGTH: 22
<212> TYPE: DNA
<213> ORGANISM: Artificial Sequence
<220> FEATURE:
<223> OTHER INFORMATION: Synthetic construct

<400> SEQUENCE: 80
tgactgtgaa ccttagagat ga                                              22

<210> SEQ ID NO 81
<211> LENGTH: 15
<212> TYPE: DNA
<213> ORGANISM: Artificial Sequence
<220> FEATURE:
<223> OTHER INFORMATION: Synthetic construct

<400> SEQUENCE: 81
gctagagctt aggct                                                      15

<210> SEQ ID NO 82
<211> LENGTH: 20
<212> TYPE: DNA
<213> ORGANISM: Artificial Sequence
<220> FEATURE:
<223> OTHER INFORMATION: Synthetic construct

<400> SEQUENCE: 82
gcggcgggcg gcgcgcgccc                                                 20

<210> SEQ ID NO 83
<211> LENGTH: 20
<212> TYPE: DNA
<213> ORGANISM: Artificial Sequence
<220> FEATURE:
<223> OTHER INFORMATION: Synthetic construct

<400> SEQUENCE: 83
gcgcgcgcgc gcgcgcgcgc                                                 20

<210> SEQ ID NO 84
<211> LENGTH: 20
<212> TYPE: DNA
<213> ORGANISM: Artificial Sequence
<220> FEATURE:
<223> OTHER INFORMATION: Synthetic construct
```

<400> SEQUENCE: 84
ccggccggcc ggccggccgg                                              20

<210> SEQ ID NO 85
<211> LENGTH: 22
<212> TYPE: DNA
<213> ORGANISM: Artificial Sequence
<220> FEATURE:
<223> OTHER INFORMATION: Synthetic construct

<400> SEQUENCE: 85
tgactgtgaa ggttagagat ga                                           22

<210> SEQ ID NO 86
<211> LENGTH: 16
<212> TYPE: DNA
<213> ORGANISM: Artificial Sequence
<220> FEATURE:
<223> OTHER INFORMATION: Synthetic construct

<400> SEQUENCE: 86
cctcaagctt gagggg                                                  16

<210> SEQ ID NO 87
<211> LENGTH: 24
<212> TYPE: DNA
<213> ORGANISM: Artificial Sequence
<220> FEATURE:
<223> OTHER INFORMATION: Synthetic construct

<400> SEQUENCE: 87
ttagggttag ggttagggtt aggg                                         24

<210> SEQ ID NO 88
<211> LENGTH: 24
<212> TYPE: DNA
<213> ORGANISM: Artificial Sequence
<220> FEATURE:
<223> OTHER INFORMATION: Synthetic construct

<400> SEQUENCE: 88
ttagggttag ggttagggtt aggg                                         24

<210> SEQ ID NO 89
<211> LENGTH: 16
<212> TYPE: DNA
<213> ORGANISM: Artificial Sequence
<220> FEATURE:
<223> OTHER INFORMATION: Synthetic construct

<400> SEQUENCE: 89
cctcaagctt gagggg                                                  16

<210> SEQ ID NO 90
<211> LENGTH: 15
<212> TYPE: DNA
<213> ORGANISM: Artificial Sequence
<220> FEATURE:
<223> OTHER INFORMATION: Synthetic construct

<400> SEQUENCE: 90
tcctgcaggt taagt                                                   15

<210> SEQ ID NO 91
<211> LENGTH: 15
<212> TYPE: DNA

<213> ORGANISM: Artificial Sequence
<220> FEATURE:
<223> OTHER INFORMATION: Synthetic construct

<400> SEQUENCE: 91
tcctggcggg gaagt                                                        15

<210> SEQ ID NO 92
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 9
<223> OTHER INFORMATION: n = 7-deaza-dG

<400> SEQUENCE: 92
tcctggcgng gaagt                                                        15

<210> SEQ ID NO 93
<211> LENGTH: 15
<212> TYPE: DNA
<213> ORGANISM: Artificial Sequence
<220> FEATURE:
<223> OTHER INFORMATION: Synthetic construct

<400> SEQUENCE: 93
tcctggcgag gaagt                                                        15

<210> SEQ ID NO 94
<211> LENGTH: 15
<212> TYPE: DNA
<213> ORGANISM: Artificial Sequence
<220> FEATURE:
<223> OTHER INFORMATION: Synthetic construct

<400> SEQUENCE: 94
tcctggcggg aaagt                                                        15

<210> SEQ ID NO 95
<211> LENGTH: 15
<212> TYPE: DNA
<213> ORGANISM: Artificial Sequence
<220> FEATURE:
<223> OTHER INFORMATION: Synthetic construct

<400> SEQUENCE: 95
tcctggcgga aaagt                                                        15

<210> SEQ ID NO 96
<211> LENGTH: 15
<212> TYPE: DNA
<213> ORGANISM: Artificial Sequence
<220> FEATURE:
<223> OTHER INFORMATION: Synthetic construct

<400> SEQUENCE: 96
tcctggaggg gaagt                                                        15

<210> SEQ ID NO 97
<211> LENGTH: 15
<212> TYPE: DNA
<213> ORGANISM: Artificial Sequence
<220> FEATURE:
<223> OTHER INFORMATION: Synthetic construct

```
<400> SEQUENCE: 97
tcctggcggg gaagt                                                    15

<210> SEQ ID NO 98
<211> LENGTH: 18
<212> TYPE: DNA
<213> ORGANISM: Artificial Sequence
<220> FEATURE:
<223> OTHER INFORMATION: Synthetic construct

<400> SEQUENCE: 98
tcctgctgga ggggttgt                                                 18

<210> SEQ ID NO 99
<211> LENGTH: 21
<212> TYPE: DNA
<213> ORGANISM: Artificial Sequence
<220> FEATURE:
<223> OTHER INFORMATION: Synthetic construct

<400> SEQUENCE: 99
tcgtcgaacg ttcgagatga t                                             21

<210> SEQ ID NO 100
<211> LENGTH: 17
<212> TYPE: DNA
<213> ORGANISM: Artificial Sequence
<220> FEATURE:
<223> OTHER INFORMATION: Synthetic construct

<400> SEQUENCE: 100
tgctcctgga ggggttg                                                  17

<210> SEQ ID NO 101
<211> LENGTH: 16
<212> TYPE: DNA
<213> ORGANISM: Artificial Sequence
<220> FEATURE:
<223> OTHER INFORMATION: Synthetic construct

<400> SEQUENCE: 101
tgctcctgga ggggtt                                                   16

<210> SEQ ID NO 102
<211> LENGTH: 15
<212> TYPE: DNA
<213> ORGANISM: Artificial Sequence
<220> FEATURE:
<223> OTHER INFORMATION: Synthetic construct

<400> SEQUENCE: 102
tgctcctgga ggggt                                                    15

<210> SEQ ID NO 103
<211> LENGTH: 14
<212> TYPE: DNA
<213> ORGANISM: Artificial Sequence
<220> FEATURE:
<223> OTHER INFORMATION: Synthetic construct

<400> SEQUENCE: 103
tgctcctgga gggg                                                     14

<210> SEQ ID NO 104
<211> LENGTH: 13
<212> TYPE: DNA
```

```
<213> ORGANISM: Artificial Sequence
<220> FEATURE:
<223> OTHER INFORMATION: Synthetic construct

<400> SEQUENCE: 104
tgctcctgga ggg                                                              13

<210> SEQ ID NO 105
<211> LENGTH: 12
<212> TYPE: DNA
<213> ORGANISM: Artificial Sequence
<220> FEATURE:
<223> OTHER INFORMATION: Synthetic construct

<400> SEQUENCE: 105
tgctcctgga gg                                                               12

<210> SEQ ID NO 106
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 3,4
<223> OTHER INFORMATION: Bases at positions 3 and 4 are linked by a
      hexa-(ethylene glycol) moiety

<400> SEQUENCE: 106
tgctggaggg gttgt                                                            15

<210> SEQ ID NO 107
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 3,4
<223> OTHER INFORMATION: Bases at positions 3 and 4 are linked by
      tetra-(etylene glycol)

<400> SEQUENCE: 107
tgctggaggg gttgt                                                            15

<210> SEQ ID NO 108
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 4
<223> OTHER INFORMATION: n = ddd

<400> SEQUENCE: 108
tgcntggagg ggttgt                                                           16

<210> SEQ ID NO 109
<211> LENGTH: 17
<212> TYPE: DNA
<213> ORGANISM: Artificial Sequence
<220> FEATURE:
<223> OTHER INFORMATION: Synthetic construct

<400> SEQUENCE: 109
```
gctcctggag gggttgt                                                      17

<210> SEQ ID NO 110
<211> LENGTH: 16
<212> TYPE: DNA
<213> ORGANISM: Artificial Sequence
<220> FEATURE:
<223> OTHER INFORMATION: Synthetic construct

<400> SEQUENCE: 110
ctcctggagg ggttgt                                                       16

<210> SEQ ID NO 111
<211> LENGTH: 18
<212> TYPE: DNA
<213> ORGANISM: Artificial Sequence
<220> FEATURE:
<223> OTHER INFORMATION: Synthetic construct

<400> SEQUENCE: 111
aaatcctgga ggggttgt                                                     18

<210> SEQ ID NO 112
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 7
<223> OTHER INFORMATION: n = d

<400> SEQUENCE: 112
tcctggnggg gttgt                                                        15

<210> SEQ ID NO 113
<211> LENGTH: 15
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 7
<223> OTHER INFORMATION: n = dd

<400> SEQUENCE: 113
tcctggnggg gttgt                                                        15

<210> SEQ ID NO 114
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 18
<223> OTHER INFORMATION: Two hexa-(ethylene glycol) moieties are linked to
      base at position 18

<400> SEQUENCE: 114
tgctcctgga ggggttgt                                                     18

<210> SEQ ID NO 115
<211> LENGTH: 16
<212> TYPE: DNA
<213> ORGANISM: Artificial Sequence

```
<220> FEATURE:
<223> OTHER INFORMATION: Synthetic construct
<220> FEATURE:
<221> NAME/KEY: misc_feature
<222> LOCATION: 15,16
<223> OTHER INFORMATION: Bases 15 and 16 are linked by 15 propyl linkers
      connected via phosphorothioate esters

<400> SEQUENCE: 115
tcctggaggg gttgtt                                                    16

<210> SEQ ID NO 116
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 15,16
<223> OTHER INFORMATION: Bases at positions 15 and 16 are linked by 15
      glycerol linkers connected via phosphorothioate
      esters

<400> SEQUENCE: 116
tcctggaggg gttgtt                                                    16

<210> SEQ ID NO 117
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 15,16
<223> OTHER INFORMATION: Bases at positions 15 and 16 are linked by 8
      triehyleneglycol linkers connnected via
      phosphorothioate esters

<400> SEQUENCE: 117
tcctggaggg gttgtt                                                    16

<210> SEQ ID NO 118
<211> LENGTH: 16
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 15,16
<223> OTHER INFORMATION: Bases at positions 15 and 16 are linked by 4
      hexaethyleneglycol linkers connnected via
      phosophothioate esters

<400> SEQUENCE: 118
tcctggaggg gttgtt                                                    16

<210> SEQ ID NO 119
<211> LENGTH: 22
<212> TYPE: DNA
<213> ORGANISM: Artificial Sequence
<220> FEATURE:
<223> OTHER INFORMATION: Synthetic construct

<400> SEQUENCE: 119
tgactgtgaa cgttcgagat ga                                             22

<210> SEQ ID NO 120
```

```
<211> LENGTH: 53
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(53)
<223> OTHER INFORMATION: n = absent or A, T, C or G wherein n comprises
      atleast one gc dinucleotide and bases at positions
      (4)...(8) can not be absent

<400> SEQUENCE: 120
tgcnnnnnnn nnnnnnnnnn nnnnnnnnnn nnnnnnnnnn nnnnnnnnnn nnn            53

<210> SEQ ID NO 121
<211> LENGTH: 54
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(53)
<223> OTHER INFORMATION: n = absent or A, T, C or G wherein n comprises
      at least one gc dinucleotide and bases at positions
      (4)...(8) can not be absent

<400> SEQUENCE: 121
tgcnnnnnnn nnnnnnnnnn nnnnnnnnnn nnnnnnnnnn nnnnnnnnnn nnna           54

<210> SEQ ID NO 122
<211> LENGTH: 55
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(53)
<223> OTHER INFORMATION: n = absent or A, T, C or G wherein n comprises
      at least one gc dinucleotide and bases at positions
      (4)...(8) can not be absent

<400> SEQUENCE: 122
tgcnnnnnnn nnnnnnnnnn nnnnnnnnnn nnnnnnnnnn nnnnnnnnnn nnnca          55

<210> SEQ ID NO 123
<211> LENGTH: 56
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (4)...(53)
<223> OTHER INFORMATION: n = absent or A, T, C or G wherein n comprises
      at least one gc dinucleotide and bases at positions
      (4)...(8) can not be absent

<400> SEQUENCE: 123
tgcnnnnnnn nnnnnnnnnn nnnnnnnnnn nnnnnnnnnn nnnnnnnnnn nnngca         56
```

METHODS AND COMPOSITIONS FOR INHIBITION OF INNATE IMMUNE RESPONSES AND AUTOIMMUNITY

CROSS-REFERENCE TO RELATED APPLICATIONS

This application claims the benefit of U.S. Provisional Patent Application Ser. No. 60/606,833, filed Sep. 1, 2004, which is hereby incorporated by reference herein in its entirety.

TECHNICAL FIELD

The present invention relates to immunoregulatory polynucleotides. It also relates to the administration of the polynucleotides to regulate an immune response.

BACKGROUND OF THE INVENTION

Immunity can generally be classified as innate immunity or as adaptive immunity. Innate immune responses typically occur immediately upon infection to provide an early barrier to infectious disease whereas adaptive immune responses occur later with the generation of antigen-specific effector cells and often long term protective immunity. Innate immune responses do not generate lasting protective immunity but appear to play a role in the generation of the later arising adaptive immune response.

Innate immunity uses germ-line encoded receptors to recognize features that are common to many pathogens and to activate signalling events that result in the expression of effector molecules. Some of these effector molecules may eventually induce an adaptive immune response. The family of Toll-like receptors (TLRs) have been associated with innate immune response signalling and microbial ligands have been identified for several mammalian TLRs. For example, TLR2 interacts with peptidoglycan, bacterial lipopeptides and certain types of lipopolysaccharide (LPS), TLR3 interacts with double-stranded RNA, TLR4 interacts with LPS and TLR-5 interacts with bacterial flagellin. See, for example, Poltorak et al. (1998) *Science* 282:2085-2088; Akira et al. (2003) *Immunol. Lett.* 85:85-95; Alexopoulou et al. (2001) *Nature* 413: 732-738; Hayashi et al. (2001) *Nature* 410:1099-1103. TLR-7 is activated by guanosine analogs, by small antiviral compounds such as imidazoquinolines, imiquimod and R-848, and by single-stranded viral RNA and TLR-8 is also activated by R-848 and single-stranded viral RNA. See, for example, Lee et al. (2003) *Proc. Natl. Acad. Sci. USA* 100: 6646-6651; Hemmi et al. (2002) *Nat. Immunol.* 3:196-200; Jurk et al. (2002) *Nat. Immunol.* 3:499; Heil et al. (2004) *Science* 303:1526-1529; Diebold et al. (2004) *Science* 303: 1529-1531. TLR-9 has been shown to recognize immunostimulatory nucleic acid molecules such as bacterial DNA and immunostimulatory DNA containing a 5'-CG-3' sequence. See, for example, Hemmi et al. (2000) *Nature* 408:740-745; Bauer et al. (2001) *Proc. Natl. Acad. Sci. USA* 98:9237-9242; Takeshita et al. (2001) *J. Immunol.* 167:3555-3558. In addition, certain TLRs (for example, TLR-1, TLR-2 and TLR-6) can heterodimerize, interact with their microbial ligands and lead to cell activation, thus expanding the ligand repetoire of the TLR family. Ozinsky et al. (2000) *J. Endotoxin Res.* 6:393-396; Ozinsky et al. (2000) *Proc. Natl. Acad. Sci. USA* 97:13766-13771.

Immunostimulatory nucleic acid (ISNA) molecules, such as bacterial DNA or a polynucleotide containing unmethylated 5'-CG-3' sequences, can stimulate innate immune responses, such as cytokine production, and dendritic cell and macrophage activation, and then lead to a Th1-type immune response. Immunostimulatory nucleic acid molecules stimulate the immune response through interaction with and signalling through the mammalian TLR9 receptor. Hemmi et al. (2000), *Supra*. Mammalian DNA does not generally possess immunostimulatory activity due apparently to a low frequency of CG sequences and to most of the CG sequences having a methylated cytosine. Mammalian immune system cells thus appear to distinguish bacterial DNA from self DNA through the TLR9 receptor.

Immunostimulatory nucleic acid molecules have been implicated in the pathogenesis of arthritis. Immunostimulatory nucleic acid has been shown to play a role in activation of autoreactive B cells such as those produce a class of autoantibodies known as rheumatoid factor (RF). Thus, such immunostimulatory nucleic acids appear to play a role in systemic autoimmunity. In addition, immunostimulatory nucleic acid can enhance toxicity of LPS and contribute to adverse effects of administration of vectors for gene therapy. See, for example, Deng et al. (1999) *Nature Med.* 5:702-705, Leadbetter et al. (2002) *Nature* 416:603-607, Cowdery et al. (1996) *J. Immunol.* 156:4570-4575, U.S. Pat. No. 6,225,292.

There remains a need to identify strategies to control unwanted immune activation, including unwanted activation of the innate immune response.

All patents, patent applications, and publications cited herein are hereby incorporated by reference in their entirety.

DISCLOSURE OF THE INVENTION

The invention relates to immunoregulatory polynucleotides and methods for inhibiting an immune response in individuals using these polynucleotides, and particularly, methods for inhibiting an immune response in humans.

In one aspect, the invention provides immunoregulatory polynucleotides (IRP). In certain embodiments, the invention includes compositions which comprise any of the immunoregulatory polynucleotides described herein. The compositions may also include, for example, a pharmaceutically acceptable excipient or any of a number of other components.

In another aspect, the invention provides immunoregulatory compounds (IRC). In certain embodiments, the invention includes compositions which comprise any of the immunoregulatory compounds described herein. The compositions may also include, for example, a pharmaceutically acceptable excipient or any of a number of other components.

In another aspect, the invention provides methods for inhibiting an immune response comprising contacting a cell of the immune system with a polynucleotide comprising an immunoregulatory sequence (IRS), wherein the cell is contacted with the polynucleotide in an amount effective to inhibit a response from the cell that contributes to an immune response.

In another aspect, the invention provides methods of regulating an immune response in an individual, comprising administering to an individual an immunoregulatory polynucleotide or immunoregulatory compound of the invention in an amount sufficient to regulate an immune response in said individual. Immunoregulation according to the methods of the invention may be practiced on individuals including those suffering from a disorder associated with an unwanted activation of an innate immune response.

In another aspect, the invention provides methods for inhibiting a TLR7/8 dependent innate immune response in an individual, comprising administering to an individual an immunoregulatory polynucleotide or immunoregulatory compound of the invention in an amount sufficient to suppress TLR7/8 dependent cytokine production in said individual, wherein the IRP or IRC comprises an IRS of the TLR7/8 class.

In another aspect, the invention provides methods for inhibiting a TLR9 dependent innate immune response in an individual, comprising administering to an individual an immunoregulatory polynucleotide or immunoregulatory compound of the invention in an amount sufficient to suppress TLR9 dependent cytokine production in said individual, wherein the IRP or IRC comprises an IRS of the TLR9 class.

In another aspect, the invention provides methods for inhibiting a TLR9 dependent innate immune response and a TLR7/8 dependent immune response in an individual, comprising administering to an individual an immunoregulatory polynucleotide or immunoregulatory compound of the invention in an amount sufficient to suppress TLR9 dependent cytokine production and TLR7/8 dependent cytokine production in said individual, wherein the IRP or IRC comprises an IRS of the TLR7/8/9 class.

In another aspect, the invention provides methods of ameliorating one or more symptoms of an autoimmune disease, comprising administering an effective amount of an immunoregulatory polynucleotide or immunoregulatory compound of the invention to an individual having an autoimmune disease. Administration of an immunoregulatory polynucleotide or immunoregulatory compound in accordance with the invention ameliorates one or more symptoms of the autoimmune disease, including SLE and rheumatoid arthritis. In certain embodiments, the immunoregulatory polynucleotide or immunoregulatory compound effective for suppressing a symptom of SLE comprises an immunoregulatory sequence of the TLR7/8 class or TLR9 class or TLR7/8/9 class.

In another aspect, the invention provides methods of preventing or delaying development of an autoimmune disease, comprising administering an effective amount of an immunoregulatory polynucleotide or immunoregulatory compound of the invention to an individual at risk of developing an autoimmune disease. Administration of an immunoregulatory polynucleotide or immunoregulatory compound in accordance with the invention prevents or delays development of the autoimmune disease.

In another aspect, the invention provides methods of ameliorating one or more symptoms of an inflammatory disease or disorder, comprising administering an effective amount of an immunoregulatory polynucleotide or immunoregulatory compound of the invention to an individual having an inflammatory disease or disorder. Administration of an immunoregulatory polynucleotide in accordance with the invention ameliorates one or more symptoms of the inflammatory disease or disorder. In certain embodiments, the compositions of the invention are effective in ameliorating a symptom of chronic inflammatory disease or disorder.

In another aspect, the invention provides methods of suppressing chronic pathogen stimulation, comprising administering an effective amount of an immunoregulatory polynucleotide or immunoregulatory compound of the invention to an individual having a chronic pathogen infection or disease. Administration of an immunoregulatory polynucleotide or immunoregulatory compound in accordance with the invention suppresses chronic pathogen stimulation in the individual, including that associated with malaria and chronic viral infections. In certain embodiments, the immunoregulatory polynucleotide or immunoregulatory compound effective for suppressing chronic pathogen stimulation comprises an immunoregulatory sequence of the TLR7/8 class.

In some embodiments, the compositions of the invention inhibit a response of a B cell or a plasmacytoid dendritic cell. In some embodiments, immune responses inhibited by the compositions of the invention include inhibition of cytokine production, such as IL-6, IL-12, IFN-α, and/or TNF-α, by the cell, inhibition of cell maturation and/or inhibition of cell proliferation. In some embodiments, the compositions of the invention inhibit a TLR9 dependent cell response, a TLR7/8 dependent cell response, and/or a TLR7/8/9 dependent cell response.

The invention further relates to kits, preferably for carrying out the methods of the invention. The kits of the invention generally comprise an immunoregulatory polynucleotide and/or immunoregulatory compound of the invention (generally in a suitable container), and may further include instructions for use of the immunoregulatory polynucleotide and/or immunoregulatory compound in immunoregulation of an individual.

Furthermore, provided herein are oligonucleotides comprising a nucleotide sequence of the formula: $X_1GGGGX_2X_3$ (SEQ ID NO:1), wherein $X_1$, $X_2$, and $X_3$ are nucleotides, provided that if $X_1$=C or A, then $X_2X_3$ is not AA. In some examples of the oligonucleotide, $X_1$ is C or A. Provided herein are oligonucleotides comprising a nucleotide sequence of the formula:

$GGN_mX_1GGGGX_2X_3$ (SEQ ID NO:3), wherein m is an integer from 1 to about 100, or from 1 to about 20, each N is a nucleotide, and $X_1$, $X_2$, and $X_3$ are nucleotides, provided that if $X_1$=C or A, then $X_2X_3$ is not AA. In some examples of the oligonucleotide $X_1$ is C or A.

Provided herein are oligonucleotides comprising a nucleotide sequence of the formula: $N_iTCCN_j(GG)_k N_mX_1GGGGX_2X_3$ (SEQ ID NO:4), wherein each N is a nucleotide, i is an integer from 1 to about 50, j is an integer from 1 to about 50, k is 0 or 1, m is an integer from 1 to about 20, and $X_1$, $X_2$, and $X_3$ are nucleotides, provided that if $X_1$=C or A, then $X_2X_3$ is not AA. In some examples of the oligonucleotide, $X_1$ is C or A. Provided herein are oligonucleotides comprising a nucleotide sequence of the formula: $X_1X_2X_3GGGGAA$ (SEQ ID NO:5), wherein $X_1$, $X_2$, and $X_3$ are nucleotides, provided that if $X_3$=C or A, then $X_1X_2$ is not GG. In some examples of the above oligonucleotides, at least one G is replaced by Z', wherein Z'=7-deazaG.

Provided herein are oligonucleotides comprising the sequence 5'-TGCTTGCAAGCTTGCAAGCA-3' (SEQ ID NO:27 (C661) or a fragment of this sequence that includes at least a 10 base palindromic portion thereof. Provided herein are oligonucleotides consisting of the nucleotide sequence 5'-TGCNm-3' (SEQ ID NO:120), wherein each N is a nucleotide, m is an integer from 5 to about 50 and the sequence N1-Nm comprises at least one GC dinucleotide (that is, wherein the sequence Nm comprises at least one GC dinucleotide). In some examples, the oligonucleotide consists of the nucleotide sequence 5'-TGCNmA-3' (SEQ ID NO:121). In other examples, the oligonucleotide consists of the nucleotide sequence 5'-TGCNmCA-3' (SEQ ID NO:122). In other examples, the oligonucleotide consists of the nucleotide sequence 5'-TGCNmGCA-3' (SEQ ID NO:123). Provided herein are oligonucleotides comprising the nucleotide sequence TGCNmTCCTGGAGGGGTTGT-3' (SEQ ID NO:6), wherein each N is a nucleotide and m is an integer from 0 to about 100. In some examples of the oligonucleotide, the sequence N1-Nm comprises a fragment of the sequence 5'-TTGACAGCTTGACAGCA-3' (SEQ ID NO:7).

Provided herein are oligonucleotides comprising the nucleotide sequence 5'-TGCRRZNYY-3' (SEQ ID NO:8), wherein Z is any nucleotide except C, N is any nucleotide, and further wherein when Z is not G or inosine, N is guanosine or inosine. Provided herein are oligonucleotides comprising the nucleotide sequence 5'-TGCRRZNYm-3' (SEQ ID NO:9), wherein Z is any nucleotide except C, N is any nucleotide, Y is a pyrimidine nucleotide, m is an integer from 2 to 100, and wherein when Z is not G or inosine, N is guanosine or inosine.

Further, provided herein are methods of inhibiting an immune response comprising contacting a cell of the immune system with an oligonucleotide comprising a nucleotide sequence of the formula: X1GGGGX2X3 (SEQ ID NO:1), wherein X1, X2, and X3 are nucleotides, provided that if X1=C or A, then X2X3 is not AA, wherein the cell is contacted with the oligonucleotide in an amount effective to inhibit a response from the cell that contributes to an immune response. Provided herein are methods of regulating an immune response in an individual, comprising administering to an individual an oligonucleotide comprising a nucleotide sequence of the formula: X1GGGGX2X3 (SEQ ID NO:1), wherein X1, X2, and X3 are nucleotides, provided that if X1=C or A, then X2X3 is not AA, in an amount sufficient to regulate an immune response in said individual.

Provided herein are methods of regulating an immune response in an individual, comprising administering to an individual the oligonucleotide consisting of the nucleotide sequence 5'-TGCNm-3' (SEQ ID NO:120), wherein each N is a nucleotide, m is an integer from 5 to about 50 and the sequence N1-Nm comprises at least one GC dinucleotide, in an amount sufficient to regulate an immune response in said individual.

Provided herein are methods of regulating an immune response in an individual, comprising administering to an individual the oligonucleotide comprising the nucleotide sequenceTGCNmTCCTGGAGGGGTTGT-3' (SEQ ID NO:6), wherein each N is a nucleotide and m is an integer from 0 to about 100, in an amount sufficient to regulate an immune response in said individual.

Provided herein are methods of inhibiting a TLR7/8 dependent innate immune response in an individual, comprising administering to an individual the oligonucleotide consisting of the nucleotide sequence 5'-TGCNm-3' (SEQ ID NO:120), wherein each N is a nucleotide, m is an integer from 5 to about 50 and the sequence N1-Nm comprises at least one GC dinucleotide, in an amount sufficient to suppress TLR7/8 dependent cytokine production in said individual.

Provided herein are methods of inhibiting a TLR9 dependent innate immune response in an individual, comprising administering to an individual the oligonucleotide comprising a nucleotide sequence of the formula: X1GGGGX2X3 (SEQ ID NO:1), wherein X1, X2, and X3 are nucleotides, provided that if X1=C or A, then X2X3 is not AA, in an amount sufficient to suppress TLR9 dependent cytokine production in said individual.

Provided herein are methods of inhibiting a TLR9 dependent innate immune response and a TLR7/8 dependent immune response in an individual, comprising administering to an individual the oligonucleotide consisting of the nucleotide sequence 5'-TGCNm-3' (SEQ ID NO:120), wherein each N is a nucleotide, m is an integer from 5 to about 50 and the sequence N1-Nm comprises at least one GC dinucleotide, in an amount sufficient to suppress TLR9 dependent cytokine production and TLR7/8 dependent cytokine production in said individual.

Provided herein are methods of ameliorating one or more symptoms of an autoimmune disease, the method comprising administering an effective amount of the oligonucleotide comprising a nucleotide sequence of the formula: X1GGGGX2X3 (SEQ ID NO:1), wherein X1, X2, and X3 are nucleotides, provided that if X1=C or A, then X2X3 is not AA, to an individual having an autoimmune disease. In some examples, the autoimmune disease is selected from the group consisting of systemic lupus erythematosus (SLE) and rheumatoid arthritis. Provided herein are methods for ameliorating one or more symptoms of an autoimmune disease, the method comprising administering an effective amount of the oligonucleotide consisting of the nucleotide sequence 5'-TGCNm-3' (SEQ ID NO:120), wherein each N is a nucleotide, m is an integer from 5 to about 50 and the sequence N1-Nm comprises at least one GC dinucleotide, to an individual having an autoimmune disease. Provided herein are methods for ameliorating one or more symptoms of an autoimmune disease, the method comprising administering an effective amount of the oligonucleotide comprising the nucleotide sequence TGCNmTCCTGGAGGGGTTGT-3' (SEQ ID NO:6), wherein each N is a nucleotide and m is an integer from 0 to about 100 to an individual having an autoimmune disease. In some examples, the autoimmune disease is selected from the group consisting of systemic lupus erythematosus (SLE) and rheumatoid arthritis.

Provided herein are methods of preventing or delaying development of an autoimmune disease, the method comprising administering an effective amount of the oligonucleotide comprising a nucleotide sequence of the formula: X1GGGGX2X3 (SEQ ID NO:1), wherein X1, X2, and X3 are nucleotides, provided that if X1=C or A, then X2X3 is not AA, to an individual at risk of developing an autoimmune disease.

Provided herein are methods of preventing or delaying development of an autoimmune disease, the method comprising administering an effective amount of the oligonucleotide consisting of the nucleotide sequence 5'-TGCNm-3' (SEQ ID NO:120), wherein each N is a nucleotide, m is an integer from 5 to about 50 and the sequence N1-Nm comprises at least one GC dinucleotide, to an individual at risk of developing an autoimmune disease.

Provided herein are methods of preventing or delaying development of an autoimmune disease, the method comprising administering an effective amount of the oligonucleotide comprising the nucleotide sequence TGCNmTCCTG-GAGGGGTTGT-3' (SEQ ID NO:6), wherein each N is a nucleotide and m is an integer from 0 to about 100, to an individual at risk of developing an autoimmune disease.

Provided herein are methods of ameliorating one or more symptoms of an inflammatory disease or disorder, the method comprising administering an effective amount of the oligonucleotide comprising a nucleotide sequence of the formula: X1GGGGX2X3 (SEQ ID NO:1), wherein X1, X2, and X3 are nucleotides, provided that if X1=C or A, then X2X3 is not AA, to an individual having an inflammatory disease or disorder. Provided herein are methods of ameliorating one or more symptoms of an inflammatory disease or disorder, the method comprising administering an effective amount of the oligonucleotide consisting of the nucleotide sequence 5'-TGCNm-3' (SEQ ID NO:120), wherein each N is a nucleotide, m is an integer from 5 to about 50 and the sequence N1-Nm comprises at least one GC dinucleotide, to an individual having an inflammatory disease or disorder. Provided herein are methods of ameliorating one or more symptoms of an inflammatory disease or disorder, the method comprising administering an effective amount of the oligonucleotide comprising the nucleotide sequence TGCNmTCCTG-GAGGGGTTGT-3' (SEQ ID NO:6), wherein each N is a nucleotide and m is an integer from 0 to about 100, to an individual having an inflammatory disease or disorder.

Provided herein are methods of suppressing chronic pathogen stimulation, the method comprising administering an effective amount of the oligonucleotide comprising a nucleotide sequence of the formula: X1GGGGX2X3 (SEQ ID NO:1), wherein X1, X2, and X3 are nucleotides, provided that if X1=C or A, then X2X3 is not AA, to an individual having a chronic pathogen infection or disease.

Furthermore, provided herein are kits comprising:
  i. oligonucleotides comprising a nucleotide sequence of the formula: X1GGGGX2X3 (SEQ ID NO:1), wherein X1, X2, and X3 are nucleotides, provided that if X1=C or A, then X2X3 is not AA;
  ii oligonucleotides consisting of the nucleotide sequence 5'-TGCNm-3'(SEQ ID NO:120), wherein each N is a nucleotide, m is an integer from 5 to about 50 and the sequence N1-Nm comprises at least one GC dinucleotide; or
  iii. oligonucleotides comprising the nucleotide sequence TGCNmTCCTGGAGGGGTTGT-3' (SEQ ID NO:6), wherein each N is a nucleotide and m is an integer from 0 to about 100,
wherein the oligonucleotide is in a suitable container and wherein said kit comprises instructions for use of the oligonucleotide in immunoregulation of an individual.

BRIEF DESCRIPTION OF THE DRAWINGS

FIG. 1A depicts results of murine splenocytes stimulated with ISNA SEQ ID NO:119 (1018) alone and together with IRP SEQ ID NO:91 (530), IRP SEQ ID NO:17 (C869) or control C532. FIG. 1B depicts results of murine CD11c+ cells stimulated with ISNA SEQ ID NO:99 (C274) alone and together with IRP SEQ ID NO:91 (530), IRP SEQ ID NO:17 (C869) or control C532.

FIG. 9A depicts IFN-α production by murine CD11c+ splenocytes in response to HSV-1 in the presence of varying concentrations of IRP SEQ ID NO:17 (C869) or control oligonucleotide. FIG. 9B depicts IL-12 production by murine CD11c+ splenocytes in response to HSV-1 in the presence of varying concentrations of IRP SEQ ID NO:17 (C869) or control oligonucleotide. FIG. 9C depicts IFN-α production by human PDCs in response to HSV-1 in the presence of varying concentrations of IRP SEQ ID NO:17 (C869) or control oligonucleotide.

FIG. 10A depicts IFN-α production by human PDCs in response to varying amounts of influenza virus. FIG. 10B depicts IFN-α production by human PDCs in response to influenza virus in the presence of varying concentrations of IRP SEQ ID NO:17 (C869) or control oligonucleotide.

FIGS. 13A-13D depict graphs showing the effect of IRP on IL-6 (FIGS. 13A-13B) and IL-12 (FIGS. 13C-13D) production from splenocytes stimulated with loxoribine, a TLR7 stimulator. The stimulated cells were incubated with loxoribine alone and together with varying amounts of IRP SEQ ID NO:17 (C869) (FIGS. 13A-13C) or control oligonucleotide (FIGS. 13B-13D).

FIGS. 14A-14D depict graphs showing the effect of IRP on IL-6 (FIGS. 14A-14B) and IL-12 (FIGS. 14C-14D) production from splenocytes stimulated with resiquimod (R848), a TLR7/8 stimulator. The stimulated cells were incubated with R848 alone and together with varying amounts of IRP SEQ ID NO:17 (C869) (FIGS. 14A-14C) or control oligonucleotide (FIGS. 14B-14D).

FIG. 16A depicts results of murine splenocytes stimulated with ISNA SEQ ID NO:119 (1018) alone and together with IRP SEQ ID NO:17 (869), IRP SEQ ID NO:27 (661) or IRP SEQ ID NO:52 (954). FIG. 16B depicts results of murine splenocytes stimulated with R848 alone and together with IRP SEQ ID NO:17 (869), IRP SEQ ID NO:27 (661) or IRP SEQ ID NO:52 (954).

FIGS. 17A-17B is a graph showing FIG. 17A, IL-12 and FIG. 17B, TNF-α levels in serum from mice one hour after being injected with R848 alone and together with IRP SEQ ID NO:52 (954) or control oligonucleotide.

FIG. 19A depicts results of murine splenocytes stimulated with ISNA SEQ ID NO:119 (1018) alone and together with IRP SEQ ID NO:52 (954), IRP SEQ ID NO:100 (DV019: N-1), IRP SEQ ID NO:101 (DV020: N-2), IRP SEQ ID NO:102 (DV021: N-3), IRP SEQ ID NO:103 (DV022: N-4), IRP SEQ ID NO: 104 (DV023:N-5) or IRP SEQ ID NO:105 (DV024: N-6). FIG. 19B depicts results of murine splenocytes stimulated with R848 alone and together with IRP SEQ ID NO:52 (954), IRP SEQ ID NO:100 (DV019), IRP SEQ ID NO:101 (DV020), IRP SEQ ID NO: 102 (DV021), IRP SEQ ID NO:103 (DV022), IRP SEQ ID NO:104 (DV023) or IRP SEQ ID NO:105 (DV024).

MODES FOR CARRYING OUT THE INVENTION

Figure 1A:
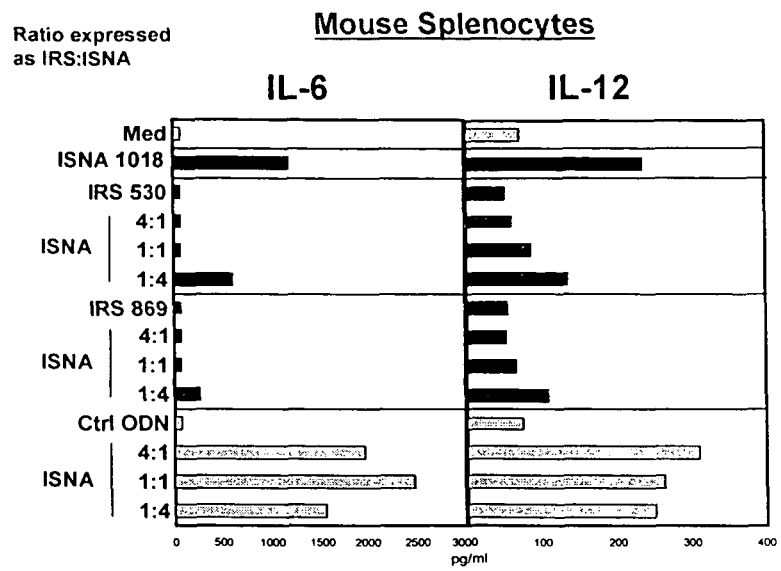
FIGS. 1A-1B are graphs showing IRP inhibition of IL-6 and IL-12 production from immunostimulatory nucleic acid (ISNA)-stimulated cells.

We have discovered immunoregulatory polynucleotides and methods of regulating immune responses in individuals, particularly humans, using these immunoregulatory polynucleotides. The compositions of the invention comprise an immunoregulatory polynucleotide as described herein. The immunoregulatory polynucleotides of the invention particularly inhibit innate immune responses, including those responses that involve signalling through TLR7/8 and/or TLR9.

We have found that immunoregulatory polynucleotides of the invention efficiently regulate immune cells, including human cells, in a variety of ways. We have observed that immunoregulatory polynucleotides of the invention can effectively suppress cytokine production, including IFN-α, IL-6, IL-12 and TNF-α, from human cells. Immunoregulatory polynucleotides of the invention suppress cell responses, including cytokine production, stimulated through TLR7/8 and/or TLR9 receptors. We have also observed that immunoregulatory polynucleotides of the invention can effectively suppress proliferation and/or maturation of cells stimulated with an immunostimulatory nucleic acid, including B cells and plasmacytoid dendritic cells. Thus, the IRP of the invention are of use in the suppression of immune responses to ISNA such as microbial DNA present due to an infection or suppression of nucleic acid vectors administered for gene therapy purposes.

The invention also provides methods of treating and preventing autoimmune disorders and chronic inflammatory disorders in an individual by administering an immunoregulatory polynucleotide of the invention to the individual.

Further provided are kits comprising the IRPs and/or IRCs of the invention. The kits may further comprise instructions for administering an immunoregulatory polynucleotide of the invention for immunoregulation in a subject.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, *Molecular Cloning: A Laboratory Manual*, second edition (Sambrook et al., 1989); *Oligonucleotide Synthesis* (M. J. Gait, ed., 1984); *Animal Cell Culture* (R. I. Freshney, ed., 1987); *Handbook of Experimental Immunology* (D. M. Weir & C.C. Blackwell, eds.); *Gene Transfer Vectors for Mammalian Cells* (J. M. Miller & M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *The Immunoassay Handbook* (D. Wild, ed., Stockton Press N.Y., 1994); *Bioconjugate Techniques* (Greg T. Hermanson, ed., Academic Press, 1996); and *Methods of Immunological Analysis* (R. Masseyeff, W. H. Albert, and N. A. Staines, eds., Weinheim: VCH Verlags gesellschaft mbH, 1993).

Definitions

As used herein, the singular form "a", "an", and "the" includes plural references unless indicated otherwise. For example, "an" IRP includes one or more IRP.

As used interchangeably herein, the terms "nucleic acid," "polynucleotide" and "oligonucleotide" include single-stranded DNA (ssDNA), double-stranded DNA (dsDNA), single-stranded RNA (ssRNA) and double-stranded RNA (dsRNA), modified oligonucleotides and oligonucleosides or combinations thereof. The oligonucleotide can be linearly or circularly configured, or the oligonucleotide can contain both linear and circular segments. Oligonucleotides are polymers of nucleosides joined, generally, through phosphodiester linkages, although alternate linkages, such as phosphorothioate esters may also be used in oligonucleotides. A nucleoside consists of a purine (adenine (A) or guanine (G) or derivative thereof) or pyrimidine (thymine (T), cytosine (C) or uracil (U), or derivative thereof) base bonded to a sugar. The four nucleoside units (or bases) in DNA are called deoxyadenosine, deoxyguanosine, deoxythymidine, and deoxycytidine. A nucleotide is a phosphate ester of a nucleoside.

The term "immunostimulatory nucleic acid" or "immunostimulatory polynucleotide" as used herein refers to a nucleic acid molecule (e.g., polynucleotide) that effects and/or contributes to a measurable immune response as measured in vitro, in vivo and/or ex vivo. Examples of measurable immune responses include, but are not limited to, antigen-specific antibody production, secretion of cytokines, activation or expansion of lymphocyte populations such as NK cells, CD4+ T lymphocytes, CD8+ T lymphocytes, B lymphocytes, and the like. Immunostimulatory nucleic acid (ISNA) sequences are known to stimulate innate immune responses, in particular, those response occur through TLR-9 signalling in the cell. As known in the art, immunostimulatory nucleic acid (ISNA) molecules can be isolated from microbial sources, such as bacteria, can be present in nucleic acid vectors for use in gene therapy, or can be synthesized using techniques and equipment described herein and known in the art. Generally, an immunostimulatory nucleic acid sequence include at least one CG dinucleotide, with the C of this dinucleotide being unmethylated. Accordingly, microbial infection and administered DNA can in some cases result in stimulation of innate immune responses.

The term "immunostimulatory" or "stimulating an immune response" as used herein includes stimulation of cell types that participate in immune reactions and enhancement of an immune response to a specific antigenic substance. An immune response that is stimulated by an immunostimulatory nucleic acid is generally a "Th1-type" immune response, as opposed to a "Th2-type" immune response. Th1-type immune responses are normally characterized by "delayed-type hypersensitivity" reactions to an antigen and activated macrophage function and can be detected at the biochemical level by increased levels of Th1-associated cytokines such as IFN-γ, IL-2, IL-12, and TNF-β. Th2-type immune responses are generally associated with high levels of antibody production, especially IgE antibody production and enhanced eosinophils numbers and activation, as well as expression of Th2-associated cytokines such as IL-4, IL-5 and IL-13.

The term "innate immune response" or "innate immunity" as used herein includes a variety of innate resistance mechanisms by which a cell or individual recognizes and responds to the presence of a pathogen. As used herein, an "innate immune response" includes the intracellular and intercellular events and reactions that occur when the cell recognizes pathogen associated molecular patterns or signals. Cellular receptors active in an innate immune response include a family of Toll-like receptors (TLRs) and microbial ligands have been identified for several TLRs, as described herein.

The term "immunoregulatory sequence" or "IRS" as used herein refers to a nucleic acid sequence that inhibits and/or suppresses a measurable innate immune response as measured in vitro, in vivo and/or ex vivo. The term "immunoregulatory polynucleotide" or "IRP" as used herein refers to a polynucleotide comprising at least one IRS that inhibits and/or suppresses a measurable innate immune response as measured in vitro, in vivo and/or ex vivo. Inhibition of a TLR, e.g., TLR-7, 8, or 9, includes without limitation inhibition at the receptor site, e.g., by blocking ligand-receptor binding, and inhibition of the downstream signal pathway after ligand-receptor binding. Examples of measurable innate immune responses include, but are not limited to, secretion of cytokines, activation or expansion of lymphocyte populations such as NK cells, CD4+ T lymphocytes, CD8+ T lymphocytes, B lymphocytes, maturation of cell populations such as plasmacytoid dendritic cells and the like.

The term "immunoregulatory compound" or "IRC", as used herein, refers to a molecule which has immunoregulatory activity and which comprises a nucleic acid moiety comprising an IRS. The IRC may consist of a nucleic acid moiety that comprises more than one IRS, consists of an IRS, or has no immunostimulatory activity on its own. The IRC may consist of a polynucleotide (a "polynucleotide IRC") or it may comprise additional moieties. Accordingly, the term IRC includes compounds which incorporate one or more nucleic acid moieties, at least one of which comprises an IRC, covalently linked to a non-nucleotide spacer moiety.

The term "palindromic sequence" or "palindrome" refers to a nucleic acid sequence that is an inverted repeat, e.g., ABCDD'C'B'A', where the bases, e.g., A, and A', B and B', C and C', D and D', are capable of forming the Watson-Crick base pairs. Such sequences may be single-stranded or may form double-stranded structures or may form hairpin loop structures under some conditions. For example, as used herein, "an 8 base palindrome" refers to a nucleic acid sequence in which the palindromic sequence is 8 bases in length, such as ABCDD'C'B'A'. A palindromic sequence may be part of a polynucleotide which also contains non-palindromic sequences. A polynucleotide may contain one or more palindromic sequence portions and one or more non-palindromic sequence portions. Alternatively, a polynucleotide sequence may be entirely palindromic. In a polynucleotide with more than one palindromic sequence portions, the palindromic sequence portions may overlap with each other or the palindromic sequence portions may not overlap with each other.

The term "3'" generally refers to a region or position in a polynucleotide or oligonucleotide 3' (downstream) from another region or position in the same polynucleotide or oligonucleotide. The term "3' end" refers to the 3' terminus of the polynucleotide.

The term "5'" generally refers to a region or position in a polynucleotide or oligonucleotide 5' (upstream) from another region or position in the same polynucleotide or oligonucleotide. The term "5' end" refers to the 5' terminus of the polynucleotide.

The term "conjugate" refers to a complex in which an IRP and/or an IRC are linked. Such conjugate linkages include covalent and/or non-covalent linkages.

"Adjuvant" refers to a substance which, when added to an immunogenic agent such as antigen, nonspecifically enhances or potentiates an immune response to the agent in the recipient host upon exposure to the mixture.

The term "peptide" are polypeptides that are of sufficient length and composition to effect a biological response, e.g., antibody production or cytokine activity whether or not the peptide is a hapten. Typically, the peptides are at least six amino acid residues in length. The term "peptide" further includes modified amino acids (whether or not naturally or non-naturally occurring), such modifications including, but not limited to, phosphorylation, glycosylation, pegylation, lipidization and methylation.

A "delivery molecule" or "delivery vehicle" is a chemical moiety which facilitates, permits, and/or enhances delivery of an IRP and/or IRC to a particular site and/or with respect to particular timing.

An "individual" is a vertebrate, such as avian, and is preferably a mammal, more preferably a human. Mammals include, but are not limited to, humans, primates, farm animals, sport animals, rodents and pets.

An "effective amount" or a "sufficient amount" of a substance is that amount sufficient to effect beneficial or desired results, including clinical results, and, as such, an "effective amount" depends upon the context in which it is being applied. In the context of administering a composition that suppresses a TLR-9 dependent immune response, an effective amount of an IRP is an amount sufficient to inhibit or decrease a cellular response to stimulation through TLR-9. In the context of administering a composition that suppresses a TLR-7/8 dependent immune response, an effective amount of an IRP is an amount sufficient to inhibit or decrease a cellular response to stimulation through TLR-7/8. An effective amount can be administered in one or more administrations.

The term "co-administration" as used herein refers to the administration of at least two different substances sufficiently close in time to regulate an immune response. Preferably, co-administration refers to simultaneous administration of at least two different substances.

"Suppression" or "inhibition" of a response or parameter includes decreasing that response or parameter when compared to otherwise same conditions except for a condition or parameter of interest, or alternatively, as compared to another condition. For example, a composition comprising an IRP which suppresses immunostimulatory nucleic acid induced cytokine production reduces cytokine production as compared to, for example, cytokine production induced by the immunostimulatory nucleic acid alone. As another example, a composition comprising an IRP which suppresses cytokine production associated with an innate immune response reduces the extent and/or levels of cytokine production as compared to, for example, extent and/or levels of cytokine produced by the innate immune response alone. B cell "suppression" includes, for example, reduced B cell proliferation, reduced B cell activation and/or reduced production of cytokines, such as IL-6 and/or TNF-α, from the stimulated B cell. Inhibition of a TLR response, e.g., a TLR-7, 8, or 9 response, includes, but is not limited to, inhibition at the receptor site, e.g., by preventing or blocking effective ligand-receptor binding, and inhibition of the downstream signal pathway, e.g., after effective ligand-receptor binding.

"Stimulation" of a response or parameter includes eliciting and/or enhancing that response or parameter. For example, "stimulation" of an immune response, such as innate immune response or Th1 response, means an increase in the response, which can arise from eliciting and/or enhancement of a response. Similarly, "stimulation" of a cytokine or cell type (such as CTLs) means an increase in the amount or level of cytokine or cell type. B cell "stimulation" includes, for example, enhanced B cell proliferation, induced B cell activation and/or increased production of cytokines, such as IL-6 and/or TNF-α, from the stimulated B cell.

As used herein, and as well-understood in the art, "treatment" is an approach for obtaining beneficial or desired results, including clinical results. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease or disorder means that the extent and/or undesirable clinical manifestations of a disorder or a disease state are lessened and/or time course of the progression is slowed or lengthened, as compared to not treating the disorder. Especially in the autoimmune disease context, as is well understood by those skilled in the art, palliation may occur upon regulation or reduction of the unwanted immune response. Further, palliation does not necessarily occur by administration of one dose, but often occurs upon administration of a series of doses. Thus, an amount sufficient to palliate a response or disorder may be administered in one or more administrations.

As used herein, the term "comprising" and its cognates are used in their inclusive sense; that is, equivalent to the term "including" and its corresponding cognates.

Compositions of the Invention

The invention provides immunoregulatory sequences (IRS), immunoregulatory polynucleotides (IRPs) and immunoregulatory compounds (IRCs) for regulating innate immune responses in individuals. Each IRP and IRC of the invention comprises at least one IRS.

Compositions of the invention comprise an immunoregulatory polynucleotide or an immunoregulatory compound alone (or a combination of two or more IRPs and/or IRCs). Compositions of the invention may comprise an IRP or IRC and a pharmaceutically acceptable excipient. Pharmaceutically acceptable excipients, including buffers, are described herein and well known in the art. *Remington: The Science and Practice of Pharmacy*, 20th edition, Mack Publishing (2000).

Immunoregulatory Polynucleotides and Immunoregulatory Compounds

In accordance with the present invention, an IRP or an IRC contains at least one immunoregulatory sequence. In some instances, an immunoregulatory sequence (IRS) comprises a 5'-G,C-3' sequence. In some instances, an IRS includes at least one TGC trinucleotide sequence at or near the 5' end of the polynucleotide (i.e., 5'-TGC). In some instances, an IRS comprises a 5'-GGGG-3' sequence. In some instances, an IRS does not comprise a 5'-GGGG-3' sequence. Accordingly, in some instances, an IRP or IRC does not comprise a 5'-GGGG-3' sequence. In some instances, an IRP or IRC comprising a 5'-GGGG-3' sequence is particularly effective when used in the single-stranded form. In some instances, an IRP or IRC comprising a 5'-GGGG-3' sequence is particularly effective when made with a phosphothioate backbone.

As demonstrated herein, particular IRPs and IRCs inhibit TLR-7 and/or TLR-8 dependent cell responses. Also, particular IRPs and IRCs inhibit TLR-9 dependent cell responses, and particular IRPs and IRCs inhibit TLR-7/8 dependent cell responses and TLR-9 dependent cell responses. As used herein, "TLR-7/8" refers to "TLR-7 and/or TLR-8." Accordingly, as used herein, "TLR-7/8/9" refers to "(TLR-7 and/or TLR-8) and TLR-9." Also as shown herein, certain IRPs do not inhibit TLR4 dependent cell responses.

Immunostimulatory nucleic acids and other stimulators of an innate immune response have been described in the art and their activity may be readily measured using standard assays which indicate various aspects of an innate immune response, such as cytokine secretion, antibody production, NK cell activation, B cell proliferation, T cell proliferation, dendritic cell maturation. See, e.g. Krieg et al. (1995) *Nature* 374:546-549; Yamamoto et al. (1992) *J. Immunol.* 148:4072-4076; Klinman et al. (1997) *J. Immunol.* 158:3635-3639; Pisetsky (1996) *J. Immunol.* 156:421-423; Roman et al. (1997) *Nature Med.* 3:849-854; Hemmi et al. (2000), *Supra*; Lee et al. (2003), *Supra;* WO 98/16247; WO 98/55495; WO 00/61151 and U.S. Pat. No. 6,225,292. Accordingly, these and other methods can be used to identify, test and/or confirm immunoregulatory sequences, polynucleotides and/or compounds. For example, the effect of IRP or IRC can be determined when cells or individuals in which an innate immune response has been stimulated are contacted with the IRP or IRC.

As is clearly conveyed herein, it is understood that, with respect to formulae described herein, any and all parameters are independently selected. For example, if x=0-2, y may be independently selected regardless of the values of x (or any other selectable parameter in a formula). Preferably, the IRP or IRC which comprises the IRS is an oligonucleotide with at least one phosphothioate backbone linkage.

As demonstrated herein, one class of IRS discovered is particularly effective in inhibiting TLR9 dependent cell stimulation. Accordingly, IRS with this activity are referred to as "TLR9 class" IRS.

In some embodiments, an IRS may comprise a sequence of the formula: $X_1GGGGX_2X_3$ (SEQ ID NO:1) wherein $X_1, X_2$, and $X_3$ are nucleotides, provided that if $X_1$=C or A, then $X_2X_3$ is not AA. In some embodiments, an IRS may comprise a sequence of the formula SEQ ID NO:1 wherein $X_1$ is C or A. In some embodiments, an IRS may comprise a sequence of the formula: $X_1GGGGX_2X_3$ (SEQ ID NO:2) wherein $X_1, X_2$, and $X_3$ are nucleotides, provided that if $X_1$=C or A, then $X_2X_3$ is not AA, and wherein $X_1$ is C or A.

In some embodiments, an IRS may comprise a sequence of the formula: $GGN_nX_1GGGGX_2X_3$ (SEQ ID NO:3), wherein n is an integer from 1 to about 100 (preferably from 1 to about 20), each N is a nucleotide, and $X_1, X_2$, and $X_3$ are nucleotides, provided that if $X_1$=C or A, then $X_2X_3$ is not AA. In some embodiments, an IRS may comprise a sequence of the formula SEQ ID NO:3 wherein $X_1$ is C or A.

In some embodiments, an IRS may comprise a sequence of the formula: $N_iTCCN_j(GG)_kN_mX_1GGGGX_2X_3$ (SEQ ID NO: 4), wherein each N is a nucleotide, wherein i is an integer from 1 to about 50, wherein j is an integer from 1 to about 50, k is 0 or 1, m is an integer from 1 to about 20, and $X_1, X_2$, and $X_3$ are nucleotides, provided that if $X_1$=C or A, then $X_2X_3$ is not AA. In some embodiments, an IRS may comprise a sequence of the formula SEQ ID NO:4 wherein $X_1$ is C or A.

In some embodiments, an IRS may comprise a sequence of the formula: $X_1X_2X_3GGGGAA$ (SEQ ID NO:5), wherein $X_1, X_2$, and $X_3$ are nucleotides, provided that if $X_3$=C or A, then $X_1X_2$ is not GG.

Examples of oligonucleotide sequences comprising SEQ ID NO:1, 2, 3, 4, or 5 include the following sequences:

5'-TCCTAACGGGGAAGT-3';
(SEQ ID NO: 10 (C827))

5'-TCCTAAGGGGGAAGT-3';
(SEQ ID NO: 11 (C828))

5'-TCCTAACGGGGTTGT-3';
(SEQ ID NO: 12 (C841))

5'-TCCTAACGGGGCTGT-3';
(SEQ ID NO: 13 (C842))

5'-TCCTCAAGGGGCTGT-3';
(SEQ ID NO: 14 (C843))

5'-TCCTCAAGGGGTTGT-3';
(SEQ ID NO: 15 (C844))

5'-TCCTCATGGGGTTGT-3';
(SEQ ID NO: 16 (C845))

5'-TCCTGGAGGGGTTGT-3';
(SEQ ID NO: 17 (C869))

5'-TCCTGGAGGGGCTGT-3';
(SEQ ID NO: 18 (C870))

5'-TCCTGGAGGGGCCAT-3';
(SEQ ID NO: 19 (C871))

5'-TCCTGGAGGGGTCAT-3';
(SEQ ID NO: 20 (C872))

5'-TCCGGAAGGGGAAGT-3';
(SEQ ID NO: 21 (C873))
and

5'-TCCGGAAGGGGTTGT-3'.
(SEQ ID NO: 22 (C874))

In some embodiments, an IRS may comprise a sequence of any of SEQ ID NO:1, 2, 3, 4, or 5, wherein at least one G is replaced by 7-deaza-dG. For example, in some embodiments, the IRS may comprise the sequence 5'-TCCTGGAGZ'GGTTGT-3' (Z'=7-deaza-dG; SEQ ID NO:23 (C920)).

IRPs comprising SEQ ID NO:1, 2, 3, 4, or 5 or an IRP comprising SEQ ID NO:1, 2, 3, 4, or 5, wherein at least one G is replaced by 7-deaza-dG are particularly effective in inhibiting TLR9 dependent cell stimulation. Other IRS sequences which are also effective in inhibiting TLR9 dependent cell signaling include the following:

5'-TGACTGTAGGCGGGGAAGATGA-3';
(SEQ ID NO: 24 (C533))

5'-GAGGAAGCTGGACCTTCCAT-3';
(SEQ ID NO: 25 (C707))
and

5'-CCTCAAGCTTGAGZ'GG-3'.
(Z' = 7-deaza-dG; SEQ ID NO: 26 (C891))

As shown herein, some IRS are particularly effective in inhibiting TLR7/8 dependent cell stimulation. Accordingly, IRS with this activity are referred to as "TLR7/8 class" IRS. For example, an oligonucleotide comprising the sequence 5'-TGCTTGCAAGCTTGCAAGCA-3' (SEQ ID NO:27 (C661)) inhibits TLR7/8 dependent cell stimulation.

In some embodiments, an IRS comprises a fragment of SEQ ID NO:27 (C661) and includes at least a 10 base palindromic portion thereof. For example, such sequences include the following sequences:

5'-TGCTTGCAAGCTTGCAAG-3';
(SEQ ID NO: 28 (C921))

5'-TGCTTGCAAGCTTGCA-3';
(SEQ ID NO: 29 (C922))

5'-GCTTGCAAGCTTGCAAGCA-3';
(SEQ ID NO: 30 (C935))

```
5'-CTTGCAAGCTTGCAAGCA-3';
(SEQ ID NO: 31 (C936))
and

5'-TTGCAAGCTTGCAAGCA-3'.
(SEQ ID NO: 32 (C937))
```

In some embodiments, the IRP consists of SEQ ID NO:27 (C661), or a fragment thereof. In some embodiments, an IRP consists of a fragment of SEQ ID NO:27 (C661) and includes at least a 10 base palindromic portion thereof.

In some embodiments, an IRP effective in inhibiting TLR7/8 dependent cell stimulation consists of the sequence 5'-TGCN$_m$-3' (SEQ ID NO:120) where N is a nucleotide, m is an integer from 5 to about 50 and wherein the sequence N$_1$-N$_m$ comprises at least one GC dinucleotide. In some embodiments, such an IRP consists of the sequence 5'-TGC-N$_m$A-3'(SEQ ID NO:121), the sequence 5'-TGCN$_m$CA-3' (SEQ ID NO:122) or the sequence 5'-TGCN$_m$GCA-3'(SEQ ID NO:123). For example, in some embodiments, the IRP may consist of the following sequences:

```
5'-TGCTTGCAAGCTAGCAAGCA-3';
(SEQ ID NO: 33 (C917))

5'-TGCTTGCAAGCTTGCTAGCA-3';
(SEQ ID NO: 34 (C918))

5'-TGCTTGACAGCTTGACAGCA-3';
(SEQ ID NO: 35 (C932))

5'-TGCTTAGCAGCTATGCAGCA-3';
(SEQ ID NO: 36 (C933))
or

5'-TGCAAGCAAGCTAGCAAGGA-3'.
(SEQ ID NO: 37 (C934))
```

Other IRS sequences which are also effective in inhibiting TLR7/8 dependent cell signaling include the following:

```
5'-TGCAAGCTTGCAAGCTTG CAA GCT T-3';
(SEQ ID NO: 38 (C793))

5'-TGCTGCAAGCTTGCAGAT GAT-3';
(SEQ ID NO: 39 (C794))

5'-TGCTTGCAAGCTTGCAAGC-3';
(SEQ ID NO: 40 (C919))

5'-TGCAAGCTTGCAAGCTTGCAAT-3';
(SEQ ID NO: 41 (C923))

5'-TGCTTGCAAGCTTG-3';
(SEQ ID NO: 42 (C930))

5'-AGCTTGCAAGCTTGCAAGCA-3';
(SEQ ID NO: 43 (C938))

5'-TACTTGCAAGCTTGCAAGCA-3';
(SEQ ID NO: 44 (C939))

5'-TGATTGCAAGCTTGCAAGCA-3';
(SEQ ID NO: 45 (C940))

5'-AAATTGCAAGCTTGCAAGCA-3';
(SEQ ID NO: 46 (C941))

5'-TGCTGGAGGGGTTGT-3';
(SEQ ID NO: 47 (C945))

5'-AAATTGACAGCTTGACAGCA-3';
(SEQ ID NO: 48 (C951))

5'-TGATTGACAGCTTGACAGCA-3';
(SEQ ID NO: 49 (C959))

5'-TGATTGACAGATTGACAGCA-3';
(SEQ ID NO: 50 (C960))
and

5'-TGATTGACAGATTGACAGAC-3'.
(SEQ ID NO: 51 (C961))
```

Another class of IRS include those which are particularly effective in inhibiting both TLR7/8 and TLR9 dependent cell stimulation. Accordingly, IRS with this activity are referred to as "TLR7/8/9 class" IRS. In some instances, a combination of a TLR7/8 class IRS with a TLR9 class IRS results in an IRS of the TLR7/8/9 class.

The TLR7/8/9 class of IRS include those comprising the sequence TGCN$_m$TCCTGGAGGGGTTGT-3' (SEQ ID NO:6) where each N is a nucleotide and m is an integer from 0 to about 100, in some instances from 0 to about 50, preferably from 0 to about 20.

In some embodiments, an IRS comprises SEQ ID NO:6, wherein the sequence N$_1$-N$_m$ comprises a fragment of the sequence 5'-TTGACAGCTTGACAGCA-3' (SEQ ID NO:7). A fragment of SEQ ID NO:7 is any portion of that sequence, for example, TTGAC or GCTTGA. In some embodiments, the fragment of SEQ ID NO:7 is from the 5' end of SEQ ID NO:7, including, for example, TTGAC or TTG.

In some embodiments, the IRS comprises the sequence 5'-TGCRRZNYY-3' (SEQ ID NO:8), wherein Z is any nucleotide except C, wherein N is any nucleotide, wherein when Z is not G or inosine, N is guanosine or inosine. In other embodiments, the IRS comprises the sequence 5'-TGCRRZNpoly(Pyrimidine)-3' (SEQ ID NO:9), wherein Z is any nucleotide except C, wherein N is any nucleotide, wherein when Z is not G or inosine, N is guanosine or inosine.

Examples of IRS sequences which are also effective in inhibiting TLR7/8/9 dependent cell signaling include the following:

```
5'-TGCTCCTGGAGGGGTTGT-3';
(SEQ ID NO: 52 (C954))

5'-TGCTTGTCCTGGAGGGGTTGT-3';
(SEQ ID NO: 53 (C956))

5'-TGCTTGACATCCTGGAGGGGTTGT-3';
(SEQ ID NO: 54 (C957))

5'-TGCTTGACAGCTTGACAGTCCTGGAGGGGTTGT-3';
(SEQ ID NO: 55 (C962))

5'-TGCTTGACAGCTTGATCCTGGAGGGGTTGT-3';
(SEQ ID NO: 56 (C963))

5'-TGCTTGACAGCTTCCTGGAGGGGTTGT-3';
(SEQ ID NO: 57 (C964))

5'-TGCTTGACAGCTTGCTCCTGGAGGGGTTGT-3';
(SEQ ID NO: 58 (C965))

5'-TGCTTGACAGCTTGCTTGTCCTGGAGGGGTTGT-3';
(SEQ ID NO: 59 (C966))

5'-TGCTTGACAGCTTGACAGCATGCTGGAGGGGTGT-3';
(SEQ ID NO: 60 (C967))

5'-TGCTTGACAGCTTGACAGCATCCTGGAGGGGTTGT-3';
(SEQ ID NO: 61 (C968))

5'-TGCTTGACAGCTTGACAGCATCCTGGAGGGGT-3';
(SEQ ID NO: 62 (C969))
```

-continued

5'-TGCTTGACAGCTTGACAGCATCCTGGAGGGG-3';
(SEQ ID NO: 63 (C970))

5'-TGCTTGCAAGCTTGCTCCTGGAGGGGTTGT-3';
(SEQ ID NO: 64 (C971))

5'-TGCTTGCAAGCTTCCTGGAGGGGTTGT-3';
(SEQ ID NO: 65 (C972))
and

5'-TGCTTGCAAGCTTGCAAGCATCCTGGAGGGGTTGT-3'.
(SEQ ID NO: 66 (C908))

As described herein, some IRPs are particularly effective in suppressing TLR9 dependent cell responses. Such IRPs include, but are not limited to, SEQ ID NO:24 (C533); SEQ ID NO:25 (C707); SEQ ID NO:85 (1019); SEQ ID NO:26 (C891); SEQ ID NO:10 (C827); SEQ ID NO:11 (C828); SEQ ID NO:12 (C841); SEQ ID NO:13 (C842); SEQ ID NO:14 (C843); SEQ ID NO:15 (C844); SEQ ID NO:16 (C845); SEQ ID NO:17 (C869); SEQ ID NO:18 (C870); SEQ ID NO:19 (871); SEQ ID NO:20 (C872); SEQ ID NO:21 (C873); SEQ ID NO:22 (C874); SEQ ID NO:23 (C920), and SEQ ID NO:66 (C908).

As described herein, some IRPs are particularly effective in suppressing TLR7/8 dependent cell responses. Such IRPs include, but are not limited to, SEQ ID NO:17 (C869); SEQ ID NO:23 (C920); SEQ ID NO:27 (C661); SEQ ID NO:38 (C793); SEQ ID NO:39 (C794); SEQ ID NO:33 (C917); SEQ ID NO:34 (C918); SEQ ID NO:40 (C919); SEQ ID NO:28 (C921); SEQ ID NO:29 (C922); SEQ ID NO:41 (C923), and SEQ ID NO:66 (C908).

An IRP may be single stranded or double stranded DNA, as well as single or double-stranded RNA or other modified polynucleotides. An IRP may be linear, may be circular or include circular portions and/or may include a hairpin loop. An IRP may contain naturally-occurring or modified, non-naturally occurring bases, and may contain modified sugar, phosphate, and/or termini. Various such modifications are described herein.

The heterocyclic bases, or nucleic acid bases, which are incorporated in the IRP can be the naturally-occurring principal purine and pyrimidine bases, (namely uracil, thymine, cytosine, adenine and guanine, as mentioned above), as well as naturally-occurring and synthetic modifications of said principal bases. Thus, an IRP may include 2'-deoxyuridine and/or 2-amino-2'-deoxyadenosine.

The IRP may comprise at least one modified base. As used herein, the term "modified base" is synonymous with "base analog", for example, "modified cytosine" is synonymous with "cytosine analog." Similarly, "modified" nucleosides or nucleotides are herein defined as being synonymous with nucleoside or nucleotide "analogs." Examples of base modifications include, but are not limited to, addition of an electron-withdrawing moiety to C-5 and/or C-6 of a cytosine of the IRP. Preferably, the electron-withdrawing moiety is a halogen, e.g., 5-bromocytosine, 5-chlorocytosine, 5-fluorocytosine, 5-iodocytosine. Other examples of base modifications include, but are not limited to, addition of an electron-withdrawing moiety to C-5 and/or C-6 of a uracil of the immunoregulatory polynucleotide. Preferably, the electron-withdrawing moiety is a halogen. Such modified uracils can include, but are not limited to, 5-bromouracil, 5-chlorouracil, 5-fluorouracil, 5-iodouracil.

Other examples of base modifications include the addition of one or more thiol groups to the base including, but not limited to, 6-thio-guanine, 4-thio-thymine, and 4-thio-uracil.

Other examples of base modifications include, but are not limited to, N4-ethylcytosine, 7-deazaguanine, and 5-hydroxycytosine. See, for example, Kandimalla et al. (2001) *Bioorg. Med. Chem.* 9:807-813.

The IRP can contain phosphate-modified polynucleotides, some of which are known to stabilize the polynucleotide. Accordingly, some embodiments includes stabilized immunoregulatory polynucleotides. For example, in addition to phosphodiester linkages, phosphate modifications include, but are not limited to, methyl phosphonate, phosphorothioate, phosphoramidate (bridging or non-bridging), phosphotriester and phosphorodithioate and may be used in any combination. Other non-phosphate linkages may also be used. In some embodiments, polynucleotides of the present invention comprise only phosphorothioate backbones. In some embodiments, polynucleotides of the present invention comprise only phosphodiester backbones. In some embodiments, an IRP may comprise a combination of phosphate linkages in the phosphate backbone such as a combination of phosphodiester and phosphorothioate linkages.

IRPs used in the invention can comprise one or more ribonucleotides (containing ribose as the only or principal sugar component), deoxyribonucleotides (containing deoxyribose as the principal sugar component), or, as is known in the art, modified sugars or sugar analogs can be incorporated in the IRP. Thus, in addition to ribose and deoxyribose, the sugar moiety can be pentose, deoxypentose, hexose, deoxyhexose, glucose, arabinose, xylose, lyxose, and a sugar "analog" cyclopentyl group. The sugar can be in pyranosyl or in a furanosyl form. In the IRP, the sugar moiety is preferably the furanoside of ribose, deoxyribose, arabinose or 2'-O-alkylribose, and the sugar can be attached to the respective heterocyclic bases either in a or 13 anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification in the IRP includes, but is not limited to, 2'-O-methyl-uridine and 2'-O-methyl-cytidine. The preparation of these sugars or sugar analogs and the respective "nucleosides" wherein such sugars or analogs are attached to a heterocyclic base (nucleic acid base) per se is known, and need not be described here, except to the extent such preparation can pertain to any specific example. Sugar modifications may also be made and combined with any phosphate modification in the preparation of an IRP.

The IRP can be synthesized using techniques and nucleic acid synthesis equipment which are well known in the art including, but not limited to, enzymatic methods, chemical methods, and the degradation of larger oligonucleotide sequences. See, for example, Ausubel et al. (1987); and Sambrook et al. (1989). When assembled enzymatically, the individual units can be ligated, for example, with a ligase such as T4 DNA or RNA ligase. U.S. Pat. No. 5,124,246. Oligonucleotide degradation can be accomplished through the exposure of an oligonucleotide to a nuclease, as exemplified in U.S. Pat. No. 4,650,675.

The IRP can also be isolated using conventional polynucleotide isolation procedures. Such procedures include, but are not limited to, hybridization of probes to genomic or cDNA libraries to detect shared nucleotide sequences, antibody screening of expression libraries to detect shared structural features and synthesis of particular native sequences by the polymerase chain reaction.

Circular immunoregulatory polynucleotide can be isolated, synthesized through recombinant methods, or chemically synthesized. Where the circular IRP is obtained through isolation or through recombinant methods, the IRP will preferably be a plasmid. The chemical synthesis of smaller circular oligonucleotides can be performed using any method described in the literature. See, for instance, Gao et al. (1995) *Nucleic Acids Res.* 23:2025-2029; and Wang et al. (1994) *Nucleic Acids Res.* 22:2326-2333.

The techniques for making polynucleotides and modified polynucleotides are known in the art. Naturally occurring DNA or RNA, containing phosphodiester linkages, is generally synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Once the desired polynucleotide sequence has been synthesized, the polynucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in Protocols for Oligonucleotides and Analogs, Synthesis and Properties (Agrawal, ed.) Humana Press, Totowa, N.J.; Warner et al. (1984) *DNA* 3:401 and U.S. Pat. No. 4,458,066.

Synthesis of polynucleotides containing modified phosphate linkages or non-phosphate linkages is also known in the art. For a review, see Matteucci (1997) "Oligonucleotide Analogs: an Overview" in Oligonucleotides as Therapeutic Agents, (D. J. Chadwick and G. Cardew, ed.) John Wiley and Sons, New York, N.Y. The phosphorous derivative (or modified phosphate group) which can be attached to the sugar or sugar analog moiety in the polynucleotides of the present invention can be a monophosphate, diphosphate, triphosphate, alkylphosphonate, phosphorothioate, phosphorodithioate, phosphoramidate or the like. The preparation of the above-noted phosphate analogs, and their incorporation into nucleotides, modified nucleotides and oligonucleotides, per se, is also known and need not be described here in detail. Peyrottes et al. (1996) *Nucleic Acids Res.* 24:1841-1848; Chaturvedi et al. (1996) *Nucleic Acids Res.* 24:2318-2323; and Schultz et al. (1996) *Nucleic Acids Res.* 24:2966-2973. For example, synthesis of phosphorothioate oligonucleotides is similar to that described above for naturally occurring oligonucleotides except that the oxidation step is replaced by a sulfurization step (Zon (1993) "Oligonucleoside Phosphorothioates" in Protocols for Oligonucleotides and Analogs, Synthesis and Properties (Agrawal, ed.) Humana Press, pp. 165-190). Similarly the synthesis of other phosphate analogs, such as phosphotriester (Miller et al. (1971) *JACS* 93:6657-6665), non-bridging phosphoramidates (Jager et al. (1988) *Biochem.* 27:7247-7246), N3' to P5' phosphoramidiates (Nelson et al. (1997) *JOC* 62:7278-7287) and phosphorodithioates (U.S. Pat. No. 5,453,496) has also been described. Other non-phosphorous based modified oligonucleotides can also be used (Stirchak et al. (1989) *Nucleic Acids Res.* 17:6129-6141).

Those skilled in the art will recognize that a large number of "synthetic" non-natural nucleosides comprising various heterocyclic bases and various sugar moieties (and sugar analogs) are available in the art, and that as long as other criteria of the present invention are satisfied, the IRP can include one or several heterocyclic bases other than the principal five base components of naturally-occurring nucleic acids. Preferably, however, the heterocyclic base in the IRP includes, but is not limited to, uracil-5-yl, cytosin-5-yl, adenin-7-yl, adenin-8-yl, guanin-7-yl, guanin-8-yl, 4-aminopyrrolo[2,3-d]pyrimidin-5-yl, 2-amino-4-oxopyrolo[2,3-d]pyrimidin-5-yl, 2-amino-4-oxopyrrolo[2,3-d]pyrimidin-3-yl groups, where the purines are attached to the sugar moiety of the IRP via the 9-position, the pyrimidines via the 1-position, the pyrrolopyrimidines via the 7-position and the pyrazolopyrimidines via the 1-position.

The preparation of base-modified nucleosides, and the synthesis of modified oligonucleotides using said base-modified nucleosides as precursors, has been described, for example, in U.S. Pat. Nos. 4,910,300, 4,948,882, and 5,093,232. These base-modified nucleosides have been designed so that they can be incorporated by chemical synthesis into either terminal or internal positions of an oligonucleotide. Such base-modified nucleosides, present at either terminal or internal positions of an oligonucleotide, can serve as sites for attachment of a peptide. Nucleosides modified in their sugar moiety have also been described (including, but not limited to, e.g., U.S. Pat. Nos. 4,849,513, 5,015,733, 5,118,800, 5,118,802) and can be used similarly.

In some embodiments, an immunoregulatory polynucleotide is less than about any of the following lengths (in bases or base pairs): 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10; 9; 8; 7; 6; 5; 4. In some embodiments, an immunoregulatory polynucleotide is greater than about any of the following lengths (in bases or base pairs): 4; 5; 6, 7, 8, 9, 10; 11; 12; 13; 14; 15; 20; 25; 30; 40; 50; 60; 75; 100; 125; 150; 175; 200; 250; 300; 350; 400; 500; 750; 1000; 2000; 5000; 7500; 10000; 20000; 50000. Alternately, the immunoregulatory polynucleotide can be any of a range of sizes having an upper limit of 10,000; 5,000; 2500; 2000; 1500; 1250; 1000; 750; 500; 300; 250; 200; 175; 150; 125; 100; 75; 60; 50; 40; 30; 25; 20; 15; 14; 13; 12; 11; 10; 9; 8; 7; 6; 5; 4 and an independently selected lower limit of 4; 5; 6; 7; 8; 9; 10; 11; 12; 13; 14; 15; 20; 25; 30; 40; 50; 60; 75; 100; 125; 150; 175; 200; 250; 300; 350; 400; 500; 750; 1000; 2000; 5000; 7500, wherein the lower limit is less than the upper limit. In some embodiments, an IRP is preferably about 200 or less bases in length.

The invention also provides methods of making the immunoregulatory polynucleotides described herein. The methods may be any of those described herein. For example, the method could be synthesizing the IRP (for example, using solid state synthesis) and may further comprise any purification step(s). Methods of purification are known in the art.

In certain embodiments, the invention is directed to immunoregulatory compounds (IRCs) which have immunoregulatory activity and which comprise a nucleic acid moiety comprising an IRS. IRCs of the invention contain one or more nucleic acid moieties and one or more non-nucleic acid spacer moieties. Compounds conforming to a variety of structural formulas are contemplated for use as IRCs, including the core structures described in formulas I-VII, below. Formulas I-III show core sequences for "linear IRCs." Formulas IV-VI show core sequences for "branched IRCs." Formula VII shows a core structure for "single-spacer IRCs."

In each formula provided herein, "N" designates a nucleic acid moiety (oriented in either a 5'→3' or 3'→5' orientation) and "S" designates a non-nucleic acid spacer moiety. A dash ("-") designates a covalent bond between a nucleic acid moiety and a non-nucleic acid spacer moiety. A double dash ("--") designates covalent bonds between a non-nucleic acid spacer moiety and at least 2 nucleic acid moieties. A triple dash ("-") designates covalent bonds between a non-nucleic acid spacer moiety and multiple (i.e., at least 3) nucleic acid moieties. Subscripts are used to designate differently positioned nucleic acid or non-nucleic acid spacer moieties. However, the use of subscripts to distinguish different nucleic acid moieties is not intended to indicate that the moieties necessarily have a different structure or sequence. Similarly, the use of subscripts to distinguish different spacer moieties is not intended to indicate that the moieties necessarily have different structures. For example, in formula II, infra, the nucleic acid moieties designated $N_1$ and $N_2$ can have the same or different sequences, and the spacer moieties designated $S_1$ and $S_2$ can have the same or different structures. Further, it is contemplated that additional chemical moieties (e.g., phosphate, mononucleotide, additional nucleic acid moieties, alkyl, amino, thio or disulfide groups or linking groups, and/or spacer moieties) may be covalently bound at the termini of the core structures.

Linear IRCs have structures in which the non-nucleic acid spacer moieties in the core structure are covalently bound to no more than two nucleic acid moieties. Exemplary linear IRCs conform to the following formulas:

$$N_1\text{-}S_1\text{-}N_2 \tag{I}$$

$$N_1\text{-}S_1\text{-}N_2\text{-}S_2\text{-}N_3 \tag{II}$$

$$N_1\text{-}S_1\text{—}N_2\text{-}S_2\text{-}[N_v\text{-}S_v]_A \tag{III}$$

where A is an integer between 1 and about 100 and $[N_v\text{-}S_v]$ indicates A additional iterations of nucleic acid moieties conjugated to non-nucleic acid spacer moieties. The subscript "v" indicates that N and S are independently selected in each iteration of "$[N_v\text{-}S_v]$." "A" is sometimes between 1 and about 10, sometimes between 1 and 3, sometimes exactly 1, 2, 3, 4 or 5. In some embodiments, A is an integer in a range defined by a lower limit of 1, 2, 3, 4, or 5, and an independently selected upper limit of 10, 20, 50 or 100 (e.g., between 3 and 10).

Exemplary linear IRCs include:

$$N_1\text{-HEG-}N_2\text{—OH} \tag{Ia}$$

$$N_1\text{-HEG-}N_1\text{—PO}_4 \tag{Ib}$$

$$N_1\text{-HEG-}N_2\text{-HEG} \tag{Ic}$$

$$\text{HEG-}N_1\text{-HEG-}N_1\text{-HEG} \tag{Id}$$

$$N_1\text{-HEG-}N_2\text{-HEG-}N_1 \tag{Ie}$$

$$N_1\text{-HEG-}N_2\text{-(HEG)}_4\text{-}N_3 \tag{If}$$

$$(N_1)_2\text{-glycerol-}N_1\text{-HEG-}N_1 \tag{Ig}$$

$$\text{PO}_4\text{—}N_1\text{-HEG-}N_2 \tag{Ih}$$

$$N_1\text{-(HEG)}_{15}\text{-T} \tag{Ii}$$

$$(N_1\text{-(HEG)}_2\text{-glycerol-HEG-}N_2 \tag{Ij}$$

$$N_1\text{-HEG-T-HEG-T} \tag{Ik}$$

Wherein HEG refers to hexa-(ethylene glycol). TEG refers to tetra-(ethylene glycol).

PreferrEd linear IRCs include:

```
5'-TGCTTGCAAGCTTGCAAGCA-HEG-TCCTGGAGGGGTGT-3';
(SEQ ID NO: 67 (C907, C661-HEG-C869)

5'-TGCTTGCAAGCTAGCAAGCA-HEG-TCCTGGAGGGGTTGT-3';
(SEQ ID NO: 68 (C913, C917-HEG-C869)

5'-TGCTTGCAAGCTTGCTAGCA-HEG-TCCTGGAGGGGTTGT-3';
(SEQ ID NO: 69 (C914, C918-HEG-C869)
```

-continued
```
5'-TGCTTGCAAGCTTGCTAGCA-HEG-TCCTGGAGZGGTTGT-3';
(SEQ ID NO: 70 (C916, C661-HEG-C920)
and 5'-TCCTGGAGGGGTTGT-HEG-TGCTTGCAAGCTTGCAAGCA-3'.
(SEQ ID NO: 71 (C928, C869-HEG-C661)
```

Branched IRCs comprise a multivalent spacer moiety ($S_p$) covalently bound to at least three (3) nucleic acid moieties. Exemplary branched IRCs are described according to the following formulas $$[N_v]_4\text{-}S_p \tag{IV}$$

$$[S_v\text{-}N_v]_4\text{-}S_p \tag{V}$$

$$(S_1\text{-}N_1)\text{-}S_p\text{-}(N_v)_A \tag{VI}$$

where $S_p$ is a multivalent spacer covalently bonded to the quantity "A" independently selected nucleic acid moieties $N_v$, $S_v\text{-}N_v$ (which comprises a spacer moiety covalently bound to a nucleic acid moiety). For formulas IV and V, A is at least 3. In various embodiments of formulas IV and V, A is an integer between 3 and 100 (inclusive), although A may be an integer in a range defined by a lower limit of about 3, 5, 10, 50, or 100 and an independently selected upper limit of about 5, 7, 10, 50, 100, 150, 200, 250, or 500, or alternately A may be greater than 500. For formula VI, A is at least 2, an integer in a range defined by a lower limit of 2, 5, 10, 50, or 100 and an independently selected upper limit of 5, 10, 50, 100, 150, 200, 250, or 500, or greater than 500.

Exemplary branched IRCs include:

$$(N_1)_2\text{-glycerol-}N_1 \tag{IVa}$$

$$(N_2\text{-HEG})_2\text{-glycerol-}N_1 \tag{IVb}$$

$$(N_1\text{-HEG-}N_2)_2\text{-glycerol-}N_1 \tag{IVc}$$

$$[(N_1)_2\text{-glycerol-}N_1]_2\text{-glycerol-}N_1 \tag{IVd}$$

Preferred branched IRCs include $(5'\text{-}N_1\text{-}3'\text{-HEG})_2\text{-glycerol-HEG-}5'\text{-}N_1\text{-}3'$ and $(5'\text{-}N_1\text{-}3'\text{-HEG})_2\text{-glycerol-HEG-}5'\text{-}N_1'$.

Single spacer IRCs comprise a structure in which there is a single nucleic acid moiety covalently conjugated to a single spacer moiety, i.e., $$N_1\text{-}S_1 \tag{VII}$$

In a preferred embodiment $S_1$ has the structure of a multimer comprising smaller units (e.g., HEG, TEG, glycerol, 1'2'-dideoxyribose, C2 alkyl-C12 alkyl subunits, and the like), typically connected by an ester linkage (e.g., phosphodiester or phosphorothioate ester), e.g., as described infra. See, e.g., formula VIIa, infra. The multimer can be heteromeric or homomeric. In one embodiment, the spacer is a heteromer of monomeric units (e.g., HEG, TEG, glycerol, 1'2'-dideoxyribose, C2 alkyl to C12 alkyl linkers, and the like) linked by an ester linkage (e.g., phosphodiester or phosphorothioate ester). See, e.g., formula VIM, infra.

Exemplary single spacer IRCs include:

$$N_1\text{—(HEG)}_{15} \tag{VIIa}$$

$$N_1\text{-HEG-propyl-HEG-propyl-HEG} \tag{VIIb}$$

In certain embodiments, the terminal structures of the IRC are covalently joined (e.g., nucleic acid moiety-to-nucleic acid moiety; spacer moiety-to-spacer moiety, or nucleic acid moiety-to-spacer moiety), resulting in a circular conformation.

IRCs for use in the immunoregulatory compositions of the invention include at least one nucleic acid moiety. The term "nucleic acid moiety," as used herein, refers to a nucleotide monomer (i.e., a mononucleotide) or polymer (i.e., comprising at least 2 contiguous nucleotides). As used herein, a nucleotide comprises (1) a purine or pyrimidine base linked to a sugar that is in an ester linkage to a phosphate group, or (2) an analog in which the base and/or sugar and/or phosphate ester are replaced by analogs, e.g., as described infra. In an IRC comprising more than one nucleic acid moiety, the nucleic acid moieties may be the same or different.

Nucleic acid moieties used in IRCs incorporated in the immunoregulatory compositions may comprise any of the IRS sequences disclosed herein, and may additionally be sequences of six base pairs or less. It is contemplated that in an IRC comprising multiple nucleic acid moieties, the nucleic acid moieties can be the same or different lengths. In certain embodiments where the IRC comprises more than one nucleic acid moiety, only one of the moieties need comprise the IRS.

It is contemplated that in a IRC comprising multiple nucleic acid moieties, the nucleic acid moieties can be the same or different. Accordingly, in various embodiments, IRCs incorporated into the immunoregulatory compositions comprise (a) nucleic acid moieties with the same sequence, (b) more than one iteration of a nucleic acid moiety, or (c) two or more different nucleic acid moieties. Additionally, a single nucleic acid moiety may comprise more than one IRS, which may be adjacent, overlapping, or separated by additional nucleotide bases within the nucleic acid moiety.

As described herein, some IRPs are particularly effective in suppressing TLR9 dependent cell responses and some IRPs are particularly effective in suppressing TLR7/8 dependent cell responses. Since an IRC may comprise more than one IRP, IRPs with various activities can be combined to create an IRC with a particular activity for a particular use.

In some instances, the combination of two IRPs in an IRC leads to an immunoregulatory activity of the IRC different from either of the IRPs alone. For example, IRC SEQ ID NO:68 (C913 contains IRP SEQ ID NO:33 (C917) linked to IRP SEQ ID NO:17 (C869) through a HEG moiety. IRP SEQ ID NO:33 (C917) inhibits TLR-7/8 dependent cell responses but not TLR-9 dependent cell responses. IRP SEQ ID NO:17 (C869) have greater inhibitory activity for TLR-9 dependent cell responses than for TLR-7/8 dependent cell responses. The IRC SEQ ID NO:68 (C913) however is very active in inhibiting both TLR-7/8 dependent cell responses and TLR-9 dependent cell responses. The same is also true for IRC SEQ ID NO:69 (C914) and its component IRPs SEQ ID NO:34 (C918) and SEQ ID NO:17 (C869).

The IRCs comprise one or more non-nucleic acid spacer moieties covalently bound to the nucleic acid moieties. For convenience, non-nucleic acid spacer moieties are sometimes referred to herein simply as "spacers" or "spacer moieties." Spacers are generally of molecular weight about 50 to about 50,000, typically from about 75 to about 5000, most often from about 75 to about 500, which are covalently bound, in various embodiments, to one, two, three, or more than three nucleic acid moieties. A variety of agents are suitable for connecting nucleic acid moieties. For example, a variety of compounds referred to in the scientific literature as "non-nucleic acid linkers," "non-nucleotidic linkers," or "valency platform molecules" may be used as spacers in an IRC. In certain embodiments, a spacer comprises multiple covalently connected subunits and may have a homopolymeric or heteropolymeric structure. It will be appreciated that mononucleotides and polynucleotides are not included in the definition of non-nucleic acid spacers, without which exclusion there would be no difference between nucleic acid moiety and an adjacent non-nucleic acid spacer moiety.

In certain embodiments, a spacer may comprise one or more abasic nucleotides (i.e., lacking a nucleotide base, but having the sugar and phosphate portions). Exemplary abasic nucleotides include 1'2'-dideoxyribose, 1'-deoxyribose, 1'-deoxyarabinose and polymers thereof.

Other suitable spacers comprise optionally substituted alkyl, optionally substituted polyglycol, optionally substituted polyamine, optionally substituted polyalcohol, optionally substituted polyamide, optionally substituted polyether, optionally substituted polyimine, optionally substituted polyphosphodiester (such as poly(1-phospho-3-propanol), and the like. Optional substituents include alcohol, alkoxy (such as methoxy, ethoxy, and propoxy), straight or branched chain alkyl (such as C1-C12 alkyl), amine, aminoalkyl (such as amino C1-C12 alkyl), phosphoramidite, phosphate, thiophosphate, hydrazide, hydrazine, halogen, (such as F, Cl, Br, or I), amide, alkylamide (such as amide C1-C12 alkyl), carboxylic acid, carboxylic ester, carboxylic anhydride, carboxylic acid halide, sulfonyl halide, imidate ester, isocyanate, isothiocyanate, haloformate, carbodiimide adduct, aldehydes, ketone, sulfhydryl, haloacetyl, alkyl halide, alkyl sulfonate, NR1R2 wherein R1R2 is —C(=O)CH=CHC(=O) (maleimide), thioether, cyano, sugar (such as mannose, galactose, and glucose), α,β-unsaturated carbonyl, alkyl mercurial, α,β-unsaturated sulfone.

Suitable spacers may comprise polycyclic molecules, such as those containing phenyl or cyclohexyl rings. The spacer may be a polyether such as polyphosphopropanediol, polyethyleneglycol, polypropylene glycol, a bifunctional polycyclic molecule such as a bifunctional pentalene, indene, naphthalene, azulene, heptalene, biphenylene, asymindacene, sym-indacene, acenaphthylene, fluorene, phenalene, phenanthrene, anthracene, fluoranthene, acephenathrylene, aceanthrylene, triphenylene, pyrene, chrysene, naphthacene, thianthrene, isobenzofuran, chromene, xanthene, phenoxathiin, which may be substituted or modified, or a combination of the polyethers and the polycyclic molecules. The polycyclic molecule may be substituted or polysubstituted with C1-C5 alkyl, C6 alkyl, alkenyl, hydroxyalkyl, halogen or haloalkyl group. Nitrogen-containing polyheterocyclic molecules (e.g., indolizine) are typically not suitable spacers. The spacer may also be a polyalcohol, such as glycerol or pentaerythritol. In one embodiment, the spacer comprises 1-phosphopropane$_3$-phosphate or 1-phosphopropane$_4$-phosphate (also called tetraphosphopropanediol and pentaphosphopropanediol). In one embodiment, the spacer comprises derivatized 2,2'-ethylenedioxydiethylamine (EDDA).

Specific examples of non-nucleic acid spacers useful in IRCs include "linkers" described by Cload et al. (1991) *J. Am. Chem. Soc.* 113:6324; Richardson et al. (1991) *J. Am. Chem. Soc.* 113:5109; Ma et al. (1993) *Nucleic Acids Res.* 21:2585; Ma et al. (1993) *Biochemistry* 32:1751; McCurdy et al. (1991) *Nucleosides & Nucleotides* 10:287; Jaschke et al. (1993) *Tetrahedron Lett.* 34:301; Ono et al. (1991) *Biochemistry* 30:9914; and International Publication No. WO 89/02439.

Other suitable spacers include linkers described by Salunkhe et al. (1992) *J. Am. Chem. Soc.* 114:8768; Nelson et al. (1996) *Biochemistry* 35:5339-5344; Bartley et al. (1997) *Biochemistry* 36:14502-511; Dagneaux et al. (1996) *Nucleic Acids Res.* 24:4506-12; Durand et al. (1990) *Nucleic Acids Res.* 18:6353-59; Reynolds et al. (1996) *Nucleic Acids Res.* 24:760-65; Hendry et al. (1994) *Biochem. Biophys. Acta* 1219:405-12; Altmann et al. (1995) *Nucleic Acids Res.*

23:4827-35. Still other suitable spacers are described in European Pat. No. EP0313219B1 and U.S. Pat. No. 6,117,657.

Exemplary non-nucleic acid spacers comprise oligo-ethylene glycol (e.g., triethylene glycol, tetraethylene glycol, hexaethylene glycol spacers, and other polymers comprising up to about 10, about 20, about 40, about 50, about 100 or about 200 ethylene glycol units), alkyl spacers (e.g., propyl, butyl, hexyl, and other C2-C12 alkyl spacers, e.g., usually C2-C10 alkyl, most often C2-C6 alkyl), abasic nucleotide spacers, symmetric or asymmetric spacers derived from glycerol, pentaerythritol or 1,3,5-trihydroxycyclohexane (e.g., symmetrical doubler and trebler spacer moieties described herein). Spacers can also comprise heteromeric or homomeric oligomers and polymers of the aforementioned compounds (e.g., linked by an amide, ester, ether, thioether, disulfide, phosphodiester, phosphorothioate, phosphoramidate, phosphotriester, phosphorodithioate, methyl phosphonate or other linkage).

Suitable spacer moieties can contribute charge and/or hydrophobicity to the IRC, contribute favorable pharmacokinetic properties (e.g., improved stability, longer residence time in blood) to the IRC, and/or result in targeting of the IRC to particular cells or organs. Spacer moieties can be selected or modified to tailor the IRC for desired pharmacokinetic properties or suitability for desired modes of administration (e.g., oral administration). It will be appreciated by the reader that, for convenience, a spacer (or spacer component) is sometimes referred to by the chemical name of the compound from which the spacer component is derived (e.g., hexaethylene glycol), with the understanding that the IRC actually comprises the conjugate of the compound and adjacent nucleic acid moieties or other spacer moiety components.

In an IRC comprising more than one spacer moiety, the spacers may be the same or different. Thus, in one embodiment all of the non-nucleic acid spacer moieties in an IRC have the same structure. In one embodiment, an IRC comprises non-nucleic acid spacer moieties with at least 2, at least 3, at least 4, at least 5, or at least 6 or more different structures.

In some contemplated embodiments of the invention, the spacer moiety of an IRC is defined to exclude certain structures. Thus, in some embodiments of the invention, a spacer is other than an abasic nucleotide or polymer of abasic nucleotides. In some embodiments of the invention, a spacer is other than a oligo(ethyleneglycol) (e.g., HEG, TEG and the like) or poly(ethyleneglycol). In some embodiments a spacer is other than a C3 alkyl spacer. In some embodiments, a spacer is other than a polypeptide. Thus, in some embodiments, an immunogenic molecule, e.g., a protein or polypeptide, is not suitable as a component of spacer moieties. However, as discussed infra, it is contemplated that in certain embodiments, an IRC is a "proteinaceous IRC" i.e., comprising a spacer moiety comprising a polypeptide. However, in some embodiments, the spacer moiety is not proteinaceous and/or is not an antigen (i.e., the spacer moiety, if isolated from the IRC, is not an antigen).

Generally, suitable spacer moieties do not render the IRC of which they are a component insoluble in an aqueous solution (e.g., PBS, pH 7.0). Thus, the definition of spacers excludes microcarriers or nanocarriers. In addition, a spacer moiety that has low solubility, such as a dodecyl spacer (solubility <5 mg/ml when measured as dialcohol precursor 1,12-dihydroxydodecane) is not preferred because it can reduce the hydrophilicity and activity of the IRC. Preferably, spacer moieties have solubility much greater than 5 mg/ml (e.g., ≥20 mg/ml, ≥50 mg/ml or ≥100 mg/ml) when measured as dialcohol precursors.

The charge of an IRC may be contributed by phosphate, thiophosphate, or other groups in the nucleic acid moieties as well as groups in non-nucleic acid spacer moieties. In some embodiments of the invention, a non-nucleic acid spacer moiety carries a net charge (e.g., a net positive charge or net negative charge when measured at pH 7). In one useful embodiment, the IRC has a net negative charge. In some embodiments, the negative charge of a spacer moiety in an IRC is increased by derivatizing a spacer subunit described herein to increase its charge. For example, glycerol can be covalently bound to two nucleic acid moieties and the remaining alcohol can be reacted with an activated phosphoramidite, followed by oxidation or sulfurization to form a phosphate or thiophosphate, respectively. In certain embodiments the negative charge contributed by the non-nucleic acid spacer moieties in an IRC (i.e., the sum of the charges when there is more than one spacer) is greater than the negative charge contributed by the nucleic acid moieties of the IRC. Charge can be calculated based on molecular formula, or determined experimentally, e.g., by capillary electrophoresis (Li, ed., 1992, *Capillary electrophoresis, Principles, Practice and Application* Elsevier Science Publishers, Amsterdam, The Netherlands, pp 202-206).

As is noted supra, suitable spacers can be polymers of smaller non-nucleic acid (e.g., non-nucleotide) compounds, such as those described herein, that are themselves useful as spacers, including compounds commonly referred to as non-nucleotide "linkers." Such polymers (i.e., "multiunit spacers") may be heteromeric or homomeric, and often comprise monomeric units (e.g., HEG, TEG, glycerol, 1'2'-dideoxyribose, and the like) linked by an ester linkage (e.g., phosphodiester or phosphorothioate ester). Thus, in one embodiment the spacer comprises a polymeric (e.g., heteropolymeric) structure of non-nucleotide units (e.g., from 2 to about 100 units, alternatively 2 to about 50, e.g., 2 to about 5, alternatively e.g., about 5 to about 50, e.g., about 5 to about 20).

For illustration, IRCs containing SEQ ID NO:17 (C869) and multiunit spacers include

```
                                       (SEQ ID NO: 115)
    5'-TCCTGGAGGGGTTGT-(C3)15-T (SEQ ID NO: 116)
    5'-TCCTGGAGGGGTTGT-(glycerol)15-T (SEQ ID NO: 117)
    5'-TCCTGGAGGGGTTGT-(TEG)8-T (SEQ ID NO: 118)
    5'-TCCTGGAGGGGTTGT-(HEG)4-T
``` where $(C3)_{15}$ means 15 propyl linkers connected via phosphorothioate esters; $(glycerol)_{15}$ means 15 glycerol linkers connected via phosphorothioate esters; $(TEG)_8$ means 8 triethyleneglycol linkers connected via phosphorothioate esters; and $(HEG)_4$ means 4 hexaethyleneglycol linkers connected via phosphorothioate esters. It will be appreciated that certain multiunit spacers have a net negative charge, and that the negative charge can be increased by increasing the number of e.g., ester-linked monomeric units.

In certain embodiments, a spacer moiety is a multivalent non-nucleic acid spacer moiety (i.e., a "multivalent spacer"). As used in this context, an IRC containing a multivalent spacer contains a spacer covalently bound to three (3) or more nucleic acid moieties. Multivalent spacers are sometimes referred to in the art as "platform molecules." Multivalent spacers can be polymeric or nonpolymeric. Examples of suitable molecules include glycerol or substituted glycerol (e.g., 2-hydroxymethyl glycerol, levulinyl-glycerol); tetraminobenzene, heptaminobetacyclodextrin, 1,3,5-trihydroxycyclohexane, pentaerythritol and derivatives of pentaerythritol, tetraminopentaerythritol, 1,4,8,11-tetraazacyclo tetradecane (Cyclam), 1,4,7,10-tetraazacyclododecane (Cyclen), polyethyleneimine, 1,3-diamino-2-propanol and substituted derivatives, propyloxymethyl]ethyl compounds (e.g., "trebler"), polyethylene glycol derivatives such as so-called "Star PEGs" and "bPEG" (see, e.g., Gnanou et al. (1988) *Makromol. Chem.* 189:2885; Rein et al. (1993) *Acta Polymer* 44:225; U.S. Pat. No. 5,171,264), and dendrimers.

Dendrimers are known in the art and are chemically defined globular molecules, generally prepared by stepwise or reiterative reaction of multifunctional monomers to obtain a branched structure (see, e.g., Tomalia et al. (1990) *Angew. Chem. Int. Ed. Engl.* 29:138-75). A variety of dendrimers are known, e.g., amine-terminated polyamidoamine, polyethyleneimine and polypropyleneimine dendrimers. Exemplary dendrimers useful in the present invention include "dense star" polymers or "starburst" polymers such as those described in U.S. Pat. Nos. 4,587,329; 5,338,532; and 6,177,414, including so-called "poly(amidoamine) ("PAMAM") dendrimers." Still other multimeric spacer molecules suitable for use within the present invention include chemically-defined, non-polymeric valency platform molecules such as those disclosed in U.S. Pat. No. 5,552,391; and PCT application publications WO 00/75105, WO 96/40197, WO 97/46251, WO 95/07073, and WO 00/34231. Many other suitable multivalent spacers can be used and will be known to those of skill in the art.

Conjugation of a nucleic acid moiety to a platform molecule can be effected in any number of ways, typically involving one or more crosslinking agents and functional groups on the nucleic acid moiety and platform molecule. Linking groups are added to platforms using standard synthetic chemistry techniques. Linking groups can be added to nucleic acid moieties using standard synthetic techniques.

Multivalent spacers with a variety of valencies are useful in the practice of the invention, and in various embodiments the multivalent spacer of an IRC is bound to between about 3 and about 400 nucleic acid moieties, often from 3 to 100, sometimes from 3-50, frequently from 3-10, and sometimes more than 400 nucleic acid moieties. In various embodiments, the multivalent spacer is conjugated to more than 10, more than 25, more than 50, or more than 500 nucleic acid moieties (which may be the same or different). It will be appreciated that, in certain embodiments in which an IRC comprises a multivalent spacer, the invention provides a population of IRCs with slightly different molecular structures. For example, when an IRC is prepared using a dendrimer as a high valency the multivalent spacer, a somewhat heterogeneous mixture of molecules is produced, i.e., comprising different numbers (within or predominantly within a determinable range) of nucleic acid moieties joined to each dendrimer molecule.

Polysaccharides derivatized to allow linking to nucleic acid moieties can be used as spacers in IRCs. Suitable polysaccharides include naturally occurring polysaccharides (e.g., dextran) and synthetic polysaccharides (e.g., ficoll). For instance, aminoethylcarboxymethyl-ficoll (AECM-Ficoll) can be prepared by the method of Inman (1975) *J. Imm.* 114:704-709. AECM-Ficoll can then be reacted with a heterobifunctional crosslinking reagent, such as 6-maleimido caproic acyl N-hydroxysuccinimide ester, and then conjugated to a thiol-derivatized nucleic acid moiety (see Lee et al. (1980) *Mol. Imm.* 17:749-56). Other polysaccharides may be modified similarly.

It will be well within the ability of one of skill, guided by this specification and knowledge in the art, to prepare IRCs using routine methods. Techniques for making nucleic acid moieties (e.g., oligonucleotides and modified oligonucleotides) are known. Nucleic acid moieties can be synthesized using techniques including, but not limited to, enzymatic methods and chemical methods and combinations of enzymatic and chemical approaches. For example, DNA or RNA containing phosphodiester linkages can be chemically synthesized by sequentially coupling the appropriate nucleoside phosphoramidite to the 5'-hydroxy group of the growing oligonucleotide attached to a solid support at the 3'-end, followed by oxidation of the intermediate phosphite triester to a phosphate triester. Useful solid supports for DNA synthesis include Controlled Pore Glass (Applied Biosystems, Foster City, Calif.), polystyrene bead matrix (Primer Support, Amersham Pharmacia, Piscataway, N.J.) and TentGel (Rapp Polymere GmbH, Tubingen, Germany). Once the desired oligonucleotide sequence has been synthesized, the oligonucleotide is removed from the support, the phosphate triester groups are deprotected to phosphate diesters and the nucleoside bases are deprotected using aqueous ammonia or other bases.

For instance, DNA or RNA polynucleotides (nucleic acid moieties) containing phosphodiester linkages are generally synthesized by repetitive iterations of the following steps: a) removal of the protecting group from the 5'-hydroxyl group of the 3'-solid support-bound nucleoside or nucleic acid, b) coupling of the activated nucleoside phosphoramidite to the 5'-hydroxyl group, c) oxidation of the phosphite triester to the phosphate triester, and d) capping of unreacted 5'-hydroxyl groups. DNA or RNA containing phosphorothioate linkages is prepared as described above, except that the oxidation step is replaced with a sulfurization step. Once the desired oligonucleotide sequence has been synthesized, the oligonucleotide is removed from the support, the phosphate triester groups are deprotected to phosphate diesters and the nucleoside bases are deprotected using aqueous ammonia or other bases. See, for example, Beaucage (1993) "Oligodeoxyribonucleotide Synthesis" in PROTOCOLS FOR OLIGONUCLEOTIDES AND ANALOGS, SYNTHESIS AND PROPERTIES (Agrawal, ed.) Humana Press, Totowa, N.J.; Warner et al. (1984) *DNA* 3:401; Tang et al. (2000) *Org. Process Res. Dev.* 4:194-198; Wyrzykiewica et al. (1994) *Bioorg. & Med. Chem. Lett.* 4:1519-1522; Radhakrishna et al. (1989) *J. Org. Chem.* 55:4693-4699. and U.S. Pat. No. 4,458,066. Programmable machines that automatically synthesize nucleic acid moieties of specified sequences are widely available. Examples include the Expedite 8909 automated DNA synthesizer (Perseptive Biosystem, Framington Mass.); the ABI 394 (Applied Biosystems, Inc., Foster City, Calif.); and the OligoPilot II (Amersham Pharmacia Biotech, Piscataway, N.J.).

Polynucleotides can be assembled in the 3' to 5' direction, e.g., using base-protected nucleosides (monomers) containing an acid-labile 5'-protecting group and a 3'-phosphoramidite. Examples of such monomers include 5'-O-(4,4'-dimethoxytrityl)-protected nucleoside-3'-O-(N,N-diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine. In this case, the solid support used contains a 3'-linked protected nucleoside. Alternatively, polynucleotides can be assembled in the 5' to 3' direction using base-protected nucleosides containing an acid-labile 3'-protecting group and a 5'-phosphoramidite. Examples of such monomers include 3'-O-(4,4'-dimethoxytrityl)-protected nucleoside-5'-O-(N,N- diisopropylamino) 2-cyanoethyl phosphoramidite, where examples of the protected nucleosides include, but are not limited to, N6-benzoyladenosine, N4-benzoylcytidine, N2-isobutryrylguanosine, thymidine, and uridine (Glen Research, Sterling, Va.). In this case, the solid support used contains a 5'-linked protected nucleoside. Circular nucleic acid components can be isolated, synthesized through recombinant methods, or chemically synthesized. Chemical synthesis can be performed using any method described in the literature. See, for instance, Gao et al. (1995) *Nucleic Acids Res.* 23:2025-2029 and Wang et al. (1994) *Nucleic Acids Res.* 22:2326-2333.

Addition of non-nucleic acid spacer moieties can be accomplished using routine methods. Methods for addition of particular spacer moieties are known in the art and, for example, are described in the references cited supra. See, e.g., Durand et al. (1990) *Nucleic Acids Res.* 18:6353-6359. The covalent linkage between a spacer moiety and nucleic acid moiety can be any of a number of types, including phosphodiester, phosphorothioate, amide, ester, ether, thioether, disulfide, phosphoramidate, phosphotriester, phosphorodithioate, methyl phosphonate and other linkages. It will often be convenient to combine a spacer moiety(s) and a nucleic acid moiety(s) using the same phosphoramidite-type chemistry used for synthesis of the nucleic acid moiety. For example, IRCs of the invention can be conveniently synthesized using an automated DNA synthesizer (e.g., Expedite 8909; Perseptive Biosystems, Framington, Mass.) using phosphoramidite chemistry (see, e.g., Beaucage, 1993, supra; *Current Protocols in Nucleic Acid Chemistry, supra*). However, one of skill will understand that the same (or equivalent) synthesis steps carried out by an automated DNA synthesizer can also be carried out manually, if desired. In such a synthesis, typically, one end of the spacer (or spacer subunit for multimeric spacers) is protected with a 4,4'-dimethyoxytrityl group, while the other end contains a phosphoramidite group.

A variety of spacers with the requisite protecting and reacting groups are commercially available, for example:

| | |
|---|---|
| triethylene glycol spacer or "TEG spacer" | 9-O-(4,4'-dimethoxytrityl)triethyleneglycol-1-O-[(2-cyanoethyl) N,N-diisopropylphosphoramidite] (Glen Research, 22825 Davis Drive, Sterling, VA) |
| hexaethylene glycol spacer or "HEG spacer" | 18-O-(4,4'-dimethoxytrityl)hexaethyleneglycol-1-O-[(2-cyanoethyl) N,N-diisopropylphosphoramidite](Glen Research, Sterling, VA) |
| propyl spacer | 3-(4,4'-dimethoxytrityloxy)propyloxy-1-O-[(2-cyanoethyl) N,N-diisopropylphosphoramidite] (Glen Research, Sterling, VA); |
| butyl spacer | 4-(4,4'-dimethoxytrityloxy)butyloxy-1-O-[(2-cyanoethyl) N,N-diisopropylphosphoramidite] (Chem Genes Corporation, Ashland Technology Center, 200 Homer Ave, Ashland, MA) |
| Hexyl spacer | 6-(4,4'-dimethoxytrityloxy)hexyloxy-1-O-[(2-cyanoethyl) N,N-diisopropylphosphoramidite] |
| 2-(hydroxymethyl)ethyl spacer or "HME spacer" | 1-(4,4'-dimethoxytrityloxy)-3-(levulinyloxy)-propyloxy-2-O-[(2-cyanoethyl) N,N-diisopropylphosphoramidite]; also called "asymmetrical branched" spacer |
| "abasic nucleotide spacer" or "abasic spacer" | 5-O-(4,4'-dimethoxytrityl)-1,2-dideoxyribose-3-O-[(2-cyanoethyl) N,N-diisopropylphosphoramidite] (Glen Research, Sterling, VA) |
| "symmetrical branched spacer" or "glycerol spacer" | 1,3-O,O-bis(4,4'-dimethoxytrityl)glycerol-2-O-[(2-cyanoethyl) N,N-diisopropylphosphoramidite] (Chem Genes, Ashland, MA) |
| "trebler spacer" | 2,2,2-O,O,O-tris[3-O-(4,4'-dimethoxytrityloxy)propyloxymethyl]ethyl-1-O-[(2-cyanoethyl) N,N-diisopropylphosphoramidite] (Glen Research, Sterling, VA) |
| "symmetrical doubler spacer" | 1,3-O,O-bis[5-O-(4,4'-dimethoxytrityloxy)pentylamido]propyl-2-O-[(2-cyanoethyl) N,N-diisopropylphosphoramidite] (Glen Research, Sterling, VA) |
| "dodecyl spacer" | 12-(4,4'-dimethoxytrityloxy)dodecyloxy-1-O-[(2-cyanoethyl) N,N-diisopropylphosphoramidite] (Glen Research, Sterling, VA) |

These and a large variety of other protected spacer moiety precursors (e.g., comprising DMT and phosphoramidite group protecting groups) can be purchased or can be synthesized using routine methods for use in preparing IRCs disclosed herein. The instrument is programmed according to the manufacturer's instructions to add nucleotide monomers and spacers in the desired order.

Although use of phosphoramidite chemistry is convenient for the preparation of certain IRCs, it will be appreciated that the IRCs of the invention are not limited to compounds prepared by any particular method of synthesis or preparation.

In one embodiment, IRCs with multivalent spacers conjugated to more than one type of nucleic acid moiety are prepared. For instance, platforms containing two maleimide groups (which can react with thiol-containing polynucleotides), and two activated ester groups (which can react with amino-containing nucleic acids) have been described (see, e.g., PCT application publication WO 95/07073). These two activated groups can be reacted independently of each other. This would result in an IRC containing a total of 4 nucleic acid moieties, two of each sequence.

IRCs with multivalent spacers containing two different nucleic acid sequences can also be prepared using the symmetrical branched spacer, described above, and conventional phosphoramidite chemistry (e.g., using manual or automated methods). The symmetrical branched spacer contains a phosphoramidite group and two protecting groups that are the same and are removed simultaneously. In one approach, for example, a first nucleic acid is synthesized and coupled to the symmetrical branched spacer, the protecting groups are removed from the spacer. Then two additional nucleic acids (of the same sequence) are synthesized on the spacer (using double the amount of reagents used for synthesis of a single nucleic acid moiety in each step).

A similar method can be used to connect three different nucleic acid moieties (referred to below as Nucleic acids I, II, and III) to a multivalent platform (e.g., asymmetrical branched spacer). This is most conveniently carried out using an automated DNA synthesizer. In one embodiment, the asymmetrical branched spacer contains a phosphoramidite group and two orthogonal protecting groups that can be removed independently. First, nucleic acid I is synthesized, then the asymmetrical branched spacer is coupled to nucleic acid I, then nucleic acid II is added after the selective removal of one of the protecting groups. Nucleic acid II is deprotected, and capped, and then the other protecting group on the spacer is removed. Finally, nucleic acid III is synthesized.

In some embodiments, a nucleic acid moiety(s) is synthesized, and a reactive linking group (e.g., amino, carboxylate, thio, disulfide, and the like) is added using standard synthetic chemistry techniques. The reactive linking group (which is considered to form a portion of the resulting spacer moiety) is conjugated to additional non-nucleic acid compounds to form the spacer moiety. Linking groups are added to nucleic acids using standard methods for nucleic acid synthesis, employing a variety of reagents described in the literature or commercially available. Examples include reagents that contain a protected amino group, carboxylate group, thiol group, or disulfide group and a phosphoramidite group. Once these compounds are incorporated into the nucleic acids, via the activated phosphoramidite group, and are deprotected, they provide nucleic acids with amino, carboxylate, or thiol reactivity.

Hydrophilic linkers of variable lengths are useful, for example to link nucleic acids moieties and platform molecules. A variety of suitable linkers are known. Suitable linkers include, without limitation, linear oligomers or polymers of ethylene glycol. Such linkers include linkers with the formula $R^1S(CH_2CH_2O)_nCH_2CH_2O\ (CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleimide, etc., via a thioether to a second molecule which contains an amino group via an amide bond. The order of attachment can vary, i.e., the thioether bond can be formed before or after the amide bond is formed. Other useful linkers include Sulfo-SMCC (sulfosuccinimidyl 4-[N-maleimidomethyl]-cyclohexane-1-carboxylate) Pierce Chemical Co. product 22322; Sulfo-EMCS(N[ε-maleimidocaproyloxy]sulfosuccinimide ester) Pierce Chemical Co. product 22307; Sulfo-GMBS (N-[γ-maleimidobutyryloxy]sulfosuccinimide ester) Pierce Chemical Co. product 22324 (Pierce Chemical Co., Rockford, Ill.), and similar compounds of the general formula maleimido-R—C(O)NHS ester, where R=alkyl, cyclic alkyl, polymers of ethylene glycol, and the like.

Particularly useful methods for covalently joining nucleic acid moieties to multivalent spacers are described in the references cited supra.

In certain embodiments, a polypeptide is used as a multivalent spacer moiety to which a plurality of nucleic acid moieties are covalently conjugated, directly or via linkers, to form a "proteinaceous IRC." The polypeptide can be a carrier (e.g., albumin). Typically, a proteinaceous IRC comprises at least one, and usually several or many nucleic acid moieties that (a) are between 2 and 7, more often between 4 and 7 nucleotides in length, alternatively between 2 and 6, 2 and 5, 4 and 6, or 4 and 5 nucleotides in length and/or (b) have inferior isolated immunomodulatory activity or do not have isolated immunomodulatory activity. Methods of making a proteinaceous IRC will be apparent to one of skill upon review of the present disclosure. A nucleic acid, for example, can be covalently conjugated to a polypeptide spacer moiety by art known methods including linkages between a 3' or 5' end of a nucleic acid moiety (or at a suitably modified base at an internal position in the a nucleic acid moiety) and a polypeptide with a suitable reactive group (e.g., an N-hydroxysuccinimide ester, which can be reacted directly with the $N^4$ amino group of cytosine residues). As a further example, a polypeptide can be attached to a free 5'-end of a nucleic acid moiety through an amine, thiol, or carboxyl group that has been incorporated into nucleic acid moiety. Alternatively, the polypeptide can be conjugated to a spacer moiety, as described herein. Further, a linking group comprising a protected amine, thiol, or carboxyl at one end, and a phosphoramidite can be covalently attached to a hydroxyl group of a polynucleotide, and, subsequent to deprotection, the functionality can be used to covalently attach the IRC to a peptide.

IRP and/or IRC Complexes and Compositions

IRPs or IRCs can be directly administered to the individual or they can be administered in a composition or complex to enhance IRP or IRC delivery to cells and/or uptake by cells. Compositions or complexes can also be use to enhance co-delivery of two of more different IRP and/or IRC species to a cell. In certain embodiments, a mixture of IRCs and IRPs may be complexed so as to deliver at least one IRC and IRP species. Such delivery compositions or complexes include, but are not limited to, encapsulating complexes and colloidal dispersion systems as described herein and known in the art. Examples of such delivery compositions include oil-in-water emulsions, micelles, and liposomes. Delivery compositions or complexes also include IRP and/or IRC linked to a linker molecules, a platform molecule, a nanoparticle or a microparticle, as described herein. Such linkages include both covalent and non-covalent linkages. Unless otherwise noted, complex and composition formulations described herein for use with IRPs are also appropriate for use with IRCs.

In some embodiments, the IRP and/or IRC is conjugated with a linker molecule. The IRP and/or IRC portion can be coupled with the linker portion of a conjugate in a variety of ways, including covalent and/or non-covalent interactions.

The link between the portions can be made at the 3' or 5' end of the IRP and/or IRC, or at a suitably modified base at an internal position in the IRP and/or IRC. If the linker is a peptide and contains a suitable reactive group (e.g., an N-hydroxysuccinimide ester) it can be reacted directly with the $N^4$ amino group of cytosine residues. Depending on the number and location of cytosine residues in the IRP and/or IRC, specific coupling at one or more residues can be achieved.

Alternatively, modified oligonucleosides, such as are known in the art, can be incorporated at either terminus, or at internal positions in the IRP and/or IRC. These can contain blocked functional groups which, when deblocked, are reactive with a variety of functional groups which can be present on, or attached to, the linker of interest.

Where the linker is a peptide, this portion of the conjugate can be attached to the 3'-end of the IRP and/or IRC through solid support chemistry. For example, the IRP portion can be added to a peptide portion that has been pre-synthesized on a support. Haralambidis et al. (1990a) *Nucleic Acids Res.* 18:493-499; and Haralambidis et al. (1990b) *Nucleic Acids Res.* 18:501-505. Alternatively, the IRP can be synthesized such that it is connected to a solid support through a cleavable linker extending from the 3'-end. Upon chemical cleavage of the IRP from the support, a terminal thiol group is left at the 3'-end of the oligonucleotide (Zuckermann et al. (1987) *Nucleic Acids Res.* 15:5305-5321; and Corey et al. (1987) *Science* 238:1401-1403) or a terminal amino group is left at the 3'-end of the oligonucleotide (Nelson et al. (1989) *Nucleic Acids Res.* 17:1781-1794). Conjugation of the amino-modified IRP and/or IRC to amino groups of the peptide can be performed as described in Benoit et al. (1987) *Neuromethods* 6:43-72. Conjugation of the thiol-modified IRP and/or IRC to carboxyl groups of the peptide can be performed as described in Sinah et al. (1991) *Oligonucleotide Analogues: A Practical Approach*, IRL Press. Coupling of an oligonucleotide carrying an appended maleimide to the thiol side chain of a cysteine residue of a peptide has also been described. Tung et al. (1991) *Bioconjug. Chem.* 2:464-465.

The peptide linker portion of the conjugate can be attached to the 5'-end of the IRP and/or IRC through an amine, thiol, or carboxyl group that has been incorporated into the oligonucleotide during its synthesis. Preferably, while the oligonucleotide is fixed to the solid support, a linking group comprising a protected amine, thiol, or carboxyl at one end, and a phosphoramidite at the other, is covalently attached to the 5'-hydroxyl. Agrawal et al. (1986) *Nucleic Acids Res.* 14:6227-6245; Connolly (1985) *Nucleic Acids Res.* 13:4485-

4502; Kremsky et al. (1987) *Nucleic Acids Res.* 15:2891-2909; Connolly (1987) *Nucleic Acids Res.* 15:3131-3139; Bischoff et al. (1987) *Anal. Biochem.* 164:336-344; Blanks et al. (1988) *Nucleic Acids Res.* 16:10283-10299; and U.S. Pat. Nos. 4,849,513, 5,015,733, 5,118,800, and 5,118,802. Subsequent to deprotection, the amine, thiol, and carboxyl functionalities can be used to covalently attach the oligonucleotide to a peptide. Benoit et al. (1987); and Sinah et al. (1991).

An IRP and/or IRC conjugate can also be formed through non-covalent interactions, such as ionic bonds, hydrophobic interactions, hydrogen bonds and/or van der Waals attractions.

Non-covalently linked conjugates can include a non-covalent interaction such as a biotin-streptavidin complex. A biotinyl group can be attached, for example, to a modified base of an IRP and/or IRC. Roget et al. (1989) *Nucleic Acids Res.* 17:7643-7651. Incorporation of a streptavidin moiety into the peptide portion allows formation of a non-covalently bound complex of the streptavidin conjugated peptide and the biotinylated oligonucleotide.

Non-covalent associations can also occur through ionic interactions involving an IRP and/or IRC through the use of a linker portion comprising charged residues that can interact with an oligonucleotide. For example, non-covalent conjugation can occur between a generally negatively-charged IRP and/or IRC and positively-charged amino acid residues of a peptide linker, e.g., polylysine, polyarginine and polyhistidine residues.

The linkage of the IRP and/or IRC to a lipid can be formed using standard methods. These methods include, but are not limited to, the synthesis of oligonucleotide-phospholipid conjugates (Yanagawa et al. (1988) *Nucleic Acids Symp. Ser.* 19:189-192), oligonucleotide-fatty acid conjugates (Grabarek et al. (1990) *Anal. Biochem.* 185:131-135; and Staros et al. (1986) *Anal. Biochem.* 156:220-222), and oligonucleotide-sterol conjugates. Boujrad et al. (1993) *Proc. Natl. Acad. Sci. USA* 90:5728-5731.

The linkage of the oligonucleotide to an oligosaccharide can be formed using standard known methods. These methods include, but are not limited to, the synthesis of oligonucleotide-oligosaccharide conjugates, wherein the oligosaccharide is a moiety of an immunoglobulin. O'Shannessy et al. (1985) *J. Applied Biochem.* 7:347-355.

The linkage of a circular IRP and/or IRC to a peptide linker can be formed in several ways. Where the circular IRP and/or IRC is synthesized using recombinant or chemical methods, a modified nucleoside is suitable. Ruth (1991) in *Oligonucleotides and Analogues: A Practical Approach*, IRL Press. Standard linking technology can then be used to connect the circular IRP and/or IRC to the peptide. Goodchild (1990) *Bioconjug. Chem.* 1:165. Where the circular IRP and/or IRC is isolated, or synthesized using recombinant or chemical methods, the linkage can be formed by chemically activating, or photoactivating, a reactive group (e.g. carbene, radical) that has been incorporated into the peptide.

Additional methods for the attachment of peptides and other molecules to oligonucleotides can be found in U.S. Pat. No. 5,391,723; Kessler (1992) "Nonradioactive labeling methods for nucleic acids" in Kricka (ed.) *Nonisotopic DNA Probe Techniques*, Academic Press; and Geoghegan et al. (1992) *Bioconjug. Chem.* 3:138-146.

An IRP and/or IRC may be proximately associated in other ways. In some embodiments, an IRP and/or IRC are proximately associated by encapsulation. In other embodiments, an IRP and/or IRC are proximately associated by linkage to a platform molecule. A "platform molecule" (also termed "platform") is a molecule containing sites which allow for attachment of the IRP and/or IRC. In other embodiments, an IRP and/or IRC are proximately associated by adsorption onto a surface, preferably a carrier particle.

In some embodiments, the methods of the invention employ an encapsulating agent in association with the IRP and/or IRC. Preferably, the composition comprising IRP and/or IRC and encapsulating agent is in the form of adjuvant oil-in-water emulsions, microparticles and/or liposomes. More preferably, adjuvant oil-in-water emulsions, microparticles and/or liposomes encapsulating an IRP and/or IRC are in the form of particles from about 0.04 µm to about 100 µm in size, preferably any of the following ranges: from about 0.1 µm to about 20 µm; from about 0.15 µm to about 10 µm; from about 0.05 µm to about 1.00 µm; from about 0.05 µm to about 0.5 µm.

Colloidal dispersion systems, such as microspheres, beads, macromolecular complexes, nanocapsules and lipid-based system, such as oil-in-water emulsions, micelles, mixed micelles and liposomes can provide effective encapsulation of IRP and/or IRC-containing compositions.

The encapsulation composition further comprises any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Polypeptides suitable for encapsulation components include any known in the art and include, but are not limited to, fatty acid binding proteins. Modified polypeptides contain any of a variety of modifications, including, but not limited to glycosylation, phosphorylation, myristylation, sulfation and hydroxylation. As used herein, a suitable polypeptide is one that will protect an IRP and/or IRC-containing composition to preserve the immunoregulatory activity thereof. Examples of binding proteins include, but are not limited to, albumins such as bovine serum albumin (BSA) and pea albumin.

Other suitable polymers can be any known in the art of pharmaceuticals and include, but are not limited to, naturally-occurring polymers such as dextrans, hydroxyethyl starch, and polysaccharides, and synthetic polymers. Examples of naturally occurring polymers include proteins, glycopeptides, polysaccharides, dextran and lipids. The additional polymer can be a synthetic polymer. Examples of synthetic polymers which are suitable for use in the present invention include, but are not limited to, polyalkyl glycols (PAG) such as PEG, polyoxyethylated polyols (POP), such as polyoxyethylated glycerol (POG), polytrimethylene glycol (PTG) polypropylene glycol (PPG), polyhydroxyethyl methacrylate, polyvinyl alcohol (PVA), polyacrylic acid, polyethyloxazoline, polyacrylamide, polyvinylpyrrolidone (PVP), polyamino acids, polyurethane and polyphosphazene. The synthetic polymers can also be linear or branched, substituted or unsubstituted, homopolymeric, co-polymers, or block co-polymers of two or more different synthetic monomers.

The PEGs for use in encapsulation compositions of the present invention are either purchased from chemical suppliers or synthesized using techniques known to those of skill in the art.

The term "LMS", as used herein, means lamellar lipid particles wherein polar head groups of a polar lipid are arranged to face an aqueous phase of an interface to form membrane structures. Examples of the LMSs include liposomes, micelles, cochleates (i.e., generally cylindrical liposomes), microemulsions, unilamellar vesicles, multilamellar vesicles, and the like.

An optional colloidal dispersion system of this invention is a liposome. As used herein, a "liposome" or "lipid vesicle" is a small vesicle bounded by at least one and possibly more than one bilayer lipid membrane. Liposomes are made artificially from phospholipids, glycolipids, lipids, steroids such as cholesterol, related molecules, or a combination thereof by any technique known in the art, including but not limited to sonication, extrusion, or removal of detergent from lipid-detergent complexes. A liposome can also optionally comprise additional components, such as a tissue targeting component. It is understood that a "lipid membrane" or "lipid bilayer" need not consist exclusively of lipids, but can additionally contain any suitable other components, including, but not limited to, cholesterol and other steroids, lipid-soluble hemicals, proteins of any length, and other amphipathic molecules, providing the general structure of the membrane is a sheet of two hydrophilic surfaces sandwiching a hydrophobic core. For a general discussion of membrane structure, see *The Encyclopedia of Molecular Biology* by J. Kendrew (1994). For suitable lipids see e.g., Lasic (1993) "Liposomes: from Physics to Applications" Elsevier, Amsterdam.

Processes for preparing liposomes containing IRP and/or IRC compositions are known in the art. The lipid vesicles can be prepared by any suitable technique known in the art. Methods include, but are not limited to, microencapsulation, microfluidization, LLC method, ethanol injection, freon injection, the "bubble" method, detergent dialysis, hydration, sonication, and reverse-phase evaporation. Reviewed in Watwe et al. (1995) *Curr. Sci.* 68:715-724. Techniques may be combined in order to provide vesicles with the most desirable attributes.

The invention encompasses use of LMSs containing tissue or cellular targeting components. Such targeting components are components of a LMS that enhance its accumulation at certain tissue or cellular sites in preference to other tissue or cellular sites when administered to an intact animal, organ, or cell culture. A targeting component is generally accessible from outside the liposome, and is therefore preferably either bound to the outer surface or inserted into the outer lipid bilayer. A targeting component can be inter alia a peptide, a region of a larger peptide, an antibody specific for a cell surface molecule or marker, or antigen binding fragment thereof, a nucleic acid, a carbohydrate, a region of a complex carbohydrate, a special lipid, or a small molecule such as a drug, hormone, or hapten, attached to any of the aforementioned molecules. Antibodies with specificity toward cell type-specific cell surface markers are known in the art and are readily prepared by methods known in the art.

The LMSs can be targeted to any cell type toward which a therapeutic treatment is to be directed, e.g., a cell type which can regulate and/or participate in an immune response. Such target cells and organs include, but are not limited to, APCs, such as macrophages, dendritic cells and lymphocytes, lymphatic structures, such as lymph nodes and the spleen, and nonlymphatic structures, particularly those in which dendritic cells are found.

The LMS compositions of the present invention can additionally comprise surfactants. Surfactants can be cationic, anionic, amphiphilic, or nonionic. A preferred class of surfactants are nonionic surfactants; particularly preferred are those that are water soluble.

In some embodiments in which an IRP and/or IRC are proximately associated by linkage to a platform molecule, the platform may be proteinaceous or non-proteinaceous (i.e., organic). Examples of proteinaceous platforms include, but are not limited to, albumin, gammaglobulin, immunoglobulin (IgG) and ovalbumin. Borel et al. (1990) *Immunol. Methods* 126:159-168; Dumas et al. (1995) *Arch. Dematol. Res.* 287: 123-128; Borel et al. (1995) *Int. Arch. Allergy Immunol.* 107: 264-267; Borel et al. (1996) *Ann. N.Y. Acad. Sci.* 778:80-87.

A platform is multi-valent (i.e., contains more than one binding, or linking, site) to accommodate binding to more than 1 IRP and/or IRC. Accordingly, a platform may contain 2 or more, 3 or more, 4 or more, 5 or more, 6 or more, 7 or more, 8 or more, 9 or more, 10 or more binding or linking sites Other examples of polymeric platforms are dextran, polyacrylamide, ficoll, carboxymethylcellulose, polyvinyl alcohol, and poly D-glutamic acid/D-lysine.

The principles of using platform molecules are well understood in the art. Generally, a platform contains, or is derivatized to contain, appropriate binding sites for IRP and/or IRC. In addition, or alternatively, IRP and/or IRC is derivatized to provide appropriate linkage groups. For example, a simple platform is a bi-functional linker (i.e., has two binding sites), such as a peptide. Further examples are discussed below.

Platform molecules may be biologically stabilized, i.e., they exhibit an in vivo excretion half-life often of hours to days to months to confer therapeutic efficacy, and are preferably composed of a synthetic single chain of defined composition. They generally have a molecular weight in the range of about 200 to about 1,000,000, preferably any of the following ranges: from about 200 to about 500,000; from about 200 to about 200,000; from about 200 to about 50,000 (or less, such as 30,000). Examples of valency platform molecules are polymers (or are comprised of polymers) such as polyethylene glycol (PEG; preferably having a molecular weight of about 200 to about 8000), poly-D-lysine, polyvinyl alcohol, polyvinylpyrrolidone, D-glutamic acid and D-lysine (in a ratio of 3:2). Other molecules that may be used are albumin and IgG.

Other platform molecules suitable for use within the present invention are the chemically-defined, non-polymeric valency platform molecules disclosed in U.S. Pat. No. 5,552, 391. Other homogeneous chemically-defined valency platform molecules suitable for use within the present invention are derivatized 2,2'-ethylenedioxydiethylamine (EDDA) and triethylene glycol (TEG).

Additional suitable valency platform molecules include, but are not limited to, tetraminobenzene, heptaminobetacyclodextrin, tetraminopentaerythritol, 1,4,8,11-tetraazacyclotetradecane (Cyclam) and 1,4,7,10-tetraazacyclododecane (Cyclen).

In general, these platforms are made by standard chemical synthesis techniques. PEG must be derivatized and made multivalent, which is accomplished using standard techniques. Some substances suitable for conjugate synthesis, such as PEG, albumin, and IgG are available commercially.

Conjugation of an IRP and/or IRC to a platform molecule may be effected in any number of ways, typically involving one or more crosslinking agents and functional groups on the IRP and/or IRC and platform molecule. Platforms and IRP and/or IRC must have appropriate linking groups. Linking groups are added to platforms using standard synthetic chemistry techniques. Linking groups may be added to polypeptide platforms and IRP and/or IRC using either standard solid phase synthetic techniques or recombinant techniques. Recombinant approaches may require post-translational modification in order to attach a linker, and such methods are known in the art.

As an example, polypeptides contain amino acid side chain moieties containing functional groups such as amino, carboxyl or sulfhydryl groups that serve as sites for coupling the polypeptide to the platform. Residues that have such functional groups may be added to the polypeptide if the polypeptide does not already contain these groups. Such residues may be incorporated by solid phase synthesis techniques or recombinant techniques, both of which are well known in the peptide synthesis arts. When the polypeptide has a carbohydrate side chain(s) (or if the platform is a carbohydrate), functional amino, sulfhydryl and/or aldehyde groups may be incorporated therein by conventional chemistry. For instance, primary amino groups may be incorporated by reaction of the oxidized sugar with ethylenediamine in the presence of sodium cyanoborohydride, sulfhydryls may be introduced by reaction of cysteamine dihydrochloride followed by reduction with a standard disulfide reducing agent, while aldehyde groups may be generated following periodate oxidation. In a similar fashion, the platform molecule may also be derivatized to contain functional groups if it does not already possess appropriate functional groups.

Hydrophilic linkers of variable lengths are useful for connecting IRP and/or IRC to platform molecules. Suitable linkers include linear oligomers or polymers of ethylene glycol. Such linkers include linkers with the formula $R^1S(CH_2CH_2O)_nCH_2CH_2O(CH_2)_mCO_2R^2$ wherein n=0-200, m=1 or 2, $R^1$=H or a protecting group such as trityl, $R^2$=H or alkyl or aryl, e.g., 4-nitrophenyl ester. These linkers are useful in connecting a molecule containing a thiol reactive group such as haloaceyl, maleiamide, etc., via a thioether to a second molecule which contains an amino group via an amide bond. These linkers are flexible with regard to the order of attachment, i.e., the thioether can be formed first or last.

In embodiments in which an IRP and/or IRC are proximately associated by adsorption onto a surface, the surface may be in the form of a carrier particle (for example, a nanoparticle) made with either an inorganic or organic core. Examples of such nanoparticles include, but are not limited to, nanocrystalline particles, nanoparticles made by the polymerization of alkylcyanoacrylates and nanoparticles made by the polymerization of methylidene malonate. Additional surfaces to which an IRP and/or IRC may be adsorbed include, but are not limited to, activated carbon particles and protein-ceramic nanoplates. Other examples of carrier particles are provided herein.

Adsorption of polynucleotides and polypeptides to a surface for the purpose of delivery of the adsorbed molecules to cells is well known in the art. See, for example, Douglas et al. (1987) *Crit. Rev. Ther. Drug. Carrier Syst.* 3:233-261; Hagiwara et al. (1987) *In Vivo* 1:241-252; Bousquet et al. (1999) *Pharm. Res.* 16:141-147; and Kossovsky et al., U.S. Pat. No. 5,460,831. Preferably, the material comprising the adsorbent surface is biodegradable. Adsorption of an IRP and/or IRC to a surface may occur through non-covalent interactions, including ionic and/or hydrophobic interactions.

In general, characteristics of carriers such as nanoparticles, such as surface charge, particle size and molecular weight, depend upon polymerization conditions, monomer concentration and the presence of stabilizers during the polymerization process (Douglas et al., 1987). The surface of carrier particles may be modified, for example, with a surface coating, to allow or enhance adsorption of the IRP and/or IRC. Carrier particles with adsorbed IRP and/or IRC may be further coated with other substances. The addition of such other substances may, for example, prolong the half-life of the particles once administered to the subject and/or may target the particles to a specific cell type or tissue, as described herein.

Nanocrystalline surfaces to which an IRP and/or IRC may be adsorbed have been described (see, for example, U.S. Pat. No. 5,460,831). Nanocrystalline core particles (with diameters of 1 μm or less) are coated with a surface energy modifying layer that promotes adsorption of polypeptides, polynucleotides and/or other pharmaceutical agents. Another adsorbent surface are nanoparticles made by the polymerization of alkylcyanoacrylates. Alkylcyanoacrylates can be polymerized in acidified aqueous media by a process of anionic polymerization. Depending on the polymerization conditions, the small particles tend to have sizes in the range of 20 to 3000 nm, and it is possible to make nanoparticles specific surface characteristics and with specific surface charges (Douglas et al., 1987). For example, oligonucleotides may be adsorbed to polyisobutyl- and polyisohexlcyanoacrylate nanoparticles in the presence of hydrophobic cations such as tetraphenylphosphonium chloride or quaternary ammonium salts, such as cetyltrimethyl ammonium bromide. Oligonucleotide adsorption on these nanoparticles appears to be mediated by the formation of ion pairs between negatively charged phosphate groups of the nucleic acid chain and the hydrophobic cations. See, for example, Lambert et al. (1998) *Biochimie* 80:969-976, Chavany et al. (1994) *Pharm. Res.* 11:1370-1378; Chavany et al. (1992) *Pharm. Res.* 9:441-449. Another adsorbent surface are nanoparticles made by the polymerization of methylidene malonate.

IRPs or IRCs may be administered in the form of microcarrier (MC) complexes. Accordingly, the invention provides compositions comprising IRP/MC complexes or IRC/MC complexes. IRP/MC complexes comprise an IRP bound to the surface of a microcarrier (i.e., the IRP is not encapsulated in the MC), and preferably comprise multiple molecules of IRP bound to each microcarrier. In certain embodiments, a mixture of different IRPs may be complexed with a microcarrier, such that the microcarrier is bound to more than one IRP species. The bond between the IRP and MC may be covalent or non-covalent. As will be understood by one of skill in the art, the IRP may be modified or derivatized and the composition of the microcarrier may be selected and/or modified to accommodate the desired type of binding desired for IRP/MC complex formation. This same description applies for IRC/MC complexes. In certain embodiments, a mixture of IRCs and IRPs may be complexed with a microcarrier, such that the microcarrier is bound to at least one IRC and IRP species.

Microcarriers useful in the invention are less than about 150, 120 or 100 μm in size, more commonly less than about 50-60 μm in size, preferably less than about 10 μm in size, and are insoluble in pure water. Microcarriers used in the invention are preferably biodegradable, although nonbiodegradable microcarriers are acceptable. Microcarriers are commonly solid phase, such as "beads" or other particles, although liquid phase microcarriers such as oil in water emulsions comprising a biodegradable polymers or oils are also contemplated. A wide variety of biodegradable and nonbiodegradable materials acceptable for use as microcarriers are known in the art.

Microcarriers for use in the compositions or methods of the invention are generally less than about 10 μm in size (e.g., have an average diameter of less than about 10 μm, or at least about 97% of the particles pass through a 10 μm screen filter), and include nanocarriers (i.e., carriers of less than about 1 μm size). Preferably, microcarriers are selected having sizes within an upper limit of about 9, 7, 5, 2, or 1 μm or 900, 800, 700, 600, 500, 400, 300, 250, 200, or 100 nm and an independently selected lower limit of about 4, 2, or 1 μm or about 800, 600, 500, 400, 300, 250, 200, 150, 100, 50, 25, or 10 nm, where the lower limit is less than the upper limit. In some embodiments, the microcarriers have a size of about 1.0-1.5 μm, about 1.0-2.0 μm or about 0.9-1.6 μm. In certain preferred embodiments, the microcarriers have a size of about 10 nm to about 5 μm or about 25 nm to about 4.5 μm, about 1 μm, about 1.2 μm, about 1.4 μm, about 1.5 μm, about 1.6 μm, about 1.8 μm, about 2.0 μm, about 2.5 μm or about 4.5 μm. When the microcarriers are nanocarriers, preferred embodiments include nanocarriers of about 25 to about 300 nm, 50 to about 200 nm, about 50 nm or about 200 nm.

Solid phase biodegradable microcarriers may be manufactured from biodegradable polymers including, but not limited to: biodegradable polyesters, such as poly(lactic acid), poly (glycolic acid), and copolymers (including block copolymers) thereof, as well as block copolymers of poly(lactic acid) and poly(ethylene glycol); polyorthoesters such as polymers based on 3,9-diethylidene-2,4,8,10-tetraoxaspiro [5.5]undecane (DETOSU); polyanhydrides such as poly(anhydride) polymers based on relatively hydrophilic monomers such as sebacic acid; polyanhydride imides, such as polyanhydride polymers based on sebacic acid-derived monomers incorporating amino acids (i.e., linked to sebacic acid by imide bonds through the amino-terminal nitrogen) such as glycine or alanine; polyanhydride esters; polyphosphazenes, especially poly(phosphazenes) which contain hydrolysis-sensitive ester groups which can catalyze degradation of the polymer backbone through generation of carboxylic acid groups (Schacht et al., (1996) *Biotechnol. Bioeng.* 1996:102); and polyamides such as poly(lactic acid-co-lysine).

A wide variety of nonbiodegradable materials suitable for manufacturing microcarriers are also known, including, but not limited to polystyrene, polypropylene, polyethylene, silica, ceramic, polyacrylamide, dextran, hydroxyapatite, latex, gold, and ferromagnetic or paramagnetic materials. Certain embodiments exclude gold, latex, and/or magnetic beads. In certain embodiments, the microcarriers may be made of a first material (e.g., a magnetic material) encapsulated with a second material (e.g., polystyrene).

Solid phase microspheres are prepared using techniques known in the art. For example, they can be prepared by emulsion-solvent extraction/evaporation technique. Generally, in this technique, biodegradable polymers such as polyanhydrates, poly(alkyl-α-cyanoacrylates) and poly(α-hydroxy esters), for example, poly(lactic acid), poly(glycolic acid), poly(D,L-lactic-co-glycolic acid) and poly(caprolactone), are dissolved in a suitable organic solvent, such as methylene chloride, to constitute the dispersed phase (DP) of emulsion. DP is emulsified by high-speed homogenization into excess volume of aqueous continuous phase (CP) that contains a dissolved surfactant, for example, polyvinylalcohol (PVA) or polyvinylpirrolidone (PVP). Surfactant in CP is to ensure the formation of discrete and suitably-sized emulsion droplet. The organic solvent is then extracted into the CP and subsequently evaporated by raising the system temperature. The solid microparticles are then separated by centrifugation or filtration, and dried, for example, by lyophilization or application of vacuum, before storing at 4° C.

Physico-chemical characteristics such as mean size, size distribution and surface charge of dried microspheres may be determined. Size characteristics are determined, for example, by dynamic light scattering technique and the surface charge was determined by measuring the zeta potential.

Liquid phase microcarriers include liposomes, micelles, oil droplets and other lipid or oil-based particles which incorporate biodegradable polymers or oils. In certain embodiments, the biodegradable polymer is a surfactant. In other embodiments, the liquid phase microcarriers are biodegradable due to the inclusion of a biodegradable oil such as squalene or a vegetable oil. One preferred liquid phase microcarrier is oil droplets within an oil-in-water emulsion. Preferably, oil-in-water emulsions used as microcarriers comprise biodegradable substituents such as squalene.

Covalently bonded IRP/MC complexes may be linked using any covalent crosslinking technology known in the art. Typically, the IRP portion will be modified, either to incorporate an additional moiety (e.g., a free amine, carboxyl or sulfhydryl group) or incorporate modified (e.g., phosphorothioate) nucleotide bases to provide a site at which the IRP portion may be linked to the microcarrier. The link between the IRP and MC portions of the complex can be made at the 3' or 5' end of the IRP, or at a suitably modified base at an internal position in the IRP. The microcarrier is generally also modified to incorporate moieties through which a covalent link may be formed, although functional groups normally present on the microcarrier may also be utilized. The IRP/MC is formed by incubating the IRP with a microcarrier under conditions which permit the formation of a covalent complex (e.g., in the presence of a crosslinking agent or by use of an activated microcarrier comprising an activated moiety which will form a covalent bond with the IRP).

A wide variety of crosslinking technologies are known in the art, and include crosslinkers reactive with amino, carboxyl and sulfhydryl groups. As will be apparent to one of skill in the art, the selection of a crosslinking agent and crosslinking protocol will depend on the configuration of the IRP and the microcarrier as well as the desired final configuration of the IRP/MC complex. The crosslinker may be either homobifunctional or heterobifunctional. When a homobifunctional crosslinker is used, the crosslinker exploits the same moiety on the IRP and MC (e.g., an aldehyde crosslinker may be used to covalently link an IRP and MC where both the IRP and MC comprise one or more free amines). Heterobifunctional crosslinkers utilize different moieties on the IRP and MC, (e.g., a maleimido-N-hydroxysuccinimide ester may be used to covalently link a free sulfhydryl on the IRP and a free amine on the MC), and are preferred to minimize formation of inter-microcarrier bonds. In most cases, it is preferable to crosslink through a first crosslinking moiety on the microcarrier and a second crosslinking moiety on the IRP, where the second crosslinking moiety is not present on the microcarrier. One preferred method of producing the IRP/MC complex is by 'activating' the microcarrier by incubating with a heterobifunctional crosslinking agent, then forming the IRP/MC complex by incubating the IRP and activated MC under conditions appropriate for reaction. The crosslinker may incorporate a "spacer" arm between the reactive moieties, or the two reactive moieties in the crosslinker may be directly linked.

In one preferred embodiment, the IRP portion comprises at least one free sulfhydryl (e.g., provided by a 5'-thiol modified base or linker) for crosslinking to the microcarrier, while the microcarrier comprises free amine groups. A heterobifunctional crosslinker reactive with these two groups (e.g., a crosslinker comprising a maleimide group and a NHS-ester), such as succinimidyl 4-(N-maleimidomethyl)cyclohexane-1-carboxylate is used to activate the MC, then covalently crosslink the IRP to form the IRP/MC complex.

Non-covalent IRP/MC complexes may be linked by any non-covalent binding or interaction, including ionic (electrostatic) bonds, hydrophobic interactions, hydrogen bonds, van der Waals attractions, or a combination of two or more different interactions, as is normally the case when a binding pair is to link the IRP and MC.

Preferred non-covalent IRP/MC complexes are typically complexed by hydrophobic or electrostatic (ionic) interactions, or a combination thereof, (e.g., through base pairing between an IRP and a polynucleotide bound to an MC use of a binding pair). Due to the hydrophilic nature of the backbone of polynucleotides, IRP/MC complexes which rely on hydrophobic interactions to form the complex generally require modification of the IRP portion of the complex to incorporate a highly hydrophobic moiety. Preferably, the hydrophobic moiety is biocompatible, nonimmunogenic, and is naturally occurring in the individual for whom the composition is intended (e.g., is found in mammals, particularly humans). Examples of preferred hydrophobic moieties include lipids, steroids, sterols such as cholesterol, and terpenes. The method of linking the hydrophobic moiety to the IRP will, of course, depend on the configuration of the IRP and the identity of the hydrophobic moiety. The hydrophobic moiety may be added at any convenient site in the IRP, preferably at either the 5' or 3' end; in the case of addition of a cholesterol moiety to an IRP, the cholesterol moiety is preferably added to the 5' end of the IRP, using conventional chemical reactions (see, for example, Godard et al. (1995) Eur. J. Biochem. 232:404-410). Preferably, microcarriers for use in IRP/MC complexes linked by hydrophobic bonding are made from hydrophobic materials, such as oil droplets or hydrophobic polymers, although hydrophilic materials modified to incorporate hydrophobic moieties may be utilized as well. When the microcarrier is a liposome or other liquid phase microcarrier comprising a lumen and the IRP is desired to be associated with the outer surface of the MC, the IRP/MC complex is formed by mixing the IRP and the MC after preparation of the MC, in order to avoid encapsulation of the IRP during the MC preparation process.

Non-covalent IRP/MC complexes bound by electrostatic binding typically exploit the highly negative charge of the polynucleotide backbone. Accordingly, microcarriers for use in non-covalently bound IRP/MC complexes are generally positively charged (cationic) at physiological pH (e.g., about pH 6.8-7.4). The microcarrier may intrinsically possess a positive charge, but microcarriers made from compounds not normally possessing a positive charge may be derivatized or otherwise modified to become positively charged (cationic). For example, the polymer used to make the microcarrier may be derivatized to add positively charged groups, such as primary amines. Alternately, positively charged compounds may be incorporated in the formulation of the microcarrier during manufacture (e.g., positively charged surfactants may be used during the manufacture of poly(lactic acid)/poly(glycolic acid) copolymers to confer a positive charge on the resulting microcarrier particles).

For example, to prepare cationic microspheres, cationic lipids or polymers, for example, 1,2-dioleoyl-1,2,3-trimethylammoniopropane (DOTAP), cetyltrimethylammonium bromide (CTAB) or polylysine, are added either to DP or CP, as per their solubility in these phases.

IRP/MC complexes can be preformed by adsorption onto cationic microspheres by incubation of polynucleotide and the particles, preferably in an aqueous admixture. Such incubation may be carried out under any desired conditions, including ambient (room) temperature (e.g., approximately 20° C.) or under refrigeration (e.g., 4° C.). Because cationic microspheres and polynucleotides associate relatively quickly, the incubation may be for any convenient time period, such as 5, 10, 15 minutes or more, including overnight and longer incubations. For example, IRPs can be adsorbed onto the cationic microspheres by overnight aqueous incubation of polynucleotide and the particles at 4° C. However, because cationic microspheres and polynucleotides spontaneously associate, the IRP/MC complex can be formed by simple co-administration of the polynucleotide and the MC. Microspheres may be characterized for size and surface charge before and after polynucleotide association. Selected batches may then evaluated for activity against suitable controls in, for example, human peripheral blood mononuclear cell (PBMC) and mouse splenocyte assays. The formulations may also evaluated in suitable animal models.

Non-covalent IRP/MC complexes linked by nucleotide base pairing may be produced using conventional methodologies. Generally, base-paired IRP/MC complexes are produced using a microcarrier comprising a bound, preferably a covalently bound, polynucleotide (the "capture polynucleotide") that is at least partially complementary to the IRP. The segment of complementarity between the IRP and the capture nucleotide is preferably at least 6, 8, 10 or 15 contiguous base pairs, more preferably at least 20 contiguous base pairs. The capture nucleotide may be bound to the MC by any method known in the art, and is preferably covalently bound to the IRP at the 5' or 3' end. In some embodiments, an IRP comprising a 5'-GGGG-3' sequence will retain this portion of the sequence as single-stranded.

In other embodiments, a binding pair may be used to link the IRP and MC in an IRP/MC complex. The binding pair may be a receptor and ligand, an antibody and antigen (or epitope), or any other binding pair which binds at high affinity (e.g., Kd less than about 10-8). One type of preferred binding pair is biotin and streptavidin or biotin and avidin, which form very tight complexes. When using a binding pair to mediate IRP/MC complex binding, the IRP is derivatized, typically by a covalent linkage, with one member of the binding pair, and the MC is derivatized with the other member of the binding pair. Mixture of the two derivatized compounds results in IRP/MC complex formation.

Methods of the Invention

The invention provides methods of regulating an immune response in an individual, preferably a mammal, more preferably a human, comprising administering to the individual an IRS-containing polynucleotide as described herein. Methods of immunoregulation provided by the invention include those that suppress and/or inhibit an innate immune response, including, but not limited to, an immune response stimulated by immunostimulatory nucleic acid molecules such as bacterial DNA. The invention also provides methods for inhibiting TLR7/8 and/or TLR9 induced cell response. The invention also provides methods for ameliorating symptoms associated with unwanted immune activation, including, but not limited to, symptoms associated with autoimmunity.

The IRS-containing polynucleotide is administered in an amount sufficient to regulate an immune response. As described herein, regulation of an immune response may be humoral and/or cellular, and is measured using standard techniques in the art and as described herein.

In certain embodiments, the individual suffers from a disorder associated with unwanted immune activation, such as allergic disease or condition, allergy and asthma. An individual having an allergic disease or asthma is an individual with a recognizable symptom of an existing allergic disease or asthma.

In certain embodiments, the individual suffers from a disorder associated with unwanted immune activation, such as autoimmune disease and inflammatory disease. An individual having an autoimmune disease or inflammatory disease is an individual with a recognizable symptom of an existing autoimmune disease or inflammatory disease.

Autoimmune diseases can be divided in two broad categories: organ-specific and systemic. Autoimmune diseases include, without limitation, rheumatoid arthritis (RA), systemic lupus erythematosus (SLE), type I diabetes mellitus, type II diabetes mellitus, multiple sclerosis (MS), immune-mediated infertility such as premature ovarian failure, scleroderma, Sjogren's disease, vitiligo, alopecia (baldness), polyglandular failure, Grave's disease, hypothyroidism, polymyositis, pemphigus vulgaris, pemphigus foliaceus, inflammatory bowel disease including Crohn's disease and ulcerative colitis, autoimmune hepatitis including that associated with hepatitis B virus (HBV) and hepatitis C virus (HCV), hypopituitarism, graft-versus-host disease (GvHD), myocarditis, Addison's disease, autoimmune skin diseases, uveitis, pernicious anemia, and hypoparathyroidism.

Autoimmune diseases may also include, without limitation, Hashimoto's thyroiditis, Type I and Type II autoimmune polyglandular syndromes, paraneoplastic pemphigus, bullus pemphigoid, dermatitis herpetiformis, linear IgA disease, epidermolysis bullosa acquisita, erythema nodosa, pemphigoid gestationis, cicatricial pemphigoid, mixed essential cryoglobulinemia, chronic bullous disease of childhood, hemolytic anemia, thrombocytopenic purpura, Goodpasture's syndrome, autoimmune neutropenia, myasthenia gravis, Eaton-Lambert myasthenic syndrome, stiff-man syndrome, acute disseminated encephalomyelitis, Guillain-Barre syndrome, chronic inflammatory demyelinating polyradiculoneuropathy, multifocal motor neuropathy with conduction block, chronic neuropathy with monoclonal gammopathy, opsonoclonus-myoclonus syndrome, cerebellar degeneration, encephalomyelitis, retinopathy, primary biliary sclerosis, sclerosing cholangitis, gluten-sensitive enteropathy, ankylosing spondylitis, reactive arthritides, polymyositis/dermatomyositis, mixed connective tissue disease, Bechet's syndrome, psoriasis, polyarteritis nodosa, allergic anguitis and granulomatosis (Churg-Strauss disease), polyangiitis overlap syndrome, hypersensitivity vasculitis, Wegener's granulomatosis, temporal arteritis, Takayasu's arteritis, Kawasaki's disease, isolated vasculitis of the central nervous system, thromboangiutis obliterans, sarcoidosis, glomerulonephritis, and cryopathies. These conditions are well known in the medical arts and are described, for example, in Harrison's Principles of Internal Medicine, 14th ed., Fauci A S et al., eds., New York: McGraw-Hill, 1998.

The systemic disease SLE is characterized by the presence of antibodies to antigens that are abundant in nearly every cell, such as anti-chromatin antibodies, anti-splicesosome antibodies, anti-ribosome antibodies and anti-DNA antibodies. Consequently, the effects of SLE are seen in a variety of tissues, such as the skin and kidneys. Autoreactive T cells also play a role in SLE. For example, studies in a murine lupus model have shown that non-DNA nucleosomal antigens, e.g. histones, stimulate autoreactive T cells that can drive anti-DNA producing B cells. Increased serum levels of IFN-α has been observed in SLE patients and shown to correlate with both disease activity and severity, including fever and skin rashes, as well as essential markers associated with the disease process (e.g., anti-dsDNA antibody titers). It has also been shown that immune complexes present in the circulation could trigger IFN-α in these patients and, thus, maintain this chronic presence of elevated IFN-α. Two different types of immune complexes have been described to trigger IFN-α from human PDC: DNA/anti-DNA antibody complexes and RNA/anti-ribonucleoprotein-RNA antibody complexes. Because DNA is a ligand of TLR-9 and RNA a ligand for TLR-7/8, it is expected that these two pathways utilize TLR-9 and TLR-7/8 signalling, respectively, in order to chronically induce IFN-α and thus participate in the etiopathogenesis of SLE. Accordingly, IRP and/or IRC compositions which are effective in inhibiting TLR-7/8 and TLR-9 responses may be particularly effective in treating SLE.

In certain embodiments, an individual is at risk of developing an autoimmune disease and an IRP or IRC is administered in an amount effective to delay or prevent the autoimmune disease. Individuals at risk of developing an autoimmune disease includes, for example, those with a genetic or other predisposition toward developing an autoimmune disease. In humans, susceptibility to particular autoimmune diseases is associated with HLA type with some being linked most strongly with particular MHC class II alleles and others with particular MHC class I alleles. For example, ankylosing spondylitis, acute anterior uveitis, and juvenile rheumatoid arthritis are associated with HLA-B27, Goodpasture's syndrome and MS are associated with HLA-DR2, Grave's disease, myasthenia gravis and SLE are associated with HLA-DR3, rheumatoid arthritis and pemphigus vulgaris are associated with HLA-DR4 and Hashimoto's thyroiditis is associated with HLA-DR5. Other genetic predispositions to autoimmune diseases are known in the art and an individual can be examined for existence of such predispositions by assays and methods well known in the art. Accordingly, in some instances, an individual at risk of developing an autoimmune can be identified.

As described herein, IRPs of the invention may particularly inhibit production of a cytokine, including, but not limited to, IL-6, IL-12, TNF-α, and/or IFN-α, and may suppress B cell proliferation and/or activation of plasmacytoid dendritic cells to differentiate. Accordingly, the IRPs and IRCs of the invention are particularly effective in suppressing an immune response to an immunostimulatory nucleic acid in an individual.

Animal models for the study of autoimmune disease are known in the art. For example, animal models which appear most similar to human autoimmune disease include animal strains which spontaneously develop a high incidence of the particular disease. Examples of such models include, but are not limited to, the nonobeses diabetic (NOD) mouse, which develops a disease similar to type 1 diabetes, and lupus-like disease prone animals, such as New Zealand hybrid, MRL-Fas$^{lpr}$ and BXSB mice. Animal models in which an autoimmune disease has been induced include, but are not limited to, experimental autoimmune encephalomyelitis (EAE), which is a model for multiple sclerosis, collagen-induced arthritis (CIA), which is a model for rheumatoid arthritis, and experimental autoimmune uveitis (EAU), which is a model for uveitis. Animal models for autoimmune disease have also been created by genetic manipulation and include, for example, IL-2/IL-10 knockout mice for inflammatory bowel disease, Fas or Fas ligand knockout for SLE, and IL-1 receptor antagonist knockout for rheumatoid arthritis.

Accordingly, animal models standard in the art are available for the screening and/or assessment for activity and/or effectiveness of the methods and compositions of the invention for the treatment of autoimmune disorders.

In certain embodiments, the individual suffers from a disorder associated with a chronic inflammatory response. Administration of an IRP results in immunomodulation, decreasing levels of one or more innate immune response associated cytokines, which may result in a reduction of the inflammatory response. Immunoregulation of individuals with the unwanted immune response associated the described disorders results in a reduction or improvement in one or more of the symptoms of the disorder.

Other embodiments of the invention relate to immunoregulatory therapy of individuals having been exposed to or infected with a virus. Administration of an IRP or IRC to an individual having been exposed to or infected with a virus results in suppression of virus induced cytokine production. Cytokine produced in response to a virus can contribute to an environment favorable for viral infection. Suppression of the virus-induced cytokine production may serve to limit or prevent the viral infection.

In certain embodiments, the individual suffers from a disease or disorder associated with chronic pathogen stimulation, such as that associated with chronic viral infections and with malaria. IRP and/or IRC compositions which are effective in inhibiting TLR-7/8 responses may be particularly effective in treating disease and symptoms related to chronic pathogen stimulation.

The methods of the invention may be practiced in combination with other therapies which make up the standard of care for the disorder, such as administration of anti-inflammatory agents such as systemic corticosteroid therapy (e.g., cortisone).

In some situations, peripheral tolerance to an autoantigen is lost (or broken) and an autoimmune response ensues. For example, in an animal model for EAE, activation of antigen presenting cells (APCs) through the innate immune receptor TLR9 or TLR4 was shown to break self-tolerance and result in the induction of EAE (Waldner et al. (2004) *J. Clin. Invest.* 113:990-997).

Accordingly, in some embodiments, the invention provides methods for suppressing or reducing TLR9 dependent cell stimulation. Administration of an IRP results in suppression of TLR9 dependent cell responses, including decreased levels of one or more TLR9-associated cytokines. IRPs appropriate for use in suppressing TLR9 dependent cell stimulation are those IRP that inhibit or suppress cell responses associated with TLR9.

In some embodiments, the invention provides methods for suppressing or reducing TLR7/8 dependent cell stimulation. Administration of an IRP results in suppression of TLR7/8 dependent cell responses, including decreased levels of one or more TLR7/8-associated cytokines. IRPs appropriate for use in suppressing TLR7/8 dependent cell stimulation are those IRP that inhibit or suppress cell responses associated with TLR7/8.

As demonstrated herein, some IRP suppress both TLR9 dependent cell responses and TLR7/8 dependent cell responses. Some IRP suppress of TLR9 dependent cell responses but not TLR7/8 dependent cell responses. Some IRP suppress of TLR7/8 dependent cell responses but not TLR9 dependent cell responses. Accordingly, particular IRP can be administered to regulate particular immune responses.

Administration and Assessment of the Immune Response

The IRP or IRC can be administered in combination with other pharmaceutical agents, as described herein, and can be combined with a physiologically acceptable carrier thereof (and as such the invention includes these compositions). The IRP or IRC may be any of those described herein.

As with all compositions for modulation of an immune response, the effective amounts and method of administration of the particular IRP or IRC formulation can vary based on the individual, what condition is to be treated and other factors evident to one skilled in the art. Factors to be considered include whether or not the IRP or IRC will be administered with or covalently attached to a delivery molecule, route of administration and the number of doses to be administered. Such factors are known in the art and it is well within the skill of those in the art to make such determinations without undue experimentation. A suitable dosage range is one that provides the desired regulation of immune response (e.g., suppression of IFN-α or other cytokine production in response to an immunostimulatory nucleic acid). When suppression of an immune response to an immunostimulatory nucleic acid is desired, a suitable dosage range is one that provides the desired suppression of immune stimulation by the immunostimulatory nucleic acid. Generally, dosage is determined by the amount of IRP administered to the patient, rather than the overall quantity of IRP-containing composition administered. Useful dosage ranges of the IRP, given in amounts of IRP delivered, may be, for example, from about any of the following: 0.5 to 10 mg/kg, 1 to 9 mg/kg, 2 to 8 mg/kg, 3 to 7 mg/kg, 4 to 6 mg/kg, 5 mg/kg, 1 to 10 mg/kg, 5 to 10 mg/kg. The absolute amount given to each patient depends on pharmacological properties such as bioavailability, clearance rate and route of administration.

The effective amount and method of administration of the particular IRP or IRC formulation can vary based on the individual patient, desired result and/or type of disorder, the stage of the disease and other factors evident to one skilled in the art. The route(s) of administration useful in a particular application are apparent to one of skill in the art. Routes of administration include but are not limited to topical, dermal, transdermal, transmucosal, epidermal, parenteral, gastrointestinal, and naso-pharyngeal and pulmonary, including transbronchial and transalveolar. A suitable dosage range is one that provides sufficient IRP-containing composition to attain a tissue concentration of about 1-50 µM as measured by blood levels. The absolute amount given to each patient depends on pharmacological properties such as bioavailability, clearance rate and route of administration.

As described herein, tissues in which unwanted immune activation is occurring or is likely to occur are preferred targets for the IRP or IRC. Thus, administration of IRP or IRC to lymph nodes, spleen, bone marrow, blood, as well as tissue exposed to virus, are preferred sites of administration.

The present invention provides IRP or IRC formulations suitable for topical application including, but not limited to, physiologically acceptable implants, ointments, creams, rinses and gels. Exemplary routes of dermal administration are those which are least invasive such as transdermal transmission, epidermal administration and subcutaneous injection.

Transdermal administration is accomplished by application of a cream, rinse, gel, etc. capable of allowing the IRP or IRC to penetrate the skin and enter the blood stream. Compositions suitable for transdermal administration include, but are not limited to, pharmaceutically acceptable suspensions, oils, creams and ointments applied directly to the skin or incorporated into a protective carrier such as a transdermal device (so-called "patch"). Examples of suitable creams, ointments etc. can be found, for instance, in the Physician's Desk Reference. Transdermal transmission may also be accomplished by iontophoresis, for example using commercially available patches which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

Parenteral routes of administration include but are not limited to electrical (iontophoresis) or direct injection such as direct injection into a central venous line, intravenous, intramuscular, intraperitoneal, intradermal, or subcutaneous injection. Formulations of IRP or IRC suitable for parenteral administration are generally formulated in USP water or water for injection and may further comprise pH buffers, salts bulking agents, preservatives, and other pharmaceutically acceptable excipients. Immunoregulatory polynucleotide for parenteral injection may be formulated in pharmaceutically acceptable sterile isotonic solutions such as saline and phosphate buffered saline for injection.

Gastrointestinal routes of administration include, but are not limited to, ingestion and rectal routes and can include the use of, for example, pharmaceutically acceptable powders, pills or liquids for ingestion and suppositories for rectal administration.

Naso-pharyngeal and pulmonary administration include are accomplished by inhalation, and include delivery routes such as intranasal, transbronchial and transalveolar routes. The invention includes formulations of IRP or IRC suitable for administration by inhalation including, but not limited to, liquid suspensions for forming aerosols as well as powder forms for dry powder inhalation delivery systems. Devices suitable for administration by inhalation of IRP or IRC formulations include, but are not limited to, atomizers, vaporizers, nebulizers, and dry powder inhalation delivery devices.

As is well known in the art, solutions or suspensions used for the routes of administration described herein can include any one or more of the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

As is well known in the art, pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

As is well known in the art, sterile injectable solutions can be prepared by incorporating the active compound(s) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The above-mentioned compositions and methods of administration are meant to describe but not limit the methods of administering the formulations of IRPs and IRCs of the invention. The methods of producing the various compositions and devices are within the ability of one skilled in the art and are not described in detail here.

Analysis (both qualitative and quantitative) of the activity of an IRP or IRC in suppression of immune stimulation can be by any method described herein or known in the art, including, but not limited to, measuring suppression or a decrease in proliferation of specific cell populations such as B cells, measuring suppression of maturation of specific cell populations such as dendritic cells (including plasmacytoid dendritic cells) and T cells, and measuring suppression in production of cytokines such as, but not limited to, IFN-α, TNF-α, IL-6, and/or IL-12. Measurement of numbers of specific types of cells can be achieved, for example, with fluorescence-activated cell sorting (FACS). Measurement of maturation of particular populations of cells can be achieved by determining expression of markers, for example, cell surface markers, specific for particular stage of cell maturation. Cell marker expression can be measured, for example, by measuring RNA expression or measuring cell surface expression of the particular marker by, for example, FACS analysis. Measuring maturation of dendritic cells can be performed for instance as described in Hartmann et al. (1999) *Proc. Natl. Acad. Sci. USA* 96:9305-9310. Cytokine concentrations can be measured, for example, by ELISA. These and other assays to evaluate suppression of an immune response, including an innate immune response, are well known in the art.

Kits of the Invention

The invention provides kits. In certain embodiments, the kits of the invention generally comprise one or more containers comprising any IRP and/or IRC as described herein. The kits may further comprise a suitable set of instructions, generally written instructions, relating to the use of the IRP and/or IRC for any of the methods described herein (e.g., suppression of a response to an immunostimulatory nucleic acid, suppression of a TLR-7/8 and/or TLR-9 dependent response, ameliorating one or more symptoms of an autoimmune disease, ameliorating a symptom of chronic inflammatory disease, decreasing cytokine production in response to a virus).

The kits may comprise IRP and/or IRC packaged in any convenient, appropriate packaging. For example, if the IRP or IRC is a dry formulation (e.g., freeze dried or a dry powder), a vial with a resilient stopper is normally used, so that the IRP or IRC may be easily resuspended by injecting fluid through the resilient stopper. Ampoules with non-resilient, removable closures (e.g., sealed glass) or resilient stoppers are most conveniently used for liquid formulations of IRP or IRC. Also contemplated are packages for use in combination with a specific device, such as an inhaler, nasal administration device (e.g., an atomizer), a syringe or an infusion device such as a minipump.

The instructions relating to the use of IRP and/or IRC generally include information as to dosage, dosing schedule, and route of administration for the intended method of use. The containers of IRP or IRC may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

In some embodiments, kits of the invention comprise materials for production of IRP and/or IRC as complexes for administration, for example, encapsulation material, microcarrier complex material and so on. Generally, the kit includes separate containers of IRP or IRC and the complex material(s). The IRP or IRC and complexes are preferably supplied in a form which allows formation of IRP- or IRC-complex upon mixing of the supplied IRP or IRC and complex material. This configuration is preferred when the IRP- or IRC-complex is linked by non-covalent bonding. This configuration is also preferred when the IRP- or IRC-complex are to be crosslinked via a heterobifunctional crosslinker; either IRP/IRC or the complex is supplied in an "activated" form (e.g., linked to the heterobifunctional crosslinker such that a moiety reactive with the IRP/IRC is available).

The following Examples are provided to illustrate, but not limit, the invention.

EXAMPLES

Example 1

Regulation of Innate Immune Responses of Cells by IRS-Containing Polynucleotides Immunoregulatory polynucleotides (IRPs) (i.e., polynucleotides containing at least one IRS) or control samples were assayed for immunoregulatory (IR) activity of innate immune responses on human and mouse cells. IR activity was assayed by measurement of several indicators of innate immune response including cytokine response, cell maturation and cell proliferation. Unless noted otherwise, the polynucleotides tested were fully modified phosphorothioate oligodeoxynucleotides.

An innate immune response was stimulated in the cells being assayed by addition of an immunostimulatory nucleic acid (ISNA) to the cell culture. IRPs or control samples were then added to the cell culture. After incubation of the cells, the culture media and/or cells were tested for the level of a particular cytokine in the culture media, the state of cell maturation and/or cell proliferation.

For mouse cell assays, fragments of BALB/c or C57B1/6 mouse spleen were mechanically dispersed by forcing the digested fragments through metal screens. The dispersed splenocytes were pelleted by centrifugation, then resuspended in fresh medium (RPMI 1640 with 10% fetal calf serum, plus 50 units/mL penicillin, 50 µg/mL streptomycin, 2 mM glutamine, and 0.05 mM β-mercaptoethanol). For some assays, purified murine CD11c+ cells, isolated from the splenocytes using the CD11c-coated microbeads from Miltenyi Biotec (Auburn, Calif., catalogue number 130-052-501) and following the manufacturer guidelines, were used in the assays.

Mouse splenocytes were dispensed into wells of 96 well plates ($7 \times 10^7$ cells/ml). An ISNA, such as SEQ ID NO:119 (1018) or SEQ ID NO:99 (C274), was added to the cells at a concentration of 0.7 µM and the IRP test sample or control sample was added to the cells. The cells were incubated a further 48 hours. Medium was harvested from each well and tested for IL-6 and IL-12 cytokine concentrations using the immunoassay ELISA. To performed the ELISA, we used anti-IL-6 antibodies (Catalogue number 554400 and 554402, Pharmingen, SanDiego, Calif.) and anti-IL-12 antibodies (Catalogue number 551219 and 554476, Pharmingen, SanDiego) and used protocols recommended by the manufacturer. IRPs were tested at various concentrations including 1.4 µM, 0.7 µM, 0.14 µM and 0.07 µM or ratios of IRP:ISNA of 2:1, 1:1, 1:5, and 1:10. Other ratios were tested depending upon experimental design. Control samples included ISNA alone, IRP alone, media alone and a control oligonucleotide SEQ ID NO: 90 (C532) which contains neither ISNA nor IRS.

Figure 1B:
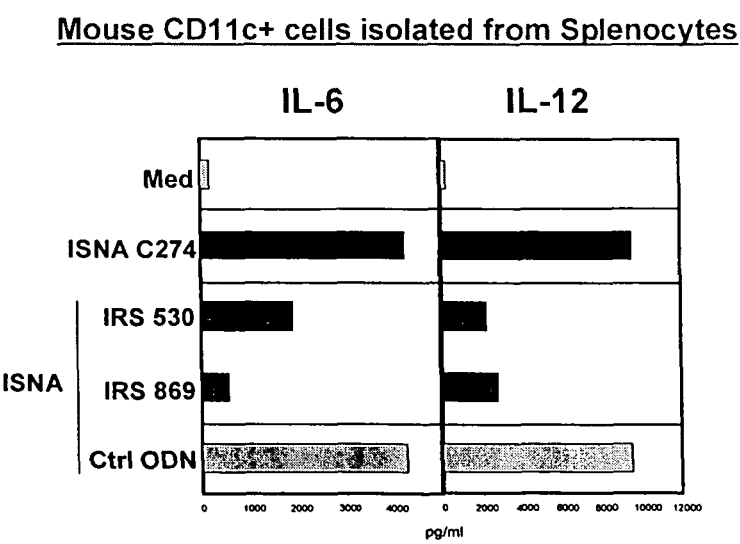

IRPs inhibited IL-6 and IL-12 secretion from ISNA-stimulated murine splenocytes and CD11c+ cells. Examples of results from such assays with murine cells are presented in FIGS. 1A-1B. FIG. 1A depicts results of splenocytes stimulated with ISNA SEQ ID NO:119 (1018) alone and with ISNA SEQ ID NO:119 (1018) together with varying amounts of two different IRPs, SEQ ID NO:91 (530) and SEQ ID NO:17 (C869), and the control sequence SEQ ID NO: 90 (C532). FIG. 1B depicts results of CD11c+ cells stimulated with ISNA SEQ ID NO:99 5'-TCG TCG AAC GTT CGA GAT GAT-3' (C274) alone and with ISNA SEQ ID NO:99 (C274) together with two different IRPs, (SEQ ID NO:91 (530) and SEQ ID NO:17 (C869), and the control sequence SEQ ID NO: 90 (C532). As indicated in FIGS. 1A and 1B, the presence of either IRP resulted in a reduction in the amount of IL-6 and IL-12 produced by the cells in response to the ISNA. The inhibition of cytokine production by the IRP was responsive to the dose of IRP.

For human cell assays, peripheral blood was collected from volunteers by venipuncture using heparinized syringes. Blood was layered onto a FICOLL® (Amersham Pharmacia Biotech) cushion and centrifuged. PBMCs, located at the FICOLL® interface, were collected, then washed twice with cold phosphate buffered saline (PBS). The cells were resuspended and cultured in 48 or 96 well plates at $2 \times 10^6$ cells/mL in RPMI 1640 with 10% heat-inactivated human AB serum plus 50 units/mL penicillin, 50 µg/mL streptomycin, 300 µg/mL glutamine, 1 mM sodium pyruvate, and 1×MEM nonessential amino acids (NEAA).

Human B cells and human PDCs were isolated using procedures described in Marshall et al. (2003) *J. Leukoc Biol.* 73:781-92. Human B cells were dispensed, incubated, and medium was harvested from each well and tested for IL-6 cytokine concentrations by ELISA as described in Marshall et al. (2003). IRPs SEQ ID NO:91 (530) and SEQ ID NO:17 (869) were tested at various concentrations including 2.8 µM, 0.7 µM and 0.175 µM or ratios of IRP:ISNA of 4:1, 1:1, and 1:4. Control samples included ISNA SEQ ID NO:119 (1018), IRP alone SEQ ID NO:91 (530) and SEQ ID NO:17 (869), media alone and a control oligonucleotide SEQ ID NO: 90 (C532) which contains neither ISNA nor IRS.

Figure 2:
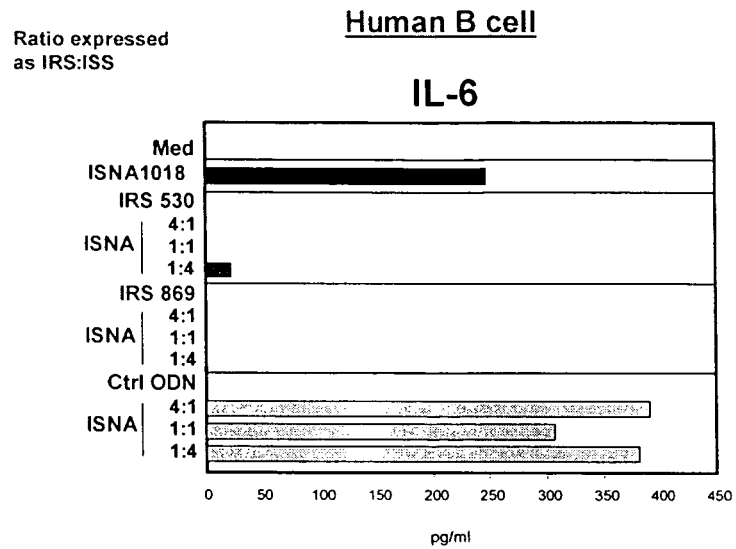
FIG. 2 is a graph showing IL-6 production from human B cells stimulated with ISNA SEQ ID NO:119 (1018) alone and together with IRP SEQ ID NO:91 (530), IRP SEQ ID NO:17 (C869) or control oligonucleotide C532.

As shown in FIG. 2, the presence of either of the IRPs resulted in a reduction of the amount of IL-6 produced by the ISNA-stimulated purified human B cells.

Figure 3:
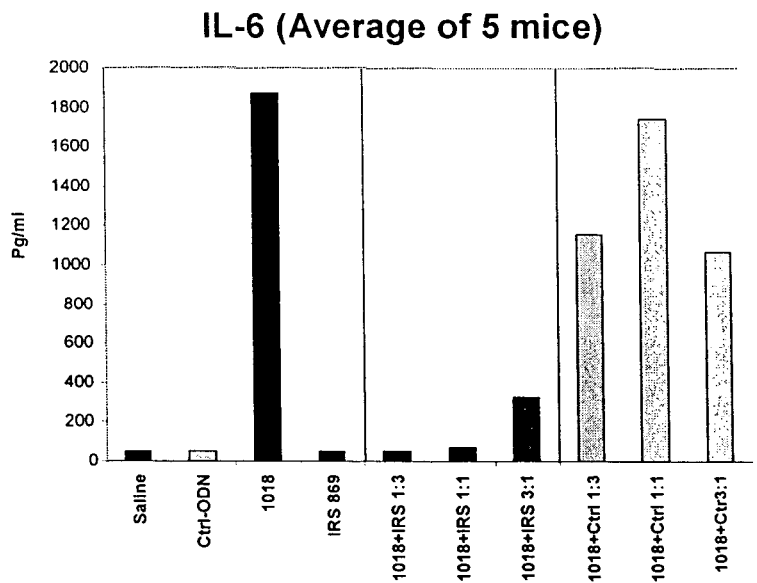
FIG. 3 is a graph showing IL-6 levels in serum from mice injected with ISNA SEQ ID NO:119 (1018) alone and together with IRP SEQ ID NO: 17 (C869) or control oligonucleotide, and IRP SEQ ID NO:17 (C869) alone. The ratio of IRP:ISNA or IRP:control oligonucleotide co-administered varied from 3:1 to 1:3.
Figure 4:
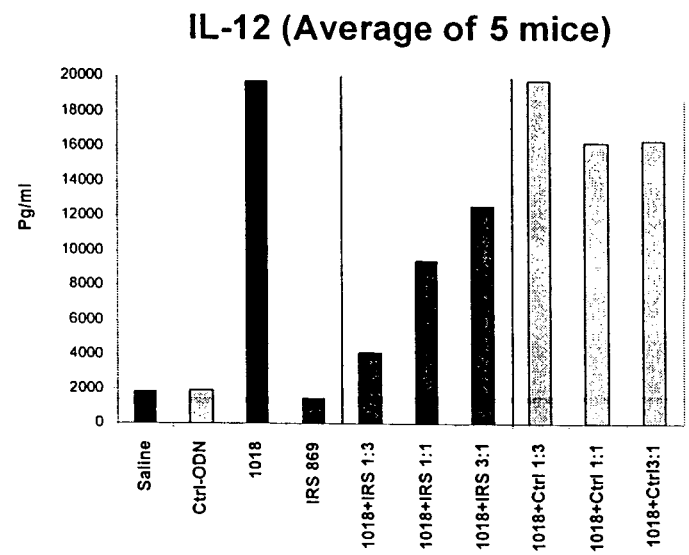
FIG. 4 is a graph showing IL-12 levels in serum from mice injected with ISNA SEQ ID NO:119 (1018) alone and together with IRP SEQ ID NO:17 (C869) or control oligonucleotide, and IRP SEQ ID NO:17 (C869) alone. The ratio of IRP:ISNA or IRP:control oligonucleotide co-administered varied from 3:1 to 1:3.
Figure 5:
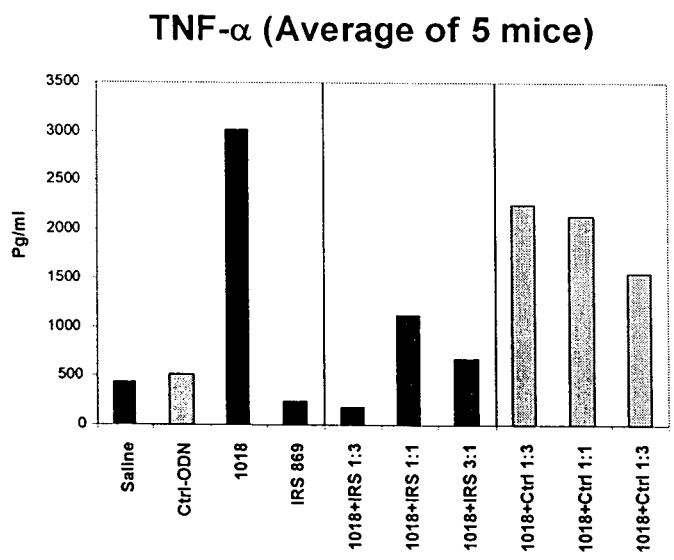
FIG. 5 is a graph showing TNF-α levels in serum from mice injected with ISNA SEQ ID NO:119 (1018) alone and together with IRP SEQ ID NO:17 (C869) or control oligonucleotide, and IRP SEQ ID NO:17 (C869) alone. The ratio of IRP:ISNA or IRP:control oligonucleotide co-administered varied from 3:1 to 1:3.

In vivo activity of IRPs was examined in mice. A group of mice (five animals per group) were each injected subcutaneously with 25 µg ISNA SEQ ID NO:119 (1018) alone or in combination with 75 µg, 25 µg or 8.5 µg control oligonucleotide or IRP SEQ ID NO:17 (C869). Ratios of IRP:ISNA of 3:1, 1:1, and 1:3 were co-administered to the animals. Other control groups were injected with saline, control oligonucleotide alone or IRP SEQ ID NO:17 (C869) alone. Serum was collected 2 hours after injection of the nucleic acids and the level of IL-6, IL-12 and TNF-α in the serum was determined using immunoassay as described earlier for IL-6 and IL-12, and using the mouse anti-TNF-α Quantikine (R&D System, Inc., Minneapolis, Minn.). Results of these assays are depicted in FIGS. 3-5. Administration of the IRP along with the ISNA resulted in a decreased amount of each of the cytokines in the sera relative to the amount of the cytokines in the sera in animals that received the ISNA alone.

As shown in FIG. 3, administration of the IRP with the ISNA at any of the ratios tested resulted in at least approximately a 6-fold reduction in the serum level of IL-6 compared to administration of the ISNA alone. FIG. 4 demonstrates that the inhibition of IL-12 production by the IRP was dose dependent, with all ratios of IRP:ISNA tested resulting in a reduction of the cytokine relative to administration of the ISNA alone. FIG. 5 demonstrates that all ratios of IRP:ISNA tested resulted in a reduction of TNF-α relative to administration of the ISNA alone.

In vivo activity of IRP was also examined when the IRP and ISNA were administered to animal at separate sites on the animal. In this experiment, cytokine responses were compared in groups of mice (five animals per group) that were injected subcutaneously with 25 μg ISNA SEQ ID NO:119 (1018) alone or in combination with 25 μg IRP SEQ ID NO:17 (C869). While the ISNA was injected subcutaneously in all animals, the IRP was injected subcutaneously in the same flank as the ISNA (SC1), subcutaneously in the opposite flank as the ISNA (SC2), intraperitoneally (IP), intravenously (IV), intramuscularly (IM) or intranasally (IN). Control groups were injected with saline, IRP SEQ ID NO:17 (C869) alone or control oligonucleotide with ISNA SEQ ID NO:119 (1018) subcutaneaously in the same flank.

Figure 6:
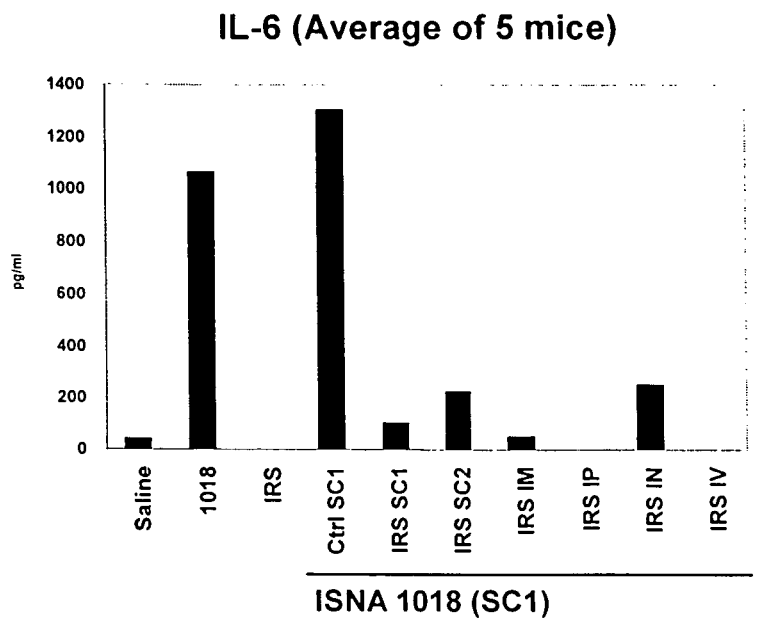
FIG. 6 is a graph showing IL-6 levels in serum from mice injected with ISNA SEQ ID NO:119 (1018) subcutaneously at one site and control oligonucleotide or IRP SEQ ID NO:17 (C869) administered at the same site or at different sites.
Figure 7:
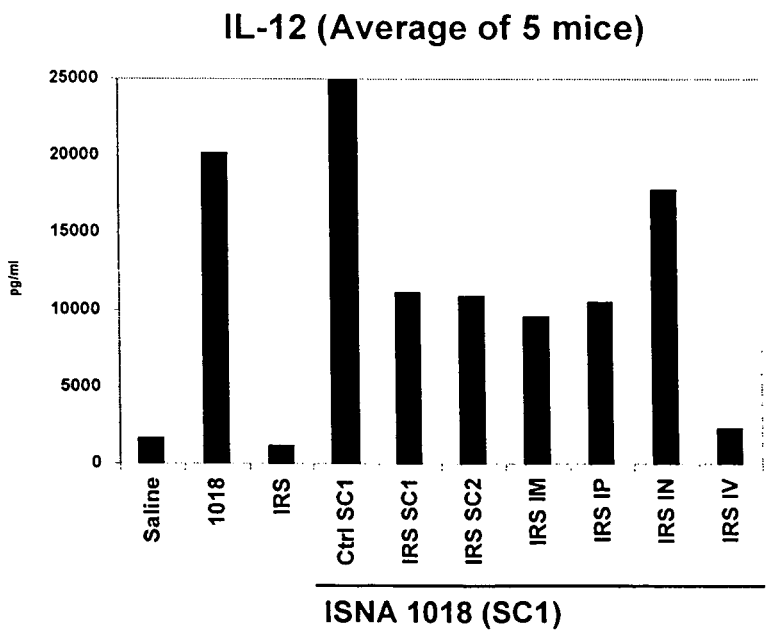
FIG. 7 is a graph showing IL-12 levels in serum from mice injected with ISNA SEQ ID NO:119 (1018) subcutaneously at one site and control oligonucleotide or IRP SEQ ID NO:17 (C869) administered at the same site or at different sites.

Serum was collected 2 hours after injection of the nucleic acids and the level of IL-6 and IL-12 in the serum was determined. As shown in FIG. 6, administration of the IRP at all of the sites tested (i.e., SC1, SC2, IP, IV, IM and IN) resulted in a clear suppression of the amount of IL-6 produced in response to the ISNA. As shown in FIG. 7, administration of the IRP at all of the sites tested also resulted in a suppression of the amount of serum IL-12 in response to the ISNA.

Assays performed in vitro and in vivo demonstrate that the IRP and ISNA need not be co-administered at the same time or the same site in order for the IRP to inhibit the stimulatory activity of the ISNA.

Example 2

IRP Activity and TLR-Dependent Cell Response

As demonstrated herein, IRP inhibit activities or responses associated with TLR-9 signaling. Experiments were performed to further investigate IRP activity and activities or responses associated with TLR-9 and other TLRs.

Murine splenocytes and human PBMCs and PDCs infected with herpes simplex virus type 1 (HSV-1) respond by producing IFN-α and this response is dependent on TLR-9 signalling. Murine splenocytes and human PBMCs and PDCs infected with influenza virus (strain PR/8) also respond by producing IFN-α, however, this response is dependent on TLR-7/8 signalling and independent of TLR-9. The effect of IRPs on innate immune response cytokine production by infected cells was examined.

Figures 8A, 8B:
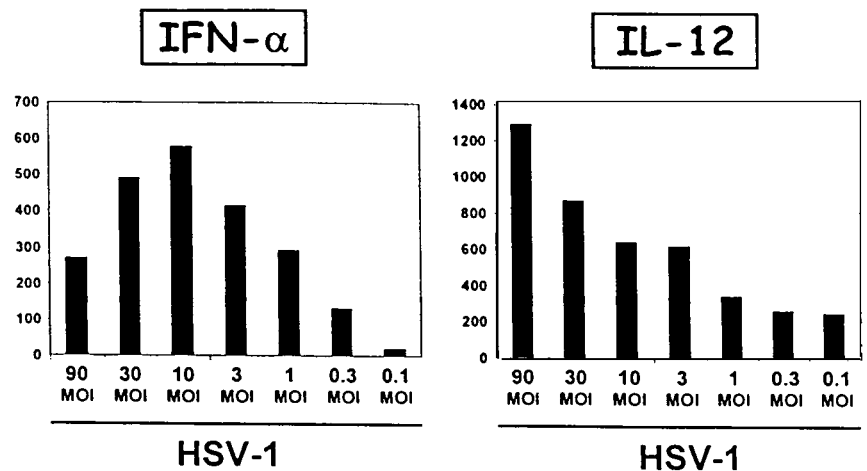
FIGS. 8A-8B depict graphs showing FIG. 8A IFN-α and FIG. 8B IL-12 production by murine CD11c+ splenocytes in response to varying amounts of HSV-1 infection.

Murine CD11+ splenocytes, prepared as described above, were infected with a varying amounts of HSV-1. The amount of IFN-α measured by immunoassay (PBL Biomedical Laboratories, Piscataway, N.J.) and IL-12 produced by the cells was measured and compared to the amount of virus used for infection. FIGS. 8A-8B depict an example of the production of IFN-α and IL-12 in response to the amount of HSV-1 (multiplicity of infection, MOI) used for infection. Cells infected at 10 MOI of HSV-1 clearly produced both IFN-α and IL-12.

Figure 9A:
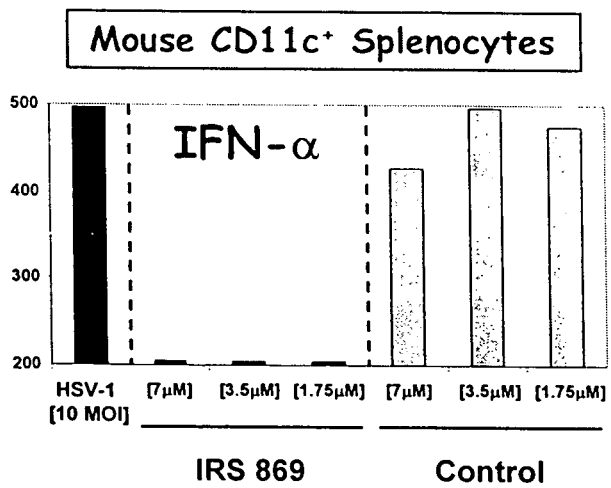
FIGS. 9A-9C depict graphs showing IRP inhibition of cytokine production from HSV-1 stimulated cells.
Figure 9B:
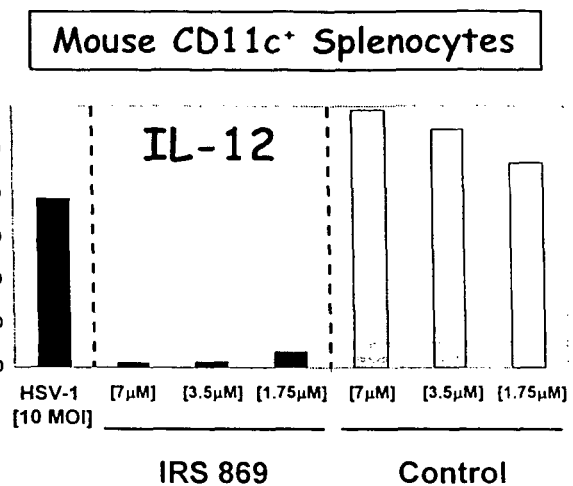
Figure 9C:
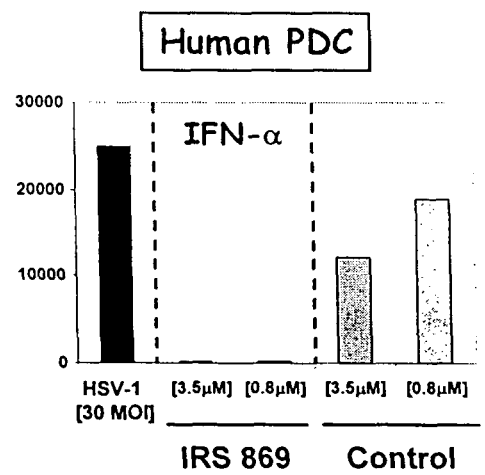

Murine CD11+ splenocytes were then infected with 10 MOI HSV-1 in the presence of varying amounts of IRP SEQ ID NO:17 (C869) (7, 3.5 or 1.75 μM) or control oligonucleotide and the amount of IFN-α and IL-12 produced was determined. As shown in FIGS. 9A and 9B, IRP SEQ ID NO:17 (C869) clearly inhibited production of IFN-α and of IL-12 from the splenocytes at each of the concentrations tested. IRP SEQ ID NO:17 (C869) also inhibited production of IFN-α from HSV-1 infected human PDCs as shown in FIG. 9C. These results are consistent with IRP SEQ ID NO:17 (C869) inhibiting TLR-9 dependent cell responses.

Figure 10A:
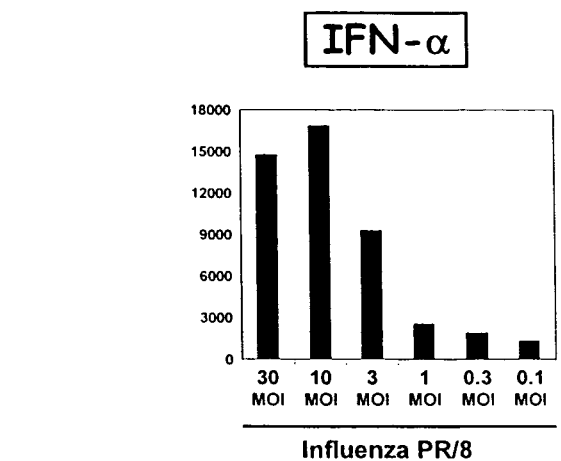
FIGS. 10A-10B depict graphs showing IRP inhibition of cytokine production from influenza virus (PR/8) stimulated cells.

Human PDCs were also infected with a varying amounts of influenza virus (strain PR/8). The amount of IFN-α produced by the cells was measured and compared to the amount of virus used for infection. FIG. 10A depicts an example of the production of IFN-α in response to the amount of influenza virus (multiplicity of infection, MOI) used for infection. Cells infected at 10 MOI of influenza virus (strain PR/8) clearly produced IFN-α in response to the infection.

Figure 10B:
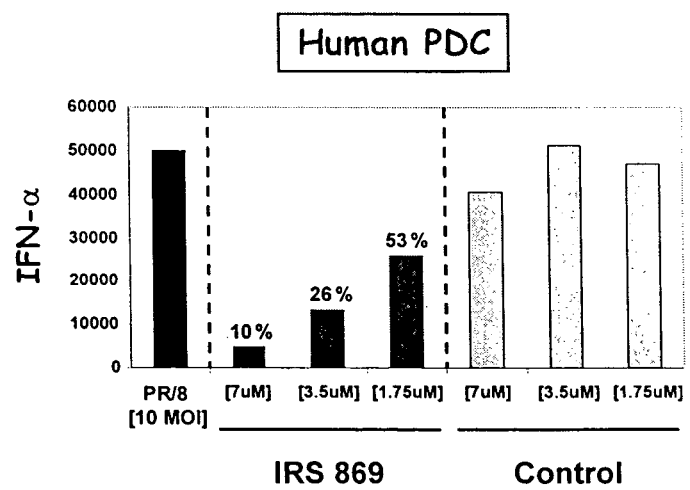

Human PDCs were then infected with 10 MOI influenza virus (strain PR/8) in the presence of varying amounts of IRP SEQ ID NO:17 (C869) (7, 3.5 or 1.75 μM) or control oligonucleotide and the amount of IFN-α produced was determined. As shown in FIG. 10B, IRP SEQ ID NO:17 (C869) clearly inhibited production of IFN-α from the cells in a dose-dependent manner. These results are consistent with IRP SEQ ID NO:17 (C869) also inhibiting TLR-7/8 dependent cell responses.

Figures 11A, 11B:
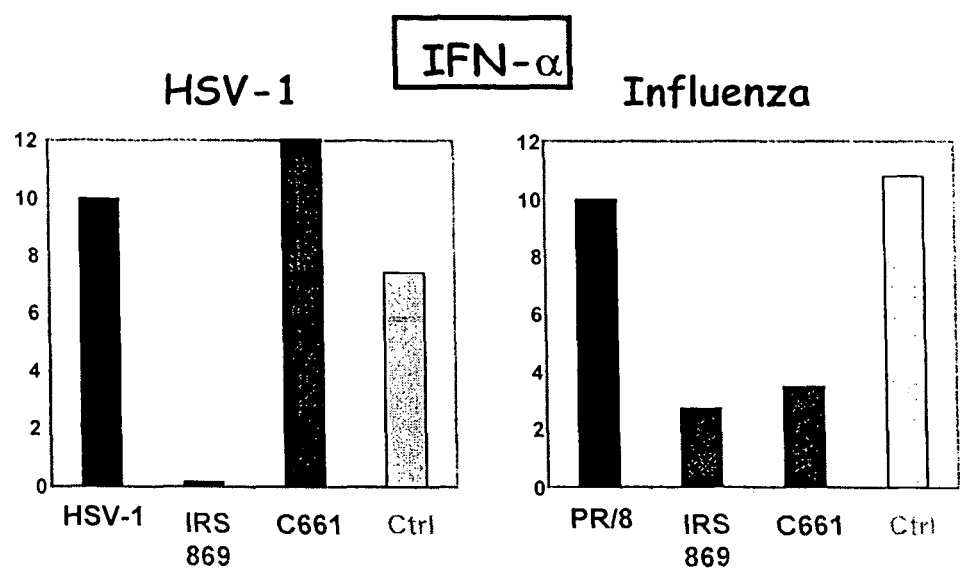
FIGS. 11A-11B depict graphs showing IRP inhibition of IFN-α production from virus stimulated human PDC cells. Shown is IFN-α production by the cells in response to HSV-1 (FIG. 11A, left graph) and influenza virus (FIG. 11B, right graph) in the presence of virus alone, IRP SEQ ID NO:17 (C869), IRP SEQ ID NO:27 (C661) or control oligonucleotide.

SEQ ID NO:27 (C661) was found to differentially inhibit HSV-1 and influenza virus (PR/8) stimulated cells. Human PDCs were infected with HSV-1 at 30 MOI in the presence of SEQ ID NO:17 (C869), SEQ ID NO:27 (C661) or a control oligonucleotide. In some experiments, other concentrations of HSV-1 were used with similar results. PDC were enriched as described in Duramad et al. (2003) *Blood* 102:4487 and incubated with lethally UV-irradiated HSV-1. As shown in FIGS. 11A-11B, SEQ ID NO:27 (C661) showed no inhibitory effect on the production of IFN-α from the cells although IRP SEQ ID NO:17 (C869) completely inhibited IFN-α production. Human PDCs were infected with influenza virus (PR/8) at 10 MOI in the presence of SEQ ID NO:17 (C869), SEQ ID NO:27 (C661) or a control oligonucleotide. As shown in FIGS. 11A-11B, the inhibitory effect of SEQ ID NO:27 (C661) on the production of IFN-α by the cells was comparable to the effect of IRP SEQ ID NO:17 (C869). Accordingly, different IRP species can have different inhibitory effects on cells. For example, IRP SEQ ID NO:27 (C661) inhibits TLR-7/8 dependent cell responses but not TLR-9 cell responses.

Figures 12A, 12B:
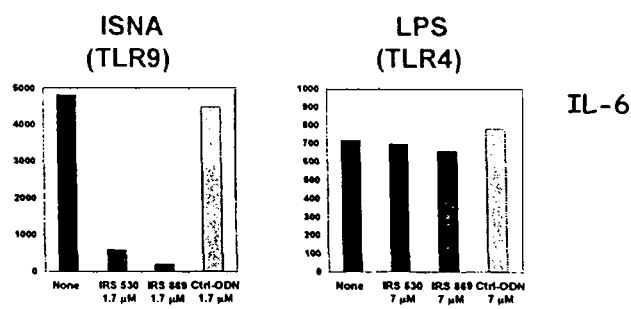
FIGS. 12A-12B depict graphs showing the effect of IRP on IL-6 production from splenocytes stimulated with either FIG. 12A ISNA or FIG. 12B LPS, a TLR4 stimulator. The stimulated cells were incubated with ISNA or LPS alone and together with IRP SEQ ID NO:91 (530), IRP SEQ ID NO:17 (C869) or control oligonucleotide.
Figure 15A:
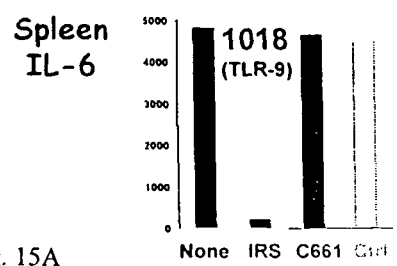
FIGS. 15A-15D depicts graphs showing the effect of IRPs on IL-6 production from splenocytes stimulated with TLR stimulators FIG. 15A, ISNA (SEQ ID NO:119 (1018)), FIG. 15B, LPS, FIG. 15C, loxoribine and FIG. 15D, R848. The stimulated cells were incubated with the indicated TLR stimulator alone and together with of IRP SEQ ID NO:17 (C869), IRP SEQ ID NO:27 (C661) or control oligonucleotide.
Figure 15B:
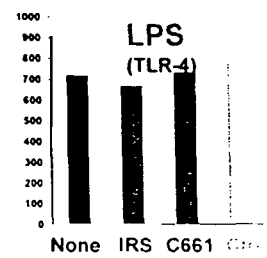
Figure 15C:
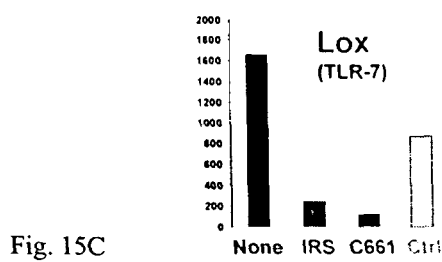
Figure 15D:
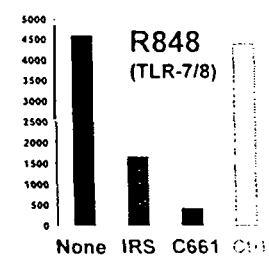

Murine splenocytes produce IL-6 in response to LPS through TLR-4 stimulation. IRPs SEQ ID NO:17 (C869) and SEQ ID NO:91 (530) and a control oligonucleotide were tested for their effect on IL-6 production by LPS stimulation spleen cells. As depicted in FIGS. 12A-12B, neither IRP inhibited IL-6 production from LPS-stimulated spleen cells. By contrast, a four-fold lower concentration of either IRP inhibited IL-6 production from ISNA-stimulated spleen cells. Accordingly, neither IRP SEQ ID NO:17 (C869) or IRP SEQ ID NO: 91 (530) inhibit this TLR-4 dependent cell response.

The effect of IRP SEQ ID NO:17 (C869) on TLR-7/8 dependent responses was further examined with the use of two TLR activators. Loxoribine (7-allyl-7,8-dihydro-8-oxoguanosine) acts as a synthetic adjuvant in anti-tumor responses and has been shown to activate cells of the innate immune system selectively through the TLR-7 dependent signaling pathway (Heil et al. (2003) *Eur. J. Immunol.* 33:2987-2997). Murine spleen cells were stimulated with loxoribine (100 μM) in the presence of varying concentrations of IRP SEQ ID NO:17 (C869) or a control oligonucleotide, and the amount of IL-6 and IL-12 produced was determined. As shown in FIGS. 13A-13D, IRP SEQ ID NO:17 (C869) inhibited TLR-7 induced production of IL-6 from the cells in a dose-dependent manner but did not effect IL-12 production by the cells.

Resiquimod (R-848) is a stimulus for TLR-7 and TLR-8 signaling. Murine spleen cells were stimulated with R-848 (1

μM) in the presence of varying concentrations of IRP SEQ ID NO:17 (C869) or a control oligonucleotide, and the amount of IL-6 and IL-12 produced was determined. As shown in FIGS. 14A-14D, IRP SEQ ID NO:17 (C869) inhibited TLR-7/8 induced production of IL-6 from the cells in a dose-dependent manner but did not effect IL-12 production by the cells.

When tested for inhibition of various TLR stimulation, SEQ ID NO:27 (C661) again was found to inhibit TLR-7/8 dependent cell responses but not TLR-4-dependent or TLR-9 dependent cell responses. As depicted in FIGS. 15A-15D, IRP SEQ ID NO:27 (C661) inhibited IL-6 production from 100 μM loxoribine stimulated spleen cells and from 1 μM R848 stimulated spleen cells. This demonstrates that SEQ ID NO:27 (C661) is effective in inhibiting TLR-7/8 dependent cell responses. However, FIGS. 15A-15D also show that SEQ ID NO:27 (C661) does not inhibit IL-6 production from ISNA stimulated spleen cells or from LPS stimulated spleen cells. Thus, SEQ ID NO:27 (C661) is not effective in inhibiting TLR-9 or TLR-4 dependent cell responses.

IRP SEQ ID NO:17 (C869) inhibits both TLR-7/8 and TLR-9 dependent cytokine production in response to ISNA stimulation, viral infection, and chemical stimulation. IRP SEQ ID NO:27 (C661) inhibits both TLR-7/8 but not TLR-9 dependent cytokine production in response to viral infection, chemical stimulation and ISNA stimulation. Neither IRP SEQ ID NO:17 (C869), IRP SEQ ID NO:91 (530) nor IRP SEQ ID NO:27 (C661) inhibit TLR-4 dependent IL-6 production.

Example 3

TLR-Dependent Activities of IRS-Containing Polynucleotides

In a series of experiments, mouse splenocytes were stimulated with either R848 (TLR-7/8 signalling) or ISNA SEQ ID NO:119 (1018) (TLR-9 signalling) together with various IRP or control oligonucleotides. Table 1 contains results from 2 experiments. The value given is the percentage of the IL-6 response in the presence of the IRP or control oligonucleotide as compared to the IL-6 response with R848 alone.

TABLE 1

IL-6 production from splenocytes stimulated with R848 and IRP.

| Oligonucleotide | μM | % R848 (IL-6) Exp #1 | Exp #2 | Ave. |
|---|---|---|---|---|
| No oligonucleotide | — | 100 | 100 | 100 |
| 5'-TGCTTG CAAGCTTGCAAGCA-3' SEQ ID NO: 27 (C661) | 2.8 0.7 | 24 49 | 27 53 | 26 51 |
| 5'-TGCAAGCTTGCAAGCTTGCAAGCTT-3' SEQ ID NO: 38 (C793) | 2.8 0.7 | 23 48 | 27 58 | 25 53 |
| 5'-TGCTGCAAGCTTGCAGATGAT-3' SEQ ID NO: 39 (C794) | 2.8 0.7 | 24 43 | 26 51 | 25 47 |
| 5'-TGCAAGCTTGCAAGCTTGCAAT-3' SEQ ID NO: 41 (C923) | 2.8 0.7 | 29 54 | 31 69 | 30 61 |
| 5'-TGCTTGCAAGCTTGCAAGC-3' SEQ ID NO: 40 (C919) | 2.8 0.7 | 22 41 | 25 43 | 23 42 |
| 5'-TGCTTGCAAGCTTGCAAG-3' SEQ ID NO: 28 (C921) | 2.8 0.7 | 18 36 | 18 36 | 18 36 |

TABLE 1-continued

IL-6 production from splenocytes stimulated with R848 and IRP.

| Oligonucleotide | μM | % R848 (IL-6) Exp #1 | Exp #2 | Ave. |
|---|---|---|---|---|
| 5'-TGCTTGCAAGCTTGCA-3' SEQ ID NO: 29 (C922) | 2.8 0.7 | 20 36 | 22 37 | 21 36 |
| 5'-TGCTTGCAAGCTTG-3' SEQ ID NO: 42 (C930) | 2.8 0.7 | 48 60 | 42 63 | 45 62 |
| 5'-TGCTTGCAAGC-3' SEQ ID NO: 72 (C931) | 2.8 0.7 | 64 77 | 74 90 | 69 84 |
| 5'-GCTTGCAAGCTTGCAAGCA-3' SEQ ID NO: 30 (C935) | 2.8 0.7 | 31 57 | 32 70 | 32 63 |
| 5'-CTTGCAAGCTTGCAAGCA-3' SEQ ID NO: 31 (C936) | 2.8 0.7 | 39 65 | 41 71 | 40 68 |
| 5'-TTGCAAGCTTGCAAGCA-3' SEQ ID NO: 32 (C937) | 2.8 0.7 | 25 49 | 26 54 | 26 52 |
| 5'-AGCTTGCAAGCTTGCAAGCA-3' SEQ ID NO: 43 (C938) | 2.8 0.7 | 28 56 | 27 54 | 27 55 |
| 5'-TACTTGCAAGCTTGCAAGCA-3' SEQ ID NO: 44 (C939) | 2.8 0.7 | 23 39 | 22 46 | 22 43 |
| 5'-TGATTGCAAGCTTGCAAGCA-3' SEQ ID NO: 45 (C940) | 2.8 0.7 | 29 43 | 25 46 | 27 44 |
| 5'-AAATTGCAAGCTTGCAAGCA-3' SEQ ID NO: 46 (C941) | 2.8 0.7 | 21 47 | 24 48 | 23 48 |
| 5'-CTTGCAAGCTTGCAAG-3' SEQ ID NO: 73 (C909) | 2.8 0.7 | 61 84 | 70 91 | 66 88 |
| 5'-TGCAAGCTTGCA-3' SEQ ID NO: 74 (C910) | 2.8 0.7 | 62 73 | 62 80 | 62 77 |
| 5'-TGCTTGCAAGCTAGCAAGCA-3' SEQ ID NO: 33 (C917) | 2.8 0.7 | 25 43 | 30 59 | 27 51 |
| 5'-TGCTTGCAAGCTTGCTAGCA-3' SEQ ID NO: 34 (C918) | 2.8 0.7 | 17 34 | 18 40 | 17 37 |
| 5'-TGCTTGACAGCTTGACAGCA-3' SEQ ID NO: 35 (C932) | 2.8 0.7 | 16 35 | 19 43 | 18 39 |
| 5'-TGCTTAGCAGCTATGCAGCA-3' SEQ ID NO: 36 (C933) | 2.8 0.7 | 18 34 | 20 41 | 19 38 |
| 5'-TGCAAGCAAGCTAGCAAGCA-3' SEQ ID NO: 37 (C934) | 2.8 0.7 | 22 36 | 24 52 | 23 44 |
| 5'-TCCTGGAGGGGTTGT-3' SEQ ID NO: 17 (C869) | 2.8 0.7 | 78 82 | 94 119 | 86 100 |
| 5'-TGCTGGAGGGGTTGT-3' SEQ ID NO: 47 (C945) | 2.8 0.7 | 20 37 | 24 49 | 22 43 |

Table 2 contains results from ISNA SEQ ID NO:119 (1018) (TLR-9 signalling) stimulated cells. The value given is the percentage of the IL-6 or IL-12 response in the presence of the IRP or control oligonucleotide as compared to the IL-6 or IL-12 response with the ISNA alone.

TABLE 2

IL-6 and IL-12 production from splenocytes stimulated with ISNA and IRP.

| Oligonucleotide | μM | IL-6 | % ISNA | IL-12 | % ISNA |
|---|---|---|---|---|---|
| ISNA SEQ ID NO:_1018 | 0.7 | 12875 | 100 | 3489 | 100 |
| ISNA + SEQ ID NO:_C869 | 0.7 | 1234 | 10 | 1228 | 35 |
| ISNA + SEQ ID NO:_C945 | 0.7 | 5664 | 44 | 1605 | 46 |
| ISNA + SEQ ID NO:_C661 | 0.7 | 11376 | 88 | 2591 | 74 |

Table 3 contains results from 3 experiments. The value given is the percentage of the IL-6 response in the presence of the IRP or control oligonucleotide as compared to the IL-6 response with R848 alone (TLR-7/8 signalling).

TABLE 3

IL-6 production from splenocytes stimulated with R848 and IRP.

| Oligonucleotide | μM | % R848 (IL-6) Exp 1 | Exp 2 | Exp 3 | Ave. |
|---|---|---|---|---|---|
| No oligonucleotide | — | 100 | 100 | 100 | 100 |
| 5'-TGCTCCTGGAGGTTAAGT-3' SEQ ID NO: 90 (C532) | 2.8 | 96 | 2 | 88 | 92 |
| | 0.7 | 98 | 79 | 95 | 91 |
| 5'-TGCTTGCAAGCTTGCAAGCA-3' SEQ ID NO: 27 (C661) | 2.8 | 14 | 7 | 23 | 15 |
| | 0.7 | 27 | 18 | 70 | 38 |
| 5'-TCCTGGAGGGGTTGT-3' SEQ ID NO: 17 (C869) | 2.8 | 47 | 94 | 117 | 86 |
| | 0.7 | 50 | 76 | 106 | 78 |
| 5'-TGCTGGAGGGGTTGT-3' SEQ ID NO: 47 (C945) | 2.8 | 18 | 20 | 24 | 21 |
| | 0.7 | 30 | 38 | 47 | 38 |
| 5'-TACTGGAGGGGTTGT-3' SEQ ID NO: 76 (C946) | 2.8 | 33 | 28 | 43 | 35 |
| | 0.7 | 50 | 48 | 73 | 57 |
| 5'-TTCTGGAGGGGTTGT-3' SEQ ID NO: 77 (C947) | 2.8 | 56 | 131 | 82 | 90 |
| | 0.7 | 77 | 79 | 101 | 86 |
| 5'-TGCTGCTGGAGZ'GGTTGT-3' SEQ ID NO: 78 (C949) (Z' = 7-deaza-dG) | 2.8 | 26 | 21 | 26 | 24 |
| | 0.7 | 46 | 46 | 54 | 49 |
| 5'-TGCTGGAGZ'GGTTGT-3' SEQ ID NO: 79 (C950) (Z' = 7-deaza-dG) | 2.8 | 27 | 26 | 36 | 29 |
| | 0.7 | 41 | 42 | 50 | 44 |

Tables 4 and 5 contains results from ISNA SEQ ID NO:119 (1018) (TLR-9 signalling) stimulated cells. The value given is the percentage of the IL-6 (Table 4) or IL-12 (Table 5) response in the presence of the IRP or control oligonucleotide as compared to the IL-6 or IL-12 response with the ISNA alone.

TABLE 4

IL-6 production from splenocytes stimulated with ISNA and IRP.

| Oligonucleotide | μM | % ISNA (IL-6) Exp #1 | Exp #2 | Ave. |
|---|---|---|---|---|
| No oligonucleotide | — | 100 | 100 | 100 |
| 5'-TGCTGCTGCAGGTTAAGT-3' SEQ ID NO: 90 (C532) | 2.8 | 104 | 93 | 98 |
| | 0.7 | 86 | 184 | 135 |
| 5'-TGCTTGCAAGCTTGCAAGCA-3' SEQ ID NO: 27) (C661) | 2.8 | 61 | 62 | 61 |
| | 0.7 | 142 | 119 | 130 |
| 5'-TCCTGGAGGGGTTGT-3' SEQ ID NO: 17 (C869) | 2.8 | 10 | 8 | 9 |
| | 0.7 | 35 | 25 | 30 |
| 5'-TGCTGGAGGGGTTGT-3' SEQ ID NO: 47 (C945) | 2.8 | 30 | 41 | 35 |
| | 0.7 | 54 | 59 | 56 |
| 5'-TACTGGAGGGGTTGT-3' SEQ ID NO: 76 (C946) | 2.8 | 20 | 20 | 20 |
| | 0.7 | 38 | 56 | 47 |
| 5'-TTCTGGAGGGGTTGT-3' SEQ ID NO: 77 (C947) | 2.8 | 52 | 116 | 84 |
| | 0.7 | 64 | 34 | 49 |
| 5'-TGCTGCTGGAGZ'GGTTGT-3' SEQ ID NO: 78 (C949) (Z' = 7-deaza-dG) | 2.8 | 25 | 18 | 21 |
| | 0.7 | 62 | 93 | 77 |
| 5'-TGC TGG AGZ' GGT TGT-3' SEQ ID NO: 79 (C950) (Z' = 7-deaza-dG) | 2.8 | 86 | 47 | 66 |
| | 0.7 | 118 | 146 | 132 |

TABLE 5

IL-12 production from splenocytes stimulated with ISNA and IRP.

| Oligonucleotide | μM | % ISNA (IL-12) Exp #1 | Exp #2 | Ave. |
|---|---|---|---|---|
| No oligonucleotide | — | 100 | 100 | 100 |
| 5'-TGCTCCTGCAGGTTAAGT-3' SEQ ID NO: 90 (C532) | 2.8 | 101 | 94 | 98 |
| | 0.7 | 74 | 74 | 74 |
| 5'-TGCTTGCAAGCTTGCAAGCA-3' SEQ ID NO: 27 (C661) | 2.8 | 64 | 59 | 61 |
| | 0.7 | 58 | 63 | 61 |
| 5'-TCCTGGAGGGGTTGT-3' SEQ ID NO: 17 (C869) | 2.8 | 19 | 21 | 20 |
| | 0.7 | 35 | 40 | 38 |
| 5'-TGCTGGAGGGGTTGT-3' SEQ ID NO: 47 (C945) | 2.8 | 48 | 35 | 42 |
| | 0.7 | 49 | 44 | 46 |
| 5'-TACTGGAGGGGTTGT-3' SEQ ID NO: 76 (C946) | 2.8 | 30 | 23 | 26 |
| | 0.7 | 42 | 37 | 39 |
| 5'-TTCTGGAGGGGTTGT-3' SEQ ID NO: 77 (C947) | 2.8 | 45 | 44 | 45 |
| | 0.7 | 53 | 42 | 47 |
| 5'-TGCTGCTGGAGZ'GGTTGT-3' SEQ ID NO: 78 (C949) (Z' = 7-deaza-dG) | 2.8 | 39 | 45 | 42 |
| | 0.7 | 53 | 44 | 49 |
| 5'-TGC TGG AGZ' GGT TGT-3' SEQ ID NO: 79 (C950) (Z' = 7-deaza-dG) | 2.8 | 68 | 69 | 68 |
| | 0.7 | 66 | 65 | 65 |

Table 6 lists exemplary IRS and their effectiveness in inhibiting TLR signaling.

TABLE 6

Immunoregulatory DNA Sequences (IRS) sequences

| SEQ ID NO: | | TLR-9 Inhibition | TLR-7/8 Inhibition |
|---|---|---|---|
| SEQ ID NO: 90 (C532) | 5'-TCCTGCAGGTTAAGT-3' (control) | − | − |
| SEQ ID NO: 17 (C869) | 5'-TCCTGGAGGGGTTGT-3' | +++ | +/− |
| SEQ ID NO: 27 (C661) | 5'-TGCTTGCAAGCTTGCAAGCA-3' | − | +++ |
| SEQ ID NO: 67 (C907) | 5'-TGCTTGCAAGCTTGCAAGCA-HEG-TCCTGGAGGGGTTGT-3' | +++ | +++ |
| SEQ ID NO: 47 (C945) | 5'-TGCTGGAGGGGTTGT-3' | ++/− | +++ |
| SEQ ID NO: 80 (1040) | 5'-TGACTGTGAACCTTAGAGATGA-3' (Control) | − | − |
| SEQ ID NO: 81 (C709) | 5'-GCTAGAGCTTAGGCT-3' (Control) | − | − |
| SEQ ID NO: 24 (C533) | 5'-TGACTGTAGGCGGGAAGATGA-3' | ++ | − |
| SEQ ID NO: 82 (C217) | 5'-GCGGCGGGCGGCGCGCGCCC-3' | + | − |
| SEQ ID NO: 83 (C218) | 5'-GCGCGCGCGCGCGCGCGCGC-3' | + | − |
| SEQ ID NO: 84 (C219) | 5'-CCGGCCGGCCGGCCGGCCGG-3' | + | − |
| SEQ ID NO: 25 (C707) | 5'-GAGCAAGCTGGACCTTCCAT-3' | + | − |
| SEQ ID NO: 85 (1019) | 5'-TGACTGTGAAGGTTAGAGATGA-3' | ++ | − |
| SEQ ID NO: 86 (C708) | 5'-CCTCAAGCTTGAGGGG-3' | +++ | + |
| SEQ ID NO: 87 (C888) | 5'-TTAGGGTTAGGGTTAGGGTTAGGG-3' | ++ | ND |
| SEQ ID NO: 88 (C889) | 5'-TTAGGGTTAGGGTTAGGGTTAGGG-3' | − | ND |
| SEQ ID NO: 89 (C890) | 5'-CCTCAAGCTTGAGGGG-3' | − | ND |
| SEQ ID NO: 26 (C891) | 5'-CCTCAAGCTTGAGZ'GG-3' | +++ | ND |
| SEQ ID NO: 91 (530) | 5'-TCCTGGCGGGGAAGT-3' | +++ | + |
| SEQ ID NO: 92 (C823) | 5'-TCCTGGCGZ'GGAAGT-3' | +++ | + |
| SEQ ID NO: 93 (C824) | 5'-TCCTGGCGAGGAAGT-3' | − | ND |
| SEQ ID NO: 94 (C825) | 5'-TCCTGGCGGGAAAGT-3' | + | ND |
| SEQ ID NO: 95 (C826) | 5'-TCCTGGCGGAAAAGT-3' | − | − |
| SEQ ID NO: 10 (C827) | 5'-TCCTAACGGGGAAGT-3' | +++ | ND |

TABLE 6-continued

Immunoregulatory DNA Sequences (IRS) sequences

| SEQ ID NO: | | TLR-9 Inhibition | TLR-7/8 Inhibition |
|---|---|---|---|
| SEQ ID NO: 96 (C531) | 5'-TCCTGGAGGGGAAGT-3' | +++ | + |
| SEQ ID NO: 11 (C828) | 5'-TCCTAAGGGGAAGT-3' | +++ | ND |
| SEQ ID NO: 12 (C841) | 5'-TCCTAACGGGGTTGT-3' | +++ | ND |
| SEQ ID NO: 13 (C842) | 5'-TCCTAACGGGGCTGT-3' | +++ | ND |
| SEQ ID NO: 14 (C843) | 5'-TCCTCAAGGGGCTGT-3' | ++ | ND |
| SEQ ID NO: 15 (C844) | 5'-TCCTCAAGGGGTTGT-3' | ++ | ND |
| SEQ ID NO: 16 (C845) | 5'-TCCTCATGGGGTTGT-3' | ++ | ND |
| SEQ ID NO: 97 (C892) | 5'-TCCTGGCGGGGAAGT-3' | − | ND |
| SEQ ID NO: 17 (C869) | 5'-TCCTGGAGGGGTTGT-3' | +++ | ++/− |
| SEQ ID NO: 18 (C870) | 5'-TCCTGGAGGGGCTGT-3' | +++ | ND |
| SEQ ID NO: 19 (C871) | 5'-TCCTGGAGGGGCCAT-3' | +++ | ND |
| SEQ ID NO: 20 (C872) | 5'-TCCTGGAGGGGTCAT-3' | +++ | ND |
| SEQ ID NO: 21 (C873) | 5'-TCCGGAAGGGGAAGT-3' | ++ | ND |
| SEQ ID NO: 22 (C874) | 5'-TCCGGAAGGGGTTGT-3' | ++ | ND |
| SEQ ID NO: 23 (C920) | 5'-TCCTGGAGZ'GGTTGT-3' | +++ | ++/− |
| SEQ ID NO: 27 (C661) | 5'-TGCTTGCAAGCTTGCAAGCA-3' | − | +++ |
| SEQ ID NO: 38 (C793) | 5'-TGCAAGCTTGCAAGCTTGCAAGCTT-3' | +/− | +++ |
| SEQ ID NO: 39 (C794) | 5'-TGCTGCAAGCTTGCAGATGAT-3' | +/− | +++ |
| SEQ ID NO: 73 (C909) | 5'-CTTGCAAGCTTGCAA G-3' | − | − |
| SEQ ID NO: 74 (C910) | 5'-TGCAAGCTTGCA-3' | − | − |
| SEQ ID NO: 33 (C917) | 5'-TGCTTGCAAGCTAGCAAGCA-3' | − | +++ |
| SEQ ID NO: 34 (C918) | 5'-TGCTTGCAAGCTTGCTAGCA-3' | − | +++ |
| SEQ ID NO: 40 (C919) | 5'-TGCTTGCAAGCTTGCAAGC-3' | − | +++ |
| SEQ ID NO: 28 (C921) | 5'-TGCTTGCAAGCTTGCAAG-3' | − | +++ |
| SEQ ID NO: 29 (C922) | 5'-TGCTTGCAAGCTTGCA-3' | − | +++ |

TABLE 6-continued

Immunoregulatory DNA Sequences (IRS) sequences

| SEQ ID NO: | | TLR-9 Inhibition | TLR-7/8 Inhibition |
|---|---|---|---|
| SEQ ID NO: 41 (C923) | 5'-TGCAAGCTTGCAAGCTTGCAAT-3' | – | +++ |
| SEQ ID NO: 67 (C907) | 5'-TGCTTGCAAGCTTGCAAGCA-HEG-TCCTGGAGGGGTTGT-3' | +++ | +++ |
| SEQ ID NO: 66 (C908) | 5'-TGCTTGCAAGCTTGCAAGCATCCTGGA GGGGTTGT-3' | +++ | +++ |
| SEQ ID NO: 68 (C913) | 5'-TGCTTGCAAGCTAGCAAGCA-HEG-TCCTGGAGGGGTTGT-3' | +++ | +++ |
| SEQ ID NO: 69 (C914) | 5'-TGCTTGCAAGCTTGCTAGCA-HEG-TCCTGGAGGGGTTGT-3' | +++ | +++ |
| SEQ ID NO: 70 (C916) | 5'-TGCTTGCAAGCTTGCTAGCA-HEG-TCCTGGAGZ'GGTTGT-3' | +++ | +++ |

Z' = 7-deaza-dG; +++ – indicates activity range from very active to inactive; ND: not determined.

In a series of dose-response experiments, mouse splenocytes were stimulated with either R848 (TLR-7/8 signalling) or ISNA SEQ ID NO:119 (1018) (TLR-9 signalling) together with various IRP or control oligonucleotides. Table 7 contains results of IL-6 production in the presence at varing ratios of IRP:ISNA. The value given is the percentage of the IL-6 response in the presence of the IRP or control oligonucleotide as compared to the IL-6 response with ISNA alone.

TABLE 7

IL-6 production from splenocytes stimulated with ISNA and IRP.

| | % of ISNA IL-6 ratio of IRP:ISNA | | | | | |
|---|---|---|---|---|---|---|
| | 2:1 | 1:1 | 1:2 | 1:4 | 1:8 | 1:16 |
| ISNA SEQ ID NO: 119 (1018) | 100 | 100 | 100 | 100 | 100 | 100 |
| Culture medium | 1 | 1 | 1 | 1 | 1 | 1 |
| 5'-TCCTGCAGGTTAAGT SEQ ID NO: 90 (C532) | 132 | 104 | 102 | 97 | 88 | 105 |
| 5'-TGCTTGCAAGCTTGCAAGCA SEQ ID NO: 27 (C661) | 58 | 78 | 81 | 84 | 85 | 104 |
| 5'-TCCTGGAGGGGTTGT SEQ ID NO: 17 (C869) | 2 | 7 | 12 | 32 | 53 | 79 |
| 5'-TGCTCCTGGAGGGGTTGT SEQ ID NO: 52 (C954) | 2 | 4 | 7 | 19 | 41 | 80 |
| 5'-TCCTGCTGGAGGGGTTGT SEQ ID NO: 38 (C955) | 14 | 29 | 39 | 55 | 67 | 85 |
| 5'-TGCTTGTCCTGGAGGGGTTGT SEQ ID NO: 53 (C956) | 2 | 2 | 4 | 10 | 25 | 72 |
| 5'-TGCTTGACATCCTGGAGGGGTTGT SEQ ID NO: 54 (C957) | 2 | 2 | 4 | 10 | 26 | 76 |
| 5'-TGCTTGACAGCTTGACAGTCCTGGAG GGGTTGT SEQ ID NO: 55 (C962) | 2 | 2 | 3 | 9 | 31 | 71 |
| 5'-TGCTTGACAGCTTGATCCTGGAGGGG TTGT SEQ ID NO: 56 (C963) | 3 | 2 | 3 | 4 | 22 | 58 |

TABLE 7-continued

IL-6 production from splenocytes stimulated with ISNA and IRP.

| | % of ISNA IL-6 ratio of IRP:ISNA | | | | | |
|---|---|---|---|---|---|---|
| | 2:1 | 1:1 | 1:2 | 1:4 | 1:8 | 1:16 |
| 5'-TGCTTGACAGCTTCCTGGAGGGGTTG T SEQ ID NO: 57 (C964) | 3 | 1 | 2 | 7 | 24 | 55 |
| 5'-TGCTTGACAGCTTGCTCCTGGAGGGG TTGT SEQ ID NO: 58 (C965) | 2 | 1 | 2 | 4 | 24 | 53 |
| 5'-TGCTTGACAGCTTGCTTGTCCTG GAGGGGTTGT SEQ ID NO: 59 (C966) | 2 | 1 | 2 | 7 | 29 | 63 |
| 5'-TGCTTGACAGCTTGACAGCATCCT GGAGGGGTTGT SEQ ID NO: 60 (C967) | 2 | 1 | 2 | 8 | 33 | 62 |
| 5'-TGCTTGACAGCTTGACAGCATCCT GGAGGGGTTGT SEQ ID NO: 61 (C968) | 2 | 1 | 2 | 2 | 12 | 46 |
| 5'-TGCTTGACAGCTTGACAGCATCC TGGAGGGGT SEQ ID NO: 62 (C969) | 2 | 1 | 1 | 2 | 8 | 44 |
| 5'-TGCTTGACAGCTTGACAGCATCCTGG AGGGG SEQ ID NO: 63 (C970) | 2 | 1 | 2 | 3 | 19 | 59 |
| 5'-TGCTTGCAAGCTTGCTCCTGGAGGGG TTGT SEQ ID NO: 64 (C971) | 2 | 2 | 3 | 9 | 31 | 58 |
| 5'-TGCTTGCAAGCTTCCTGGAGGGGTTG T SEQ ID NO: 65 (C972) | 2 | 2 | 3 | 8 | 28 | 56 |

Table 8 contains results of IL-12 production from murine splenocytes in the presence at varing ratios of IRP:ISNA. The value given is the percentage of the IL-12 response in the presence of the IRP or control oligonucleotide as compared to the IL-12 response with ISNA alone.

TABLE 8

IL-12 production from splenocytes stimulated with ISNA and IRP.

| | % of 1018 (IL-12) ratio of IRP:ISNA | | | | | |
|---|---|---|---|---|---|---|
| | 2:1 | 1:1 | 1:2 | 1:4 | 1:8 | 1:16 |
| ISNA SEQ ID NO: 119 (1018) | 100 | 100 | 100 | 100 | 100 | 100 |
| Culture medium | 6 | 6 | 6 | 6 | 6 | 6 |
| 5'-TCCTGCAGGTTAAGT SEQ ID NO: 90 (C532) | 108 | 96 | 84 | 80 | 74 | 93 |
| 5'-TGCTTGCAAGCTTGCAAGCA SEQ ID NO: 27 (C661) | 44 | 61 | 61 | 61 | 61 | 74 |
| 5'-TCCTGGAGGGGTTGT SEQ ID NO: 17 (C869) | 6 | 20 | 22 | 27 | 35 | 60 |
| 5'-TGCTCCTGGAGGGGTTGT SEQ ID NO: 52 (C954) | 7 | 19 | 20 | 24 | 35 | 58 |
| 5'-TCCTGCTGGAGGGGTTGT SEQ ID NO: 98 (C955) | 27 | 43 | 47 | 43 | 50 | 65 |
| 5'-TGCTTGTCCTGGAGGGGTTGT SEQ ID NO: 53 (C956) | 8 | 22 | 26 | 33 | 43 | 59 |
| 5'-TGCTTGACATCCTGGAGGGGTTGT SEQ ID NO: 54 (C957) | 8 | 23 | 30 | 38 | 46 | 60 |
| 5'-TGCTTGACAGCTTGACAGTCCTGGAGGGGTTGT SEQ ID NO: 55 (C962) | 8 | 9 | 17 | 32 | 46 | 71 |
| 5'-TGCTTGACAGCTTGATCCTGGAGGGGTTGT SEQ ID NO: 56 (C963) | 5 | 5 | 8 | 18 | 29 | 53 |
| 5'-TGCTTGACAGCTTCCTGGAGGGGTTGT SEQ ID NO: 57 (C964) | 5 | 10 | 16 | 25 | 33 | 53 |
| 5'-TGCTTGACAGCTTGCTCCTGGAGGGGTTGT SEQ ID NO: 58 (C965) | 5 | 5 | 9 | 18 | 31 | 51 |
| 5'-TGCTTGACAGCTTGCTTGTCCTGGAGGGGTTGT SEQ ID NO: 59 (C966) | 5 | 6 | 10 | 19 | 31 | 54 |
| 5'-TGCTTGACAGCTTGACAGCATCCTGGAGGGGTTGT SEQ ID NO: 60 (C967) | 5 | 5 | 8 | 19 | 33 | 54 |
| 5'-TGCTTGACAGCTTGACAGCATCCTGGAGGGGTTGT SEQ ID NO: 61 (C968) | 5 | 4 | 9 | 11 | 21 | 46 |
| 5'-TGCTTGACAGCTTGACAGCATCCTGGAGGGGT SEQ ID NO: 62 (C969) | 6 | 4 | 6 | 9 | 18 | 45 |
| 5'-TGCTTGACAGCTTGACAGCATCCTGGAGGGG SEQ ID NO: 63 (C970) | 6 | 5 | 9 | 16 | 30 | 52 |
| 5'-TGCTTGCAAGCTTGCTCGTGGAGGGGTTGT SEQ ID NO: 64 (C971) | 6 | 8 | 11 | 21 | 33 | 54 |
| 5'-TGCTTGCAAGCTTCCTGGAGGGGTTGT SEQ ID NO: 65 (C972) | 7 | 11 | 15 | 22 | 35 | 57 |

Table 9 contains results of IL-6 production from murine splenocytes in the presence at varing concentrations of IRP in the presence of R848 (TLR 7/8 signalling). The value given is the percentage of the IL-6 response in the presence of the IRP or control oligonucleotide as compared to the IL-6 response with R848 alone.

TABLE 9

IL-6 production from splenocytes stimulated with R848 and IRP.

| | % of R848 (IL-6) Conc. of IRP | | | | |
|---|---|---|---|---|---|
| | 5.6 μM | 2.8 μM | 1.4 μM | 0.7 μM | .35 μM |
| R848 | 100 | 100 | 100 | 100 | 100 |
| Culture medium | 0 | 0 | 0 | 0 | 0 |
| 5'-TCCTGCAGGTTAAGT SEQ ID NO: 90 (C532) | 108 | 104 | 108 | 108 | 105 |
| 5'-TGCTTGCAAGCTTGCAAGCA SEQ ID NO: 27 (C661) | 21 | 31 | 47 | 59 | 77 |
| 5'-TCCTGGAGGGGTTGT SEQ ID NO: 17 (C869) | 93 | 106 | 110 | 109 | 104 |
| 5'-TGCTCCTGGAGGGGTTGT SEQ ID NO: 52 (C954) | 23 | 31 | 44 | 56 | 72 |
| 5'-TCCTGCTGGAGGGGTTGT SEQ ID NO: 98 (C955) | 73 | 87 | 107 | 101 | 108 |
| 5'-TGCTTGTCCTGGAGGGGTTGT SEQ ID NO: 53 (C956) | 20 | 28 | 45 | 66 | 75 |
| 5'-TGCTTGACATCCTGGAGGGGTTGT SEQ ID NO: 54 (C957) | 17 | 27 | 39 | 63 | 78 |
| 5'-TGCTTGACAGCTTGACAGTCCTGGAGGGGT SEQ ID NO: 55 (C962) | 17 | 36 | 51 | 75 | 83 |
| 5'-TGCTTGACAGCTTGATCCTGGAGGGGTTGT SEQ ID NO: 56 (C963) | 26 | 35 | 54 | 77 | 93 |
| 5'-TGCTTGACAGCTTCCTGGAGGGGTTGT SEQ ID NO: 57 (C964) | 15 | 30 | 45 | 68 | 89 |
| 5'-TGCTTGACAGCTTGCTCCTGGAGGGGTTGT SEQ ID NO: 58 (C965) | 16 | 31 | 48 | 72 | 82 |
| 5'-TGCTTGACAGCTTGCTTGTCCTGGAGGGGT SEQ ID NO: 59 (C966) | 18 | 40 | 60 | 78 | 92 |
| 5'-TGCTTGACAGCTTGACAGCATCCTGGAGGGGTTGT SEQ ID NO: 60 (C967) | 16 | 41 | 49 | 68 | 80 |
| 5'-TGCTTGACAGCTTGACAGCATCCTGGAGGGGTTGT SEQ ID NO: 61 (C968) | 13 | 29 | 43 | 67 | 83 |
| 5'-TGCTTGACAGCTTGACAGCATCCTGGAGGGGT SEQ ID NO: 62 (C969) | 14 | 26 | 45 | 62 | 80 |
| 5'-TGCTTGACAGCTTGACAGCATCCTGGAGGGG SEQ ID NO: 63 (C970) | 16 | 25 | 45 | 54 | 74 |
| 5'-TGCTTGCAAGCTTGCTCCTGGAGGGGTTGT SEQ ID NO: 64 (C971) | 15 | 29 | 58 | 66 | 67 |
| 5'-TGCTTGCAAGCTTCCTGGAGGGGTTGT SEQ ID NO: 65 (C972) | 17 | 28 | 41 | 54 | 64 |

As shown in Tables 7-9, SEQ ID NO:52 (C954), SEQ ID NO:53 (C956), SEQ ID NO:54 (C957) and SEQ ID NOs:55-

65 (C962-C972) are particularly effective in inhibiting both the TLR-7/8 and TLR-9 dependent cell responses.

Example 4

Figures 16A, 16B:
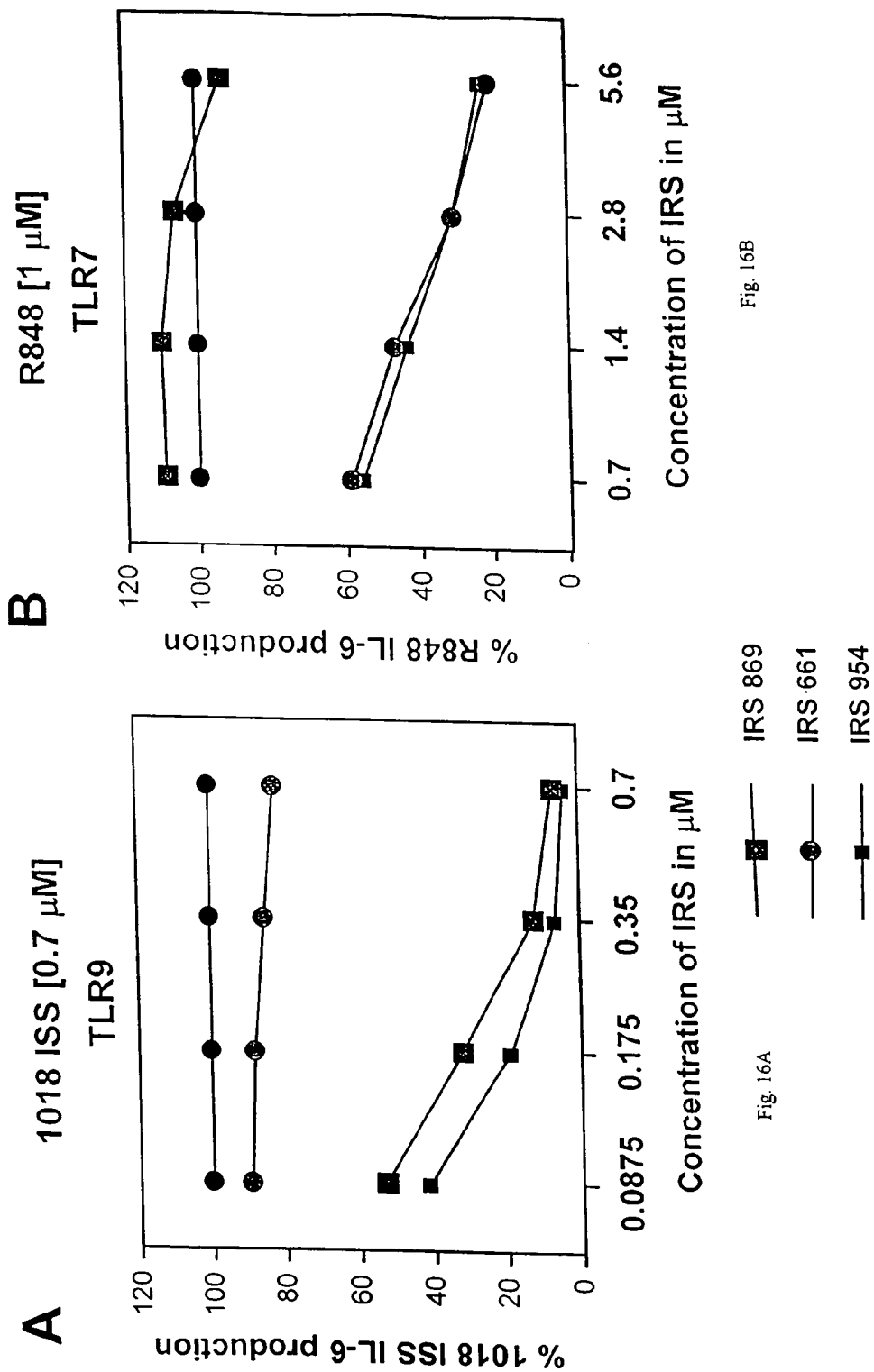
FIGS. 16A-16B depict graphs showing IRP inhibition of IL-6 production from ISNA SEQ ID NO:119 (1018)-stimulated or R848-stimulated cells.

Murine splenic cells were activated with ISNA SEQ ID NO:119 (1018) (0.7 µM) or R848 (1 µM) alone and together with increasing amount of IRP SEQ ID NO:17 (869), IRP SEQ ID NO:27 (661), IRP SEQ ID NO:52 (954). As depicted in FIGS. 16A-16B, IRP SEQ ID NO:17 (869) and IRP SEQ ID NO:52 (954) are potent inhibitor of IL-6 production in response to ISNA SEQ ID NO:119 (1018) while IRP SEQ ID NO:27 (661) and IRP SEQ ID NO:52 (954) are potent inhibitor of R848 activation.

A group of mice were each injected subcutaneously with 2.5 µg of R848 alone or in combination with 450-500 µg or 100-150 µg of control oligonucleotide or IRP SEQ ID NO:52 (954). Serum was collected 1 hours after injection of R848 and the level of IL-12 and TNF-α in the serum was determined using immunoassay as described earlier. Results of these assays are depicted in FIGS. 17A-17B. Administration of the IRP along with R848 resulted in a decreased amount of each of the cytokines in the sera relative to the amount of the cytokines in the sera in animals that received R848 alone.

Figure 18:
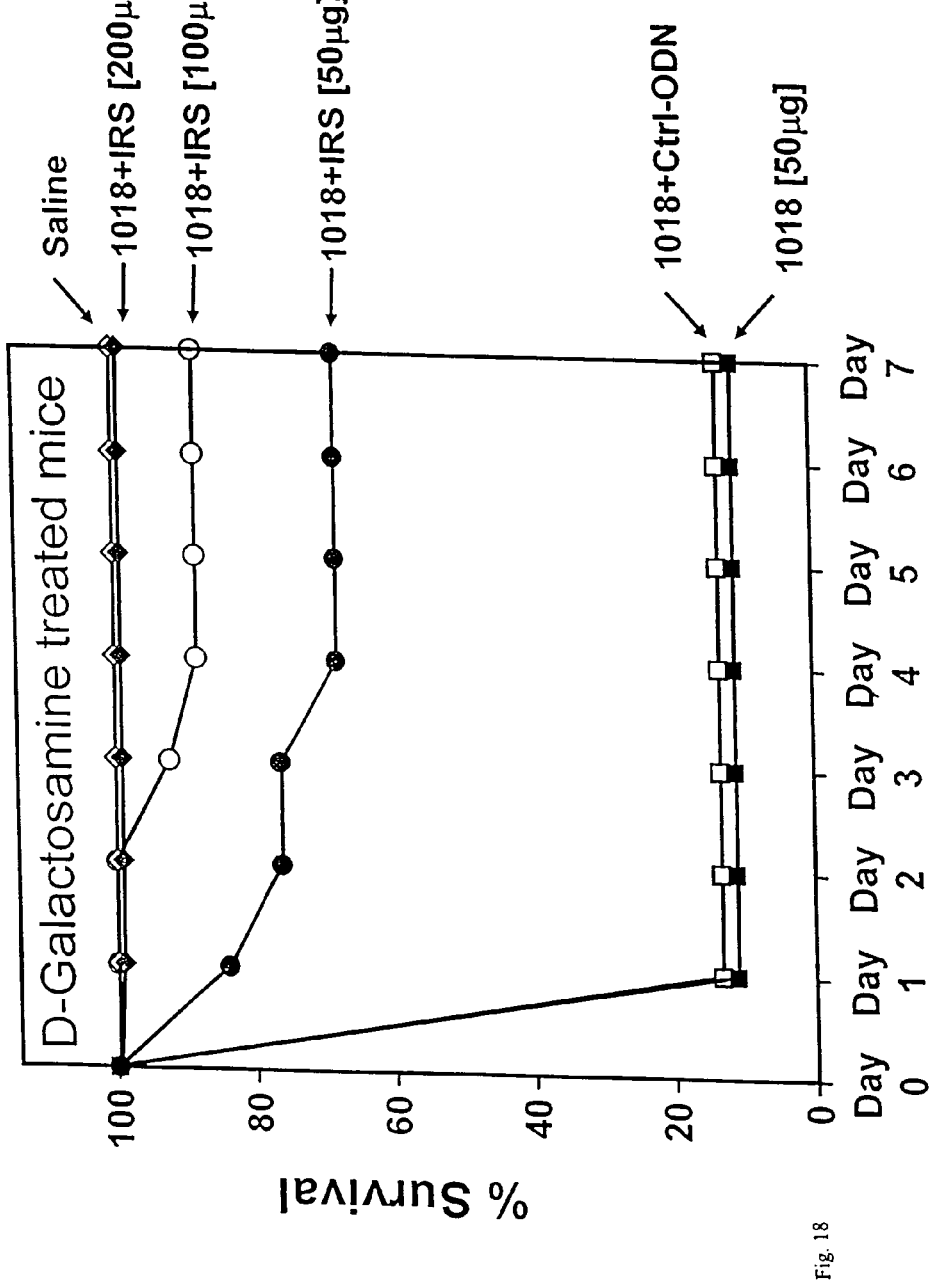
FIG. 18 is a graph showing the percentage of mice alive after treatment with D-galactosamine and ISNA SEQ ID NO:119 (1018) alone and together with IRP SEQ ID NO:52 (954) or IRP SEQ ID NO:17 (869) or control oligonucleotide.

6 to 12 week-old BALB/c mice were injected intraperitoneally with 20 mg of D-galactosamine in saline and subcutaneously with 50 µg of ISNA SEQ ID NO:119 (1018) alone or in combination with 200 µg, 100 µg or 50 µg of IRP SEQ ID NO:52 (954) or IRP SEQ ID NO:17 (869) or of a control oligonucleotide ODN. Mice were then evaluated for survival over a 7 day period. In normal mice, 50 µg of ISNA SEQ ID NO:119 (1018) does not induce death, however, when mice are pre-treated with D-galactosamine, they become highly susceptible to inflammation and die rapidly. As depicted in FIG. 18, IRS could prevent death in a dose dependent manner while inactive control-ODN did not. At the highest dose (200 µg of IRS) 100% of the mice were protected, almost 90% with 100 µg of IRS and still over 60% at a 1:1 ratio. These data thus support a strong in vivo activity of IRS.

Mouse splenocytes were activated with ISNA SEQ ID NO:119 (1018) (FIG. 19A) or R848 (FIG. 19B) alone and together with IRP SEQ ID NO:52 (954) or with the degradation products of IRP SEQ ID NO:52 (954), IRP SEQ ID NO:100 (DV019), IRP SEQ ID NO:101 (DV020), IRP SEQ ID NO:102 (DV021), IRP SEQ ID NO:103 (DV022), IRP SEQ ID NO:104 (DV023) and IRP SEQ ID NO:105 (DV024).

The DV0 sequences are the "IRS 954 N minus sequences" (IRS 954 with N=1 to 6 nucleotides deleted off the 3' end):

```
SEQ ID NO: 100 DV019: 5'-TGC TCC TGG AGG GGT TG

SEQ ID NO: 101 DV020: 5'-TGC TCC TGG AGG GGT T

SEQ ID NO: 102 DV021: 5'-TGC TCC TGG AGG GGT

SEQ ID NO: 103 DV022: 5'-TGC TCC TGG AGG GG

SEQ ID NO: 104 DV023: 5'-TGC ICC TGG AGG G

SEQ ID NO: 105 DV024: 5'-TGC TCC TGG AGG
```

Figure 19:
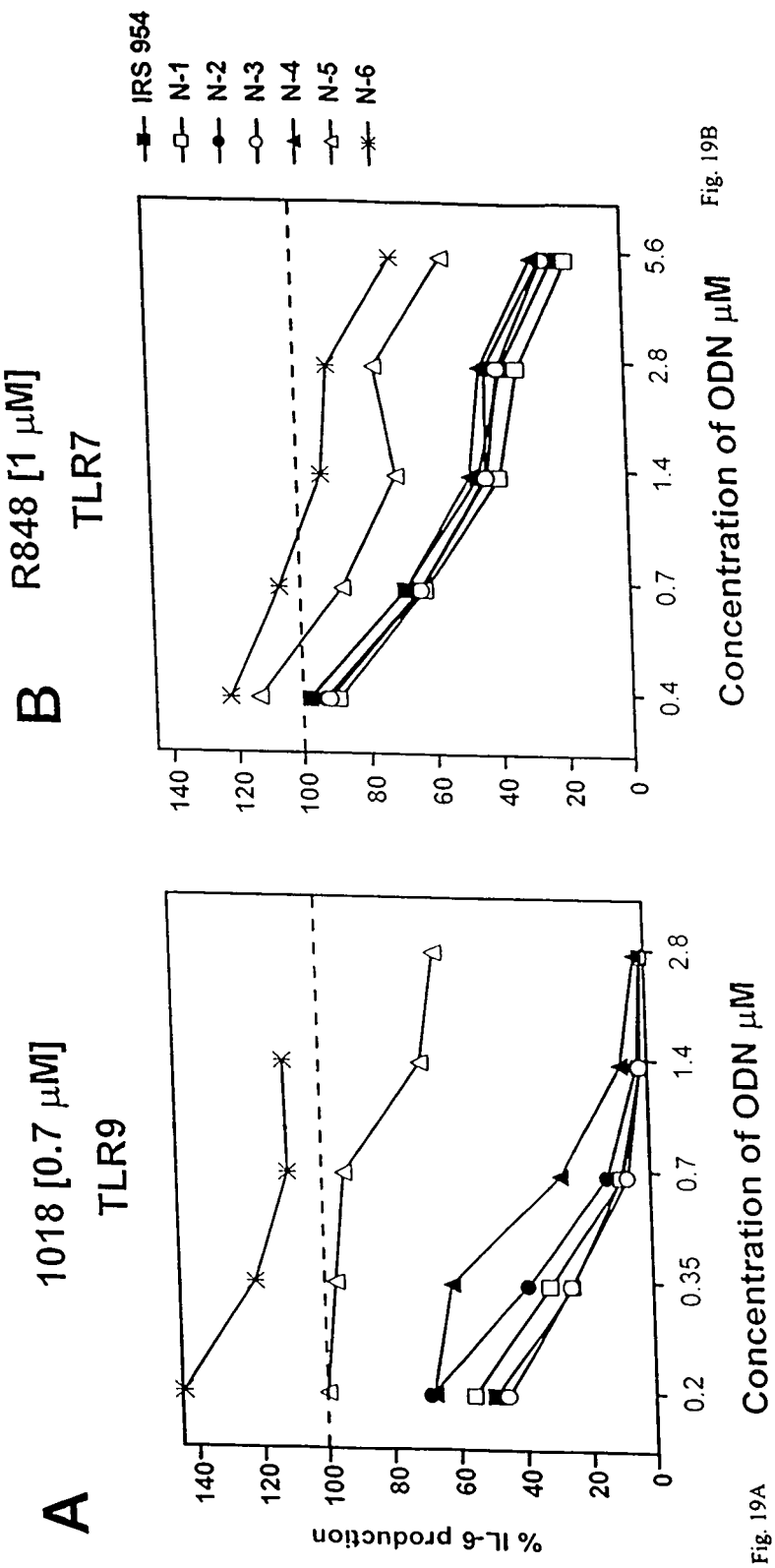
FIGS. 19A-19B depicts graphs showing IRP inhibition of IL-6 production from ISNA SEQ ID NO:119 (1018)-stimulated or R848-stimulated cells.

As depicted in FIGS. 19A and 19B, IL-6 production was decreased when cells were cultured in the presence of IRP SEQ ID NO:52 (954), IRP SEQ ID NO:100 (DV019), IRP SEQ ID NO:101 (DV020), IRP SEQ ID NO:102 (DV021), IRP SEQ ID NO:103 (DV022), IRP SEQ ID NO:104 (DV023) with little to no inhibition with IRP SEQ ID NO:105 (DV024). This suggest that the activity of IRP SEQ ID NO:52 (954) is retained even after degradation of the 3'-end of the sequence.

Figure 20:
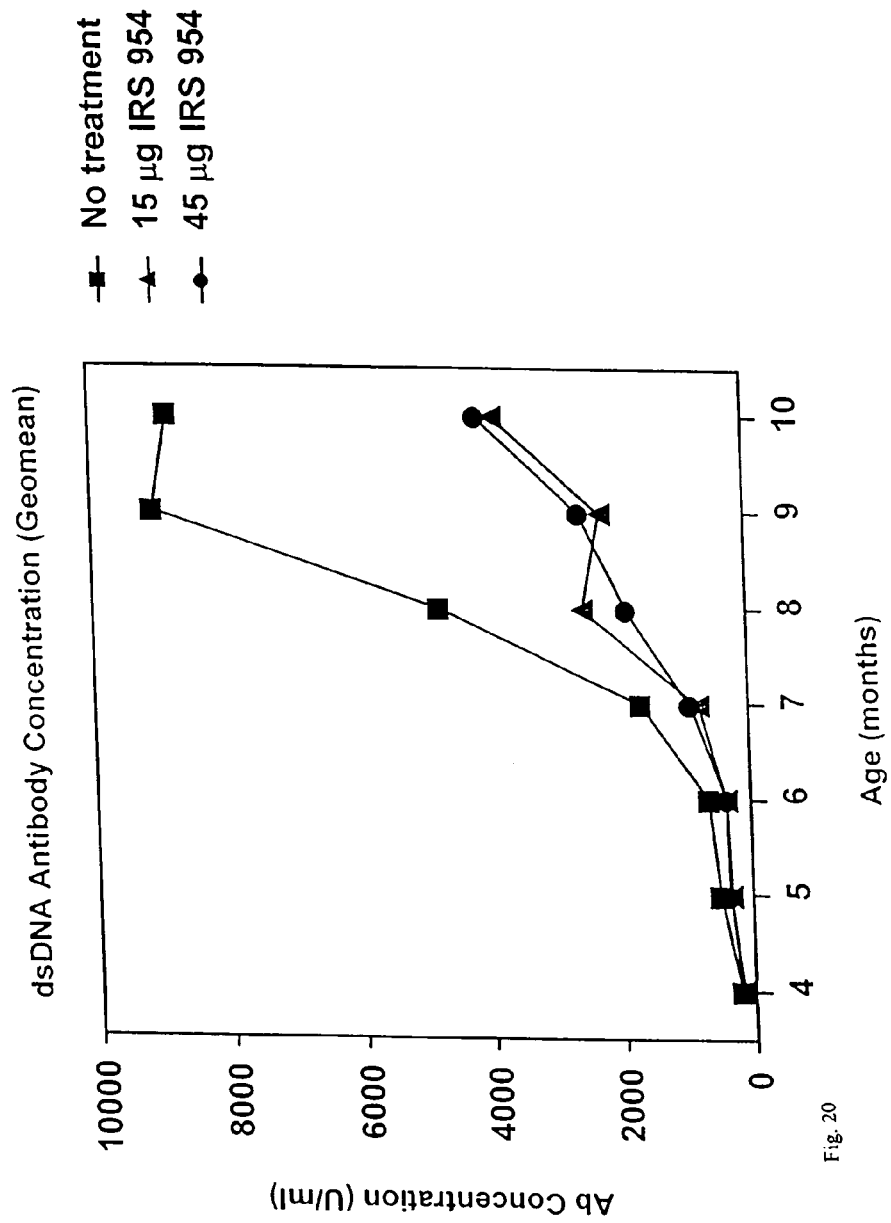
FIG. 20 is a graph showing the levels in the serum of (NZBxNZW)$F_1$ mice of anti-dsDNA autoantibodies in absence of treatment or after injection twice a week with 15 μg or 45 μg of IRP SEQ ID NO:52 (954).
Figure 21:
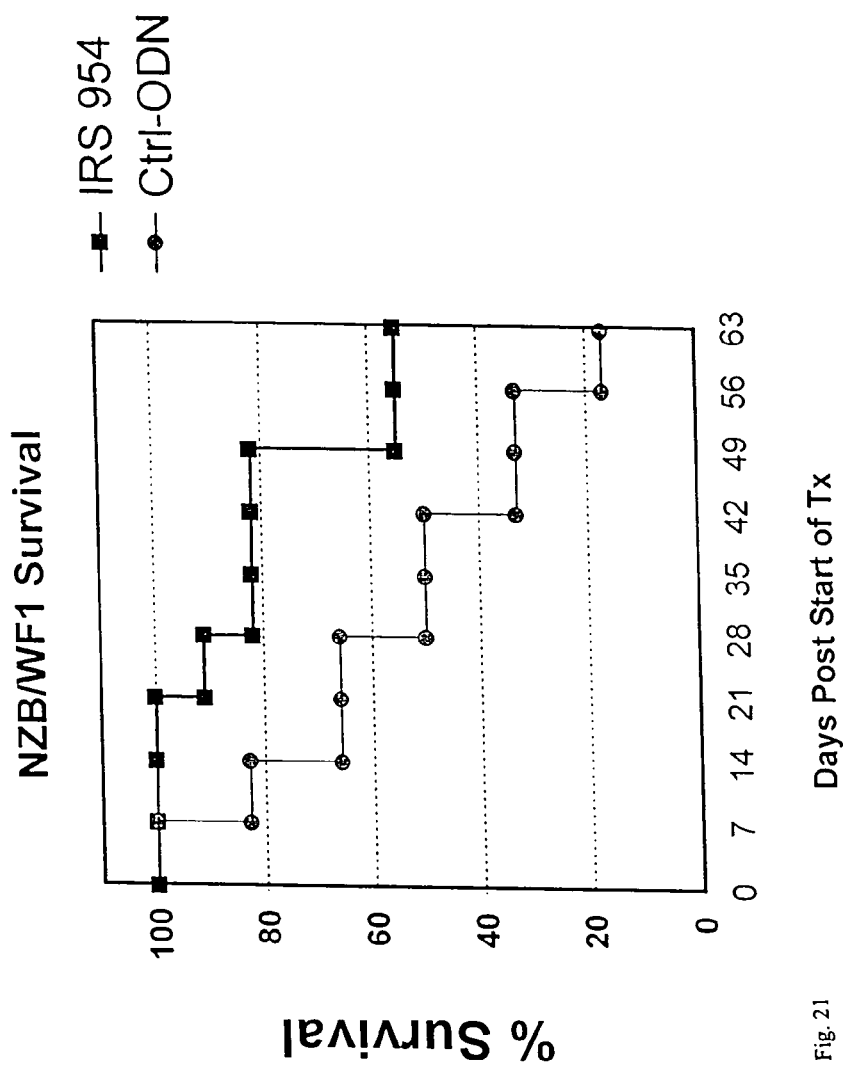
FIG. 21 is a graph showing the percentage of (NZBxNZW) $F_1$ mice alive after injection three times a week at 8-9 months of age with 10 μg of IRP SEQ ID NO:52 (954) or control oligonucleotide.
Figure 22:
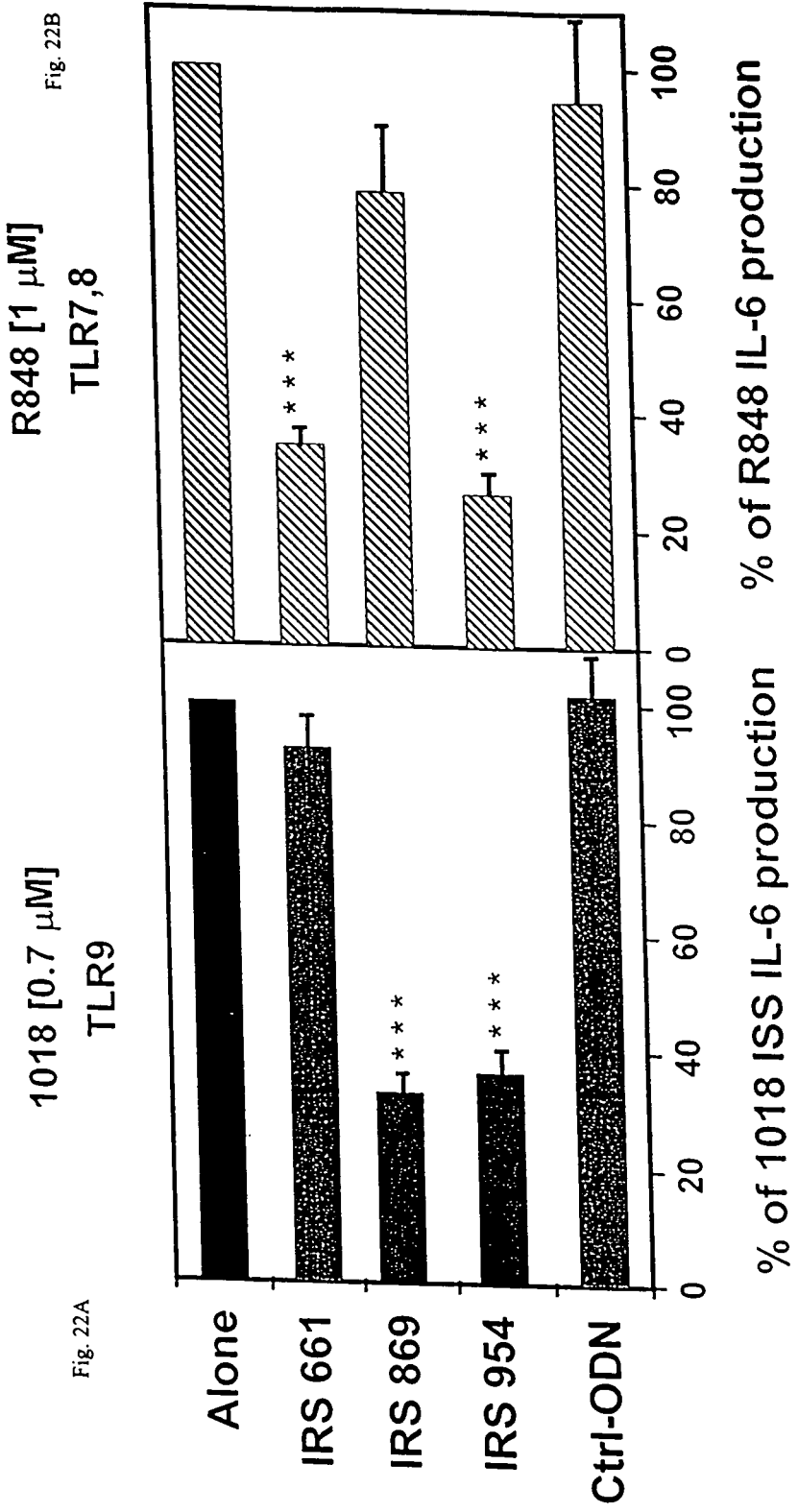
FIGS. 22A-22B are graphs showing IL-6 production from human B cells stimulated with FIG. 22A, ISNA SEQ ID NO:119 (1018) or FIG. 22B, R848 alone and together with IRP SEQ ID NO:17 (869), IRP SEQ ID NO 27 (661), IRP SEQ ID NO:52 (954) or control oligonucleotide.

(NZBxNZW)F$_1$ mice were either left untreated or treated twice a week with 15 µg or 45 µg of IRP SEQ ID NO:52 (954). Treatment started at 4-5 months of age when the first signs of the disease appeared in the mice. As depicted in FIG. 20, levels in the serum of anti-dsDNA autoantibodies in absence of treatment increased over time. Mice injected with IRP SEQ ID NO:52 (954) had reduced levels of autoantibodies which demonstrate its ability to affect progression of the disease of this lupus-prone mice 8-9 months old and already sick (NZBxNZW)F$_1$ mice were injected with 100 µg of IRP SEQ ID NO:52 (954) or control oligonucleotide three time a week. As depicted in FIG. 21, treatment with IRP SEQ ID NO:52 (954) reduced mortality of the mice as compared with control oligonucleotide.

Figure 24:
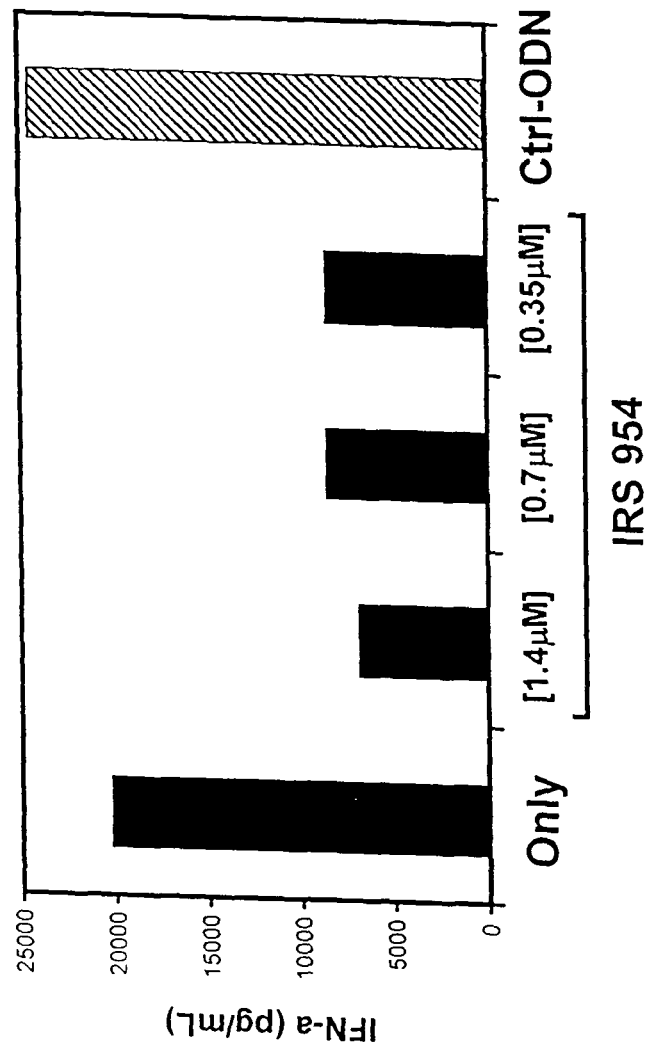
FIG. 24 is a graph showing IFN-α production from human PDC cells stimulated with heat-inactivated influenza virus alone and together with IRP SEQ ID NO:52 (954) or control oligonucleotide.

Purified human B cells were activated with ISNA SEQ ID NO:119 (1018) or R848 alone and together with IRP SEQ ID NO:17 (869), IRP SEQ ID NO:27 (661), IRP SEQ ID NO:52 (954) or control oligonucleotide. As depicted in FIG. 24, the pattern of inhibitory activity of these oligonucleotides is similar in mouse and man. In particular, IRP SEQ ID NO:52 (954) inhibited IL-6 production from human B cells stimulated with both stimuli.

Figure 23:
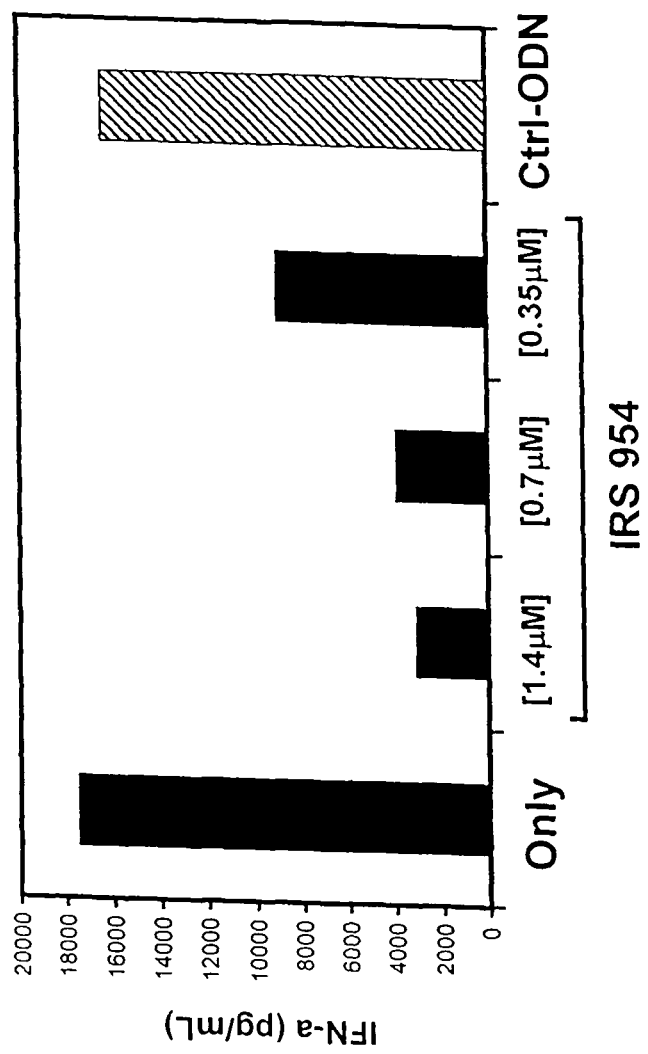
FIG. 23 is a graph showing IFN-α production from human PDC cells stimulated with UV-inactivated HSV-1 virus alone and together with IRP SEQ ID NO:52 (954) or control oligonucleotide.

Human PDCs were infected with UV-inactivated HSV-1 virus alone (MOI:5) and together with IRP SEQ ID NO:52 (954) or control oligonucleotide. FIG. 23 depicts an example of the strong inhibitory effect of IRP SEQ ID NO:52 (954) on the production of IFN-α in response to the virus alone.

Human PDCs were infected with heat-inactivated influenza virus alone (MOI:2) and together with IRP SEQ ID NO:52 (954) or control oligonucleotide. FIG. 24 depicts an example of the strong inhibitory effect of IRP SEQ ID NO:52 (954) on the production of IFN-α in response to the virus alone.

Figure 25:
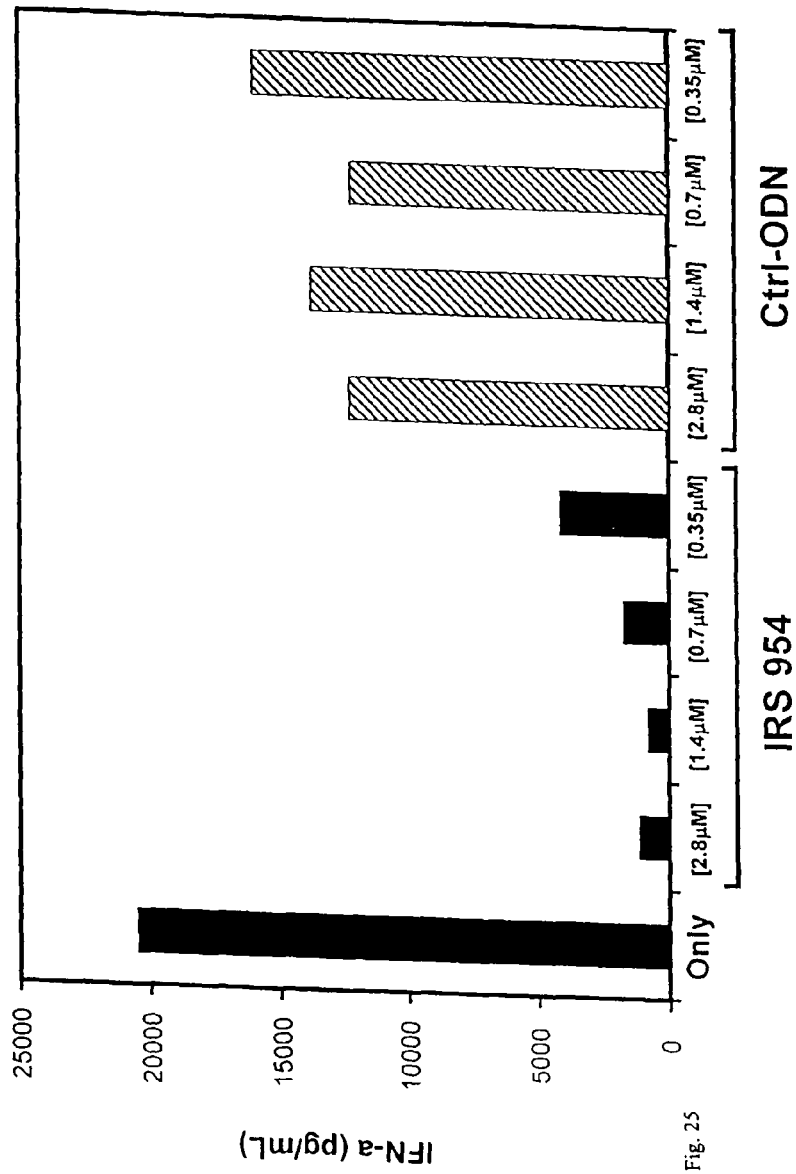
FIG. 25 is a graph showing IFN-α production from human PDC cells stimulated with serum containing anti-dsDNA immune complexes alone and together with IRP SEQ ID NO:52 (954) or control oligonucleotide.

Human PDCs were cultured in the presence of UV-irradiated (60 mJ) U937 cells in the presence of 10% serum obtained from anti-dsDNA positive SLE patients alone and together with IRP SEQ ID NO:52 (954) or control oligonucleotide. As depicted in FIG. 25, the serum containing anti-dsDNA can activated PDC and induce IFN-α. When added in the culture, however, IRP SEQ ID NO:52 (954) could inhibit the IFN-α response while control oligonucleotide had no effect. This demonstrate that IRP SEQ ID NO:52 (954) can significantly inhibit PDC activation in this in vitro assay that is using samples from SLE patients.

Figure 26:
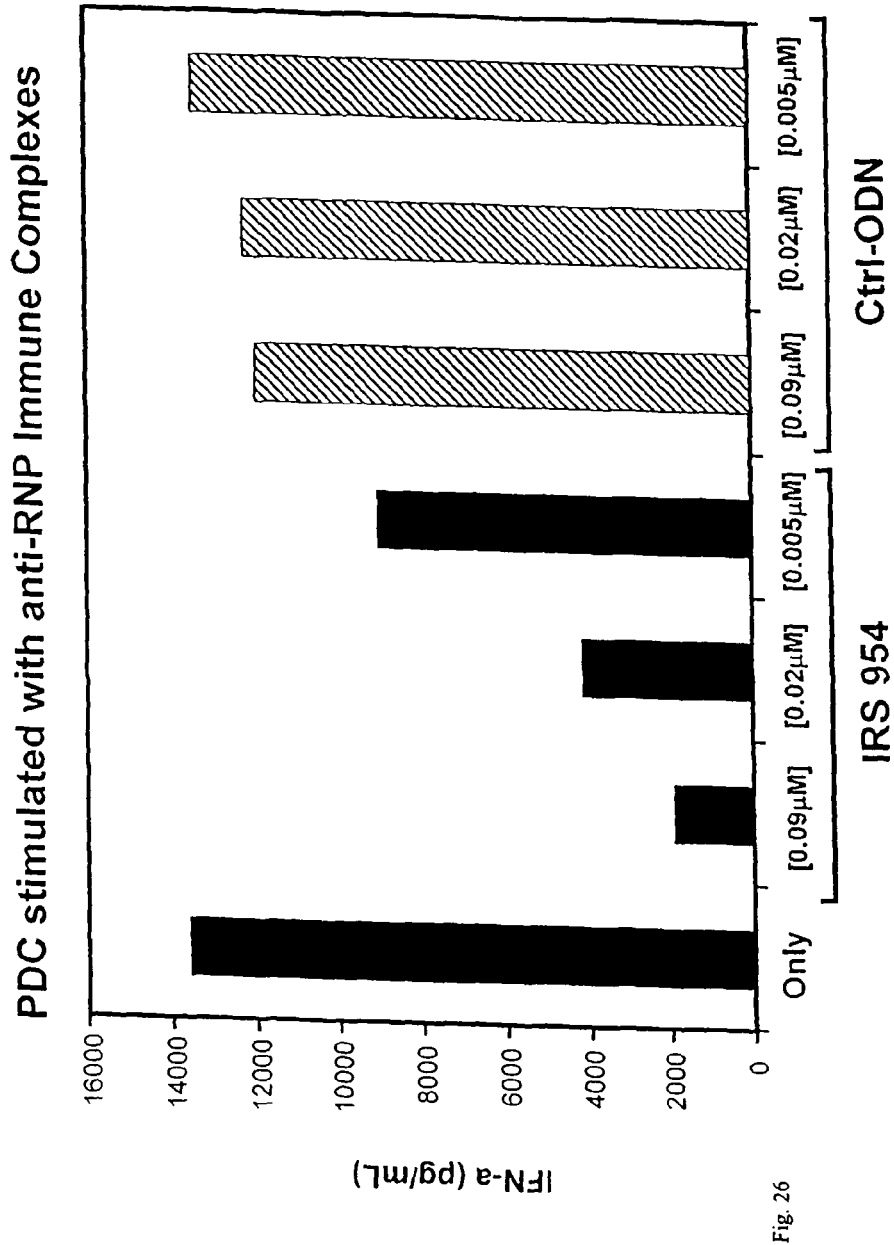
FIG. 26 is a graph showing IFN-α production from human PDC cells stimulated with anti-RNP immune complexes alone and together with IRP SEQ ID NO:52 (954) or control oligonucleotide.

Human PDCs were cultured in the presence of UV-irradiated (60 mJ) U937 cells in the presence of 0.5 mg/ml of purified IgG from anti-RNP positive SLE patients alone and together with IRP SEQ ID NO:52 (954) or control oligonucleotide. The IgG were purified from serum of patients using HiTrap Protein G HP column (GE Healthcare, Waukesha, Wis.). Once purified, IgG were desalted and then quantified. As depicted in FIG. 26, the anti-RNP-specific IgG can activated PDC and induce IFN-α. When added in the culture, however, IRP SEQ ID NO:52 (954) could inhibit the IFN-α response while control oligonucleotide had no effect. This demonstrate that IRP SEQ ID NO:52 (954) can significantly inhibit PDC activation in this in vitro assay that is using samples from SLE patients.

Murine splenocytes were activated with ISNA SEQ ID NO:119 (1018) or R848 alone and together with IRP SEQ ID NO:17 (869), IRP SEQ ID NO:27 (661), IRP SEQ ID NO:52 (954), IRP SEQ ID NO:106 (983), IRP SEQ ID NO:107

Figure 27:
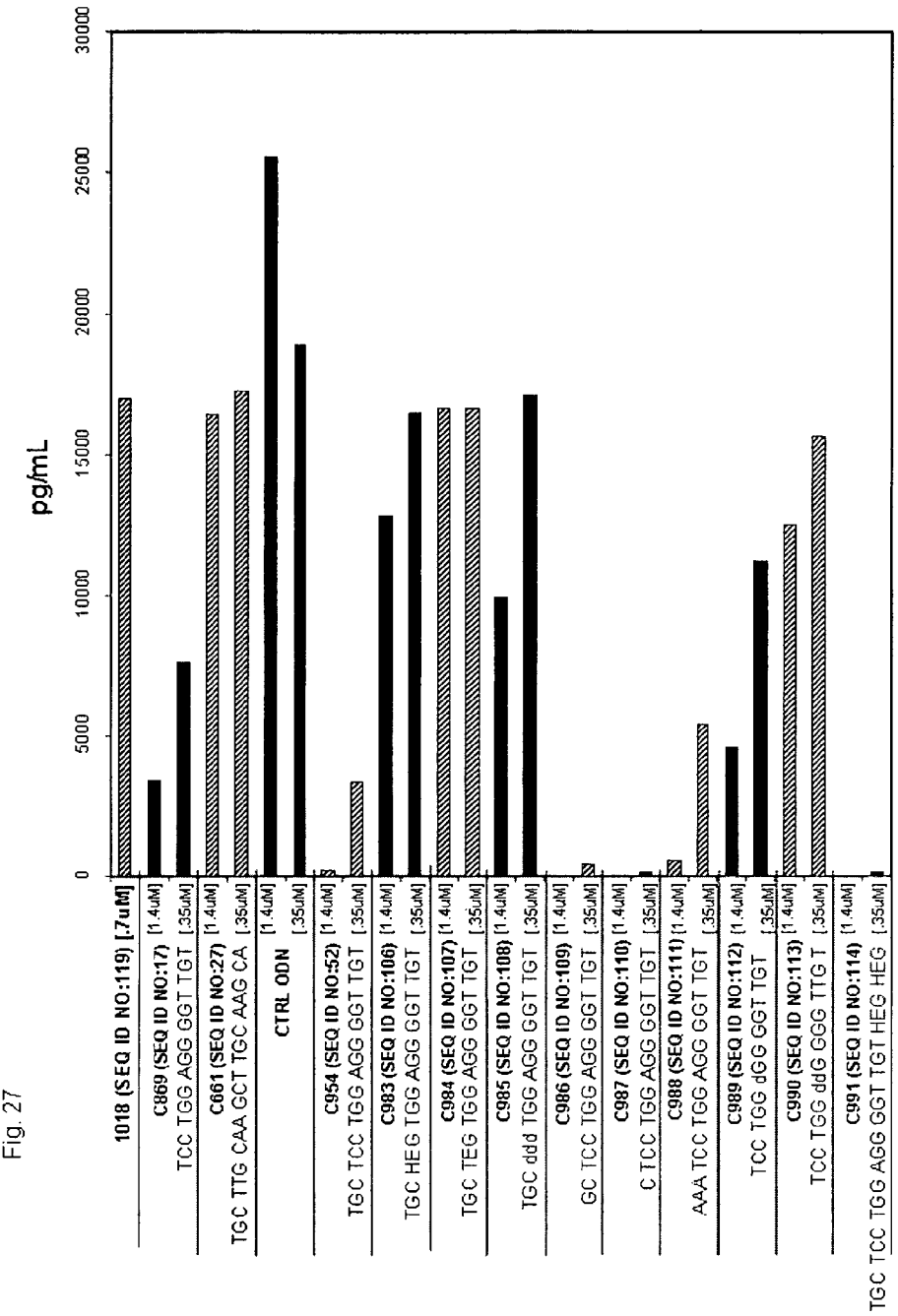
FIG. 27 is a graph showing IL-6 production from murine splenocytes stimulated with ISNA SEQ ID NO:119 (1018) alone and together with IRP SEQ ID NO:17 (869), IRP SEQ ID NO:27 (661), IRP SEQ ID NO:52 (954), IRP SEQ ID NO:106 (983), IRP SEQ ID NO:107 (984), IRP SEQ ID NO:108 (985), IRP SEQ ID NO:109 (986), IRP SEQ ID NO:110 (987), IRP SEQ ID NO:111 (988), IRP SEQ ID NO:112 (989), IRP SEQ ID NO:113 (990), IRP SEQ ID NO:114 (991) or control oligonucleotide.
Figure 28:
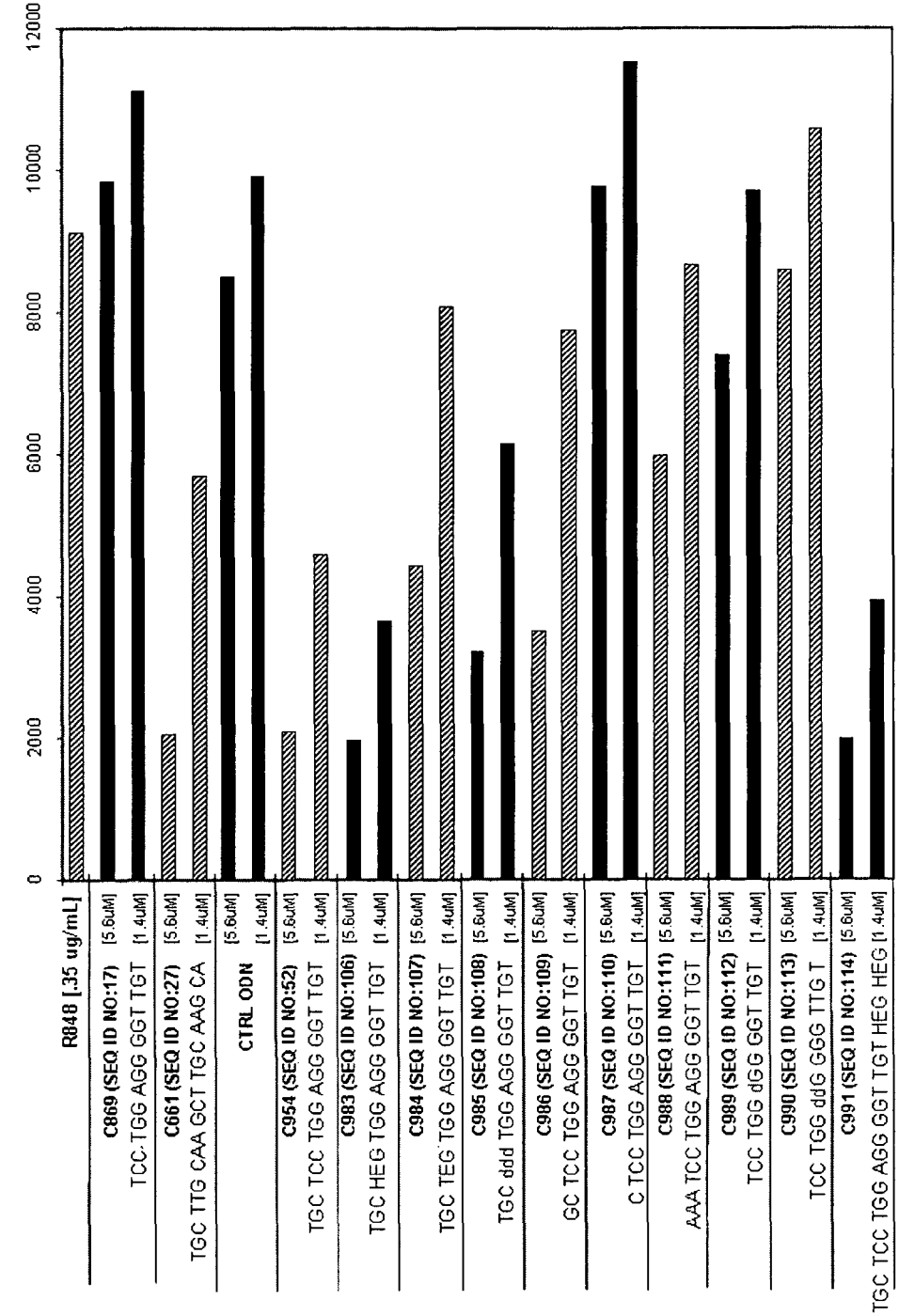
FIG. 28 is a graph showing IL-6 production from murine splenocytes stimulated with R848 alone and together with IRP SEQ ID NO:17 (869), IRP SEQ ID NO:27 (661), IRP SEQ ID NO:52 (954), IRP SEQ ID NO:106 (983), IRP SEQ ID NO:107 (984), IRP SEQ ID NO:108 (985), IRP SEQ ID NO:109 (986), IRP SEQ ID NO:110 (987), IRP SEQ ID NO:111 (988), IRP SEQ ID NO:112 (989), IRP SEQ ID NO:113 (990), IRP SEQ ID NO:114 (991) or control oligonucleotide.

(984), IRP SEQ ID NO:108 (985), IRP SEQ ID NO:109 (986), IRP SEQ ID NO:110 (987), IRP SEQ ID NO:111 (988), IRP SEQ ID NO:112 (989), IRP SEQ ID NO:113 (990), IRP SEQ ID NO:114 (991) or control oligonucleotide. As depicted in FIG. 27 and FIG. 28, adding non-nucleotide groups did not lead to complete loss of activity even though it could modulate the level of the response.

Although the foregoing invention has been described in some detail by way of illustration and example for purposes of clarity and understanding, it will be apparent to those skilled in the art that certain changes and modifications may be practiced. Therefore, descriptions and examples should not be construed as limiting the scope of the invention.

What is claimed is:

1. A method of inhibiting a TLR7/8 dependent immune response in an individual, wherein the individual is a human, the method comprising administering to the individual a composition comprising an oligonucleotide, in an amount sufficient to inhibit the TLR7/8 dependent immune response in said individual, wherein the oligonucleotide comprises SEQ ID NO: 105 or an analog of SEQ ID NO: 105 at the 5' end of the oligonucleotide, the oligonucleotide is less than 50 bases or base pairs and does not comprise a CG dinucleotide, and wherein in the analog of SEQ ID NO: 105 one or two principal bases other than TGC of SEQ ID NO: 105 are each replaced with a naturally or occurring base or a modified, non-naturally occurring base.

2. A method of regulating a TLR7/8 dependent and/or TLR9 dependent immune response in an individual, comprising administering to the individual an oligonucleotide comprising the nucleotide sequence: 5'-TGCN$_m$TCCTGGAGGGGTTGT-3' (SEQ ID NO:6), wherein each N is a nucleotide and m is an integer from 0 to 100, in an amount sufficient to regulate the immune response in said individual.

3. A method of suppressing TLR7/8 dependent cytokine production in an individual, wherein the individual is a human, the method comprising administering to the individual a composition comprising an oligonucleotide, in an amount sufficient to suppress TLR7/8 dependent cytokine production in said individual, wherein the oligonucleotide comprises SEQ ID NO: 105 or an analog of SEQ ID NO: 105 at the 5' end of the oligonucleotide, the oligonucleotide is less than 50 bases or base pairs and does not comprise a CG dinucleotide, and wherein in the analog of SEQ ID NO: 105 one or two principal bases other than TGC of SEQ ID NO: 105 are each replaced with a naturally or non naturally occurring base or a modified, non-naturally occurring base.

4. A method of suppressing TLR9 dependent cytokine production and TLR7/8 dependent cytokine production in an individual, wherein the individual is a human, the method comprising administering to the individual a composition comprising an oligonucleotide, in an amount sufficient to suppress TLR9 dependent cytokine production and TLR7/8 dependent cytokine production in said individual, wherein the oligonucleotide comprises SEQ ID NO: 103 or an analog of SEQ ID NO: 103 at the 5' end of the oligonucleotide, the oligonucleotide is less than 50 bases or base pairs and does not comprise a CG dinucleotide, and wherein in the analog of SEQ ID NO: 103 one or two principal bases other than TGC of SEQ ID NO: 103 are each replaced with a naturally occurring base or a modified, non-naturally occurring base.

5. The method of claim 1, wherein the oligonucleotide comprises a 5'-GGGG-3' sequence.

6. The method of claim 1, wherein the oligonucleotide is selected from the group consisting of SEQ ID NO:52 and SEQ ID NO:114.

7. The method of claim 3, wherein the oligonucleotide comprises a 5'-GGGG-3' sequence.

8. The method of claim 3, wherein the oligonucleotide is selected from the group consisting of SEQ ID NO:52 and SEQ ID NO:114.

9. The method of claim 4, wherein the oligonucleotide comprises a 5'-GGGG-3' sequence.

10. The method of claim 4, wherein the oligonucleotide is selected from the group consisting of SEQ ID NO:52 and SEQ ID NO: 114.

11. The method of claim 1, wherein the oligonucleotide contains phosphate-modified linkages.

12. The method of claim 11, wherein the oligonucleotide contains only phosphorothioate linkages.

13. The method of claim 2, wherein the oligonucleotide contains phosphate-modified linkages.

14. The method of claim 13, wherein the oligonucleotide contains only phosphorothioate linkages.

15. The method of claim 3, wherein the oligonucleotide contains phosphate-modified linkages.

16. The method of claim 15, wherein the oligonucleotide contains only phosphorothioate linkages.

17. The method of claim 4, wherein the oligonucleotide contains phosphate-modified linkages.

18. The method of claim 17, wherein the oligonucleotide contains only phosphorothioate linkages.

19. The method of claim 1, wherein the oligonucleotide comprises one of the group consisting of SEQ ID NO:100, SEQ ID NO:101, SEQ ID NO:102, SEQ ID NO:103, SEQ ID NO:104 and SEQ ID NO:105.

20. The method of claim 1, wherein the oligonucleotide comprises an analog of SEQ ID NO: 105 in which one of said principal bases other than the TGC is replaced with said naturally occurring base or said modified, non-naturally occurring base.

21. The method of claim 1, wherein the oligonucleotide is less than 40 bases in length.

22. The method of claim 21, wherein the oligonucleotide is less than 20 bases in length.

23. The method of claim 2, wherein the oligonucleotide is less than 40 bases in length.

24. The method of claim 23, wherein the oligonucleotide is less than 20 bases in length.

25. The method of claim 3, wherein the oligonucleotide comprises one of the group consisting of SEQ ID NO:100, SEQ ID NO:101, SEQ ID NO:102, SEQ ID NO:103, SEQ ID NO:104 and SEQ ID NO:105.

26. The method of claim 3, wherein the oligonucleotide comprises an analog of SEQ ID NO: 105 in which one of said principal bases other than the TGC is replaced with said naturally occurring base or said modified, non-naturally occurring base.

27. The method of claim 3, wherein the oligonucleotide is less than 40 bases in length.

28. The method of claim 27, wherein the oligonucleotide is less than 20 bases in length.

29. The method of claim 4, wherein the oligonucleotide comprises one of the group consisting of SEQ ID NO:100, SEQ ID NO:101, SEQ ID NO:102, and SEQ ID NO:103.

30. The method of claim 4, wherein the oligonucleotide comprises an analog of SEQ ID NO: 103 in which one of said principal bases other than the TGC is replaced with said naturally occurring base or said modified, non-naturally occurring base.

31. The method of claim 4, wherein the oligonucleotide is less than 40 bases in length.

32. The method of claim 31, wherein the oligonucleotide is less than 20 bases in length.

* * * * *